United States Patent
Doud et al.

(10) Patent No.: US 12,162,902 B2
(45) Date of Patent: Dec. 10, 2024

(54) DECARBOXYLASE INHIBITORS FOR TREATING PARKINSON'S DISEASE

(71) Applicant: SAIL BIOMEDICINES, Cambridge, MA (US)

(72) Inventors: Devin Forest Reed Doud, Arlington, MA (US); Timothy Briggs, Waltham, MA (US); Steven Taylor, Winchester, MA (US); Elijah Bogart, Cambridge, MA (US); John Proudfoot, Newtown, CT (US); Dinara Shashanka Gunasekera, Cambridge, MA (US); Spencer Cory Peck, Watertown, MA (US); Angela She, Cambridge, MA (US); William McElroy, Cambridge, MA (US); Bernard Lanter, Somerville, MA (US); Michael Rutlin, Brookline, MA (US)

(73) Assignee: Sail Biomedicines, Cambridge, MA (US)

( * ) Notice: Subject to any disclaimer, the term of this patent is extended or adjusted under 35 U.S.C. 154(b) by 605 days.

(21) Appl. No.: 17/299,854

(22) PCT Filed: Dec. 6, 2019

(86) PCT No.: PCT/US2019/064896
§ 371 (c)(1),
(2) Date: Jun. 4, 2021

(87) PCT Pub. No.: WO2020/118163
PCT Pub. Date: Jun. 11, 2020

(65) Prior Publication Data
US 2022/0048849 A1    Feb. 17, 2022

Related U.S. Application Data

(60) Provisional application No. 62/776,459, filed on Dec. 6, 2018.

(51) Int. Cl.

| | | |
|---|---|---|
| C07H 15/12 | (2006.01) |
| C07C 211/63 | (2006.01) |
| C07C 215/40 | (2006.01) |
| C07C 215/44 | (2006.01) |
| C07C 215/52 | (2006.01) |
| C07C 229/12 | (2006.01) |
| C07C 229/36 | (2006.01) |
| C07C 233/51 | (2006.01) |
| C07C 271/22 | (2006.01) |
| C07C 311/05 | (2006.01) |
| C07C 317/28 | (2006.01) |
| C07D 205/04 | (2006.01) |
| C07D 207/08 | (2006.01) |
| C07D 231/04 | (2006.01) |
| C07D 257/04 | (2006.01) |
| C07D 263/32 | (2006.01) |
| C07D 265/30 | (2006.01) |
| C07D 265/32 | (2006.01) |
| C07D 271/06 | (2006.01) |
| C07D 295/15 | (2006.01) |
| C07D 303/36 | (2006.01) |
| C07D 305/06 | (2006.01) |
| C07D 453/02 | (2006.01) |

(Continued)

(52) U.S. Cl.
CPC ............ *C07H 15/12* (2013.01); *C07C 211/63* (2013.01); *C07C 215/40* (2013.01); *C07C 215/44* (2013.01); *C07C 215/52* (2013.01); *C07C 229/12* (2013.01); *C07C 229/36* (2013.01); *C07C 233/51* (2013.01); *C07C 271/22* (2013.01); *C07C 311/05* (2013.01); *C07C 317/28* (2013.01); *C07D 205/04* (2013.01); *C07D 207/08* (2013.01); *C07D 231/04* (2013.01); *C07D 257/04* (2013.01); *C07D 263/32* (2013.01); *C07D 265/30* (2013.01); *C07D 265/32* (2013.01); *C07D 271/06* (2013.01); *C07D 295/15* (2013.01); *C07D 303/36* (2013.01); *C07D 305/06* (2013.01); *C07D 453/02* (2013.01); *C07D 493/04* (2013.01); *C07F 5/025* (2013.01); *C07F 9/3817* (2013.01); *C07F 9/4009* (2013.01); *C07H 15/18* (2013.01); *C12Q 1/68* (2013.01); *C07C 2601/02* (2017.05); *C07C 2601/04* (2017.05)

(58) Field of Classification Search
CPC ... C07C 215/52; C07C 229/36; C07C 233/51; C07C 271/22
See application file for complete search history.

(56) References Cited

U.S. PATENT DOCUMENTS

| | | | | |
|---|---|---|---|---|
| 4,325,961 A | * | 4/1982 | Kollonitsch | ......... C07D 233/64 562/571 |
| 2022/0016253 A1 | * | 1/2022 | Heldman | ............... C07C 231/12 |

FOREIGN PATENT DOCUMENTS

| | | | | |
|---|---|---|---|---|
| GB | 2048875 A | * | 12/1980 | ............. A61K 31/13 |
| WO | WO-2007093450 A2 | * | 8/2007 | ............. A61P 25/00 |

OTHER PUBLICATIONS

U.S. Appl. No. 17/995,749, filed Oct. 7, 2022, Doud D.*

(Continued)

*Primary Examiner* — Eric Olson
*Assistant Examiner* — Samuel L Galster
(74) *Attorney, Agent, or Firm* — Finnegan, Henderson, Farabow, Garrett & Dunner LLP

(57) ABSTRACT

Provided are inhibitors of pathogenic, bacterial metabolite production and conjugates of the inhibitors. Also provided are pharmaceutical compositions containing the inhibitors or conjugates and methods of using the same.

19 Claims, No Drawings

(51) Int. Cl.
*C07D 493/04* (2006.01)
*C07F 5/02* (2006.01)
*C07F 9/38* (2006.01)
*C07F 9/40* (2006.01)
*C07H 15/18* (2006.01)
*C12Q 1/68* (2018.01)

(56) References Cited

OTHER PUBLICATIONS

Davies, S. G., et al., Org. Lett. 2015, 17, 2254-2257. (Year: 2015).*
Granados, A. et al., J. Org. Chem. 2018, 83, 303-313. (Year: 2018).*
Kaufmann, H. Clin. Auton. Res. (2008) 18[Suppl 1]:19-24. (Year: 2008).*

* cited by examiner

DECARBOXYLASE INHIBITORS FOR TREATING PARKINSON'S DISEASE

This application is a national stage filing under 35 U.S.C. § 371 of International Application No. PCT/US2019/064896, filed on Dec. 6, 2019, which claims priority to U.S. provisional application No. 62/776,459, filed Dec. 6, 2018; the disclosure of all of which are incorporated herein by reference in their entirety.

The present disclosure provides compounds, pharmaceutical compositions comprising the same, and methods of using the same.

Mammalian microbiota can engage in a bidirectional communication with the mammalian host system. In some instances, mammalian microbiota may be responsible for producing enzymes that can mediate formation of pathologic metabolites. These metabolites, in sufficient quantities, can compromise the host's health and often lead to debilitating diseases. Therapeutic approaches targeting enzymatic production of pathogenic, bacterial metabolites remain largely unutilized.

There is a need for therapeutic strategies that address disease etiology. In particular, there is a need for therapeutic strategies that target enzymatic production of the pathogenic, bacterial metabolites.

In general, the present disclosure provides novel compounds which may act as inhibitors of enzymatic production of pathogenic, bacterial metabolites, pharmaceutical compositions comprising at least one of such compounds, and methods for using the same.

In one aspect, the present disclosure provides compounds for inhibiting a decarboxylase-mediated conversion of L-DOPA to L-dopamine. In some embodiments, the decarboxylase is tyrosine decarboxylase. In some embodiments, the decarboxylase is bacterial tyrosine decarboxylase.

In some embodiments, the present disclosure provides compounds of formula (I):

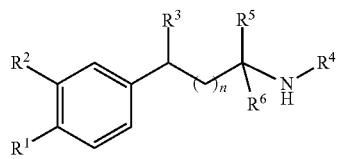

and pharmaceutically acceptable salts thereof,
wherein
  n is 0 or 1;
  R is H or $C_{1-6}$ alkyl;
  $R^1$ is H or —$OR^A$, wherein $R^A$ is H, —$C(O)C_{1-6}$ alkyl, or an acylated sugar;
  $R^2$ is H, halogen, amino, $C_{1-6}$ alkyl, or —$OR^A$, wherein $R^A$ is H or an acylated sugar;
  $R^3$ is H, a halogen, —OH, or $C_{1-6}$ alkyl optionally substituted with one or more halogens;
  $R^4$ is H, —$NH_2$, —$C(O)OCH_3$, or an acylated sugar;
  $R^5$ is H, —$C(O)OH$, —$C(O)OC_{1-6}$ alkyl, —$C(O)Oglycoside$, —$C(O)NHOH$, or —$C(O)O(acylated sugar)$; and
  $R^6$ is H, halogen, or optionally substituted $C_{1-6}$ alkyl;
  provided that at least one $R^A$ is present; or provided that $R^3$ and/or $R^6$ comprise a halogen.

In some embodiments, the present disclosure provides compounds of formula (II):

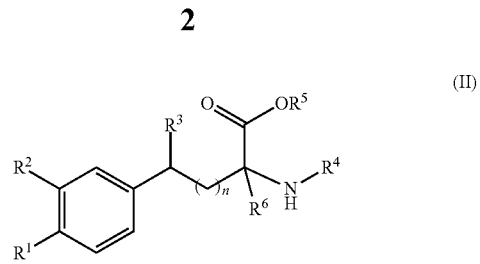

and pharmaceutically acceptable salts thereof,
wherein
  n is 0 or 1;
  each of $R^1$ and $R^2$ is independently H or —$OR^A$, wherein each $R^A$ is independently H or an acylated sugar, or $R^1$ is —$C(O)C_{1-6}$ alkyl;
  $R^3$ is H or a halogen;
  $R^4$ is H, —$NH_2$, —$C(O)OCH_3$, or an acylated sugar;
  $R^5$ is H, $C_{1-6}$ alkyl, glycoside, or an acylated sugar; and
  $R^6$ is H or optionally substituted $C_{1-6}$ alkyl;
  provided that at least one $R^A$ is present; or provided that $R^3$ and/or $R^6$ comprise a halogen.

In some embodiments, the compound is of formula (I-a):

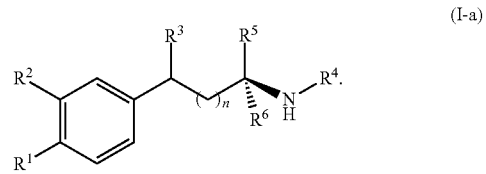

In some embodiments, $R^1$ is —$OR^A$. In some embodiments, $R^2$ is H or —$OR^A$. In some embodiments, each $R^A$ is H. In some embodiments, $R^3$ is fluoro or chloro. In some embodiments, $R^4$ is H. In some embodiments, $R^4$ is —$NH_2$. In some embodiments, $R^5$ is H. In some embodiments, $R^5$ is an acylated sugar. In some embodiments, $R^6$ is H. In some embodiments, $R^6$ is alkyl. In some embodiments, n is 0. In some embodiments, n is 1. In some embodiments, $R^2$ is halogen. In some embodiments, $R^3$ is a $C_{1-6}$ alkyl. In some embodiments, $R^5$ is H. In some embodiments, $R^6$ is halogen.

In some embodiments, the disclosure provides the following compounds:

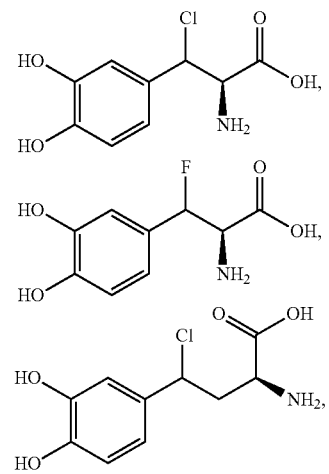

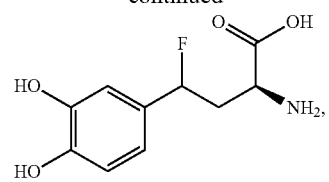
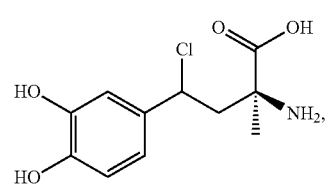
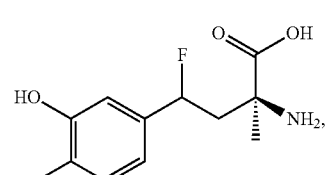
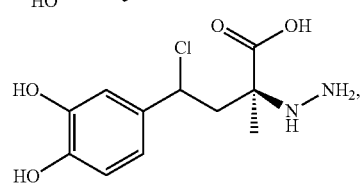
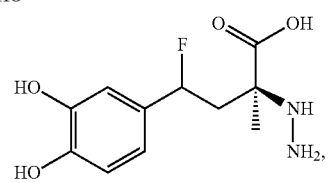
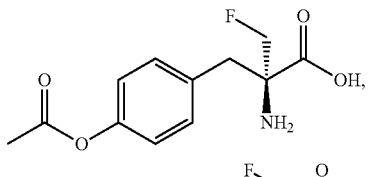
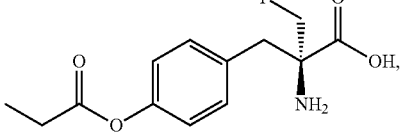
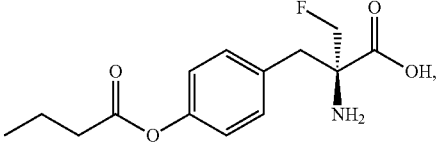
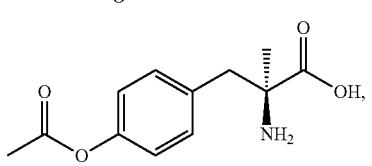
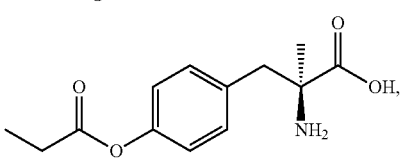
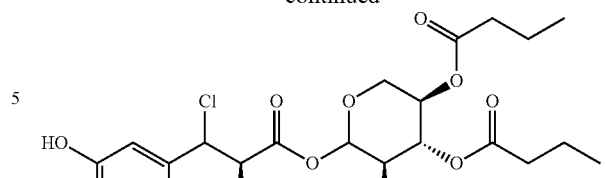
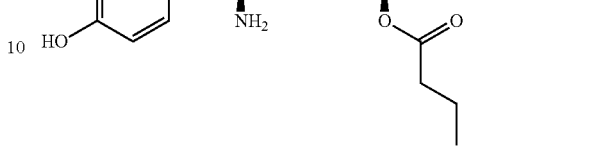
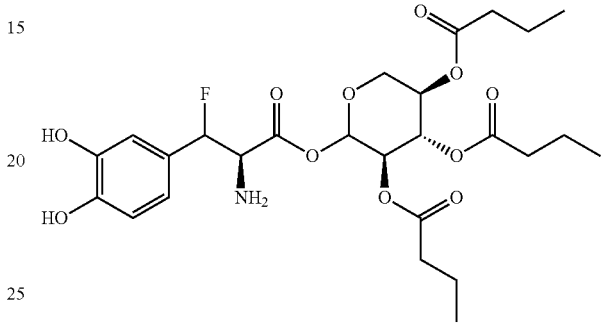
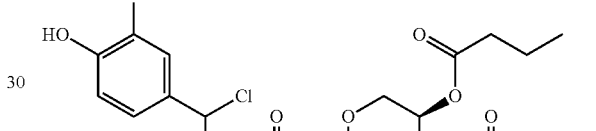
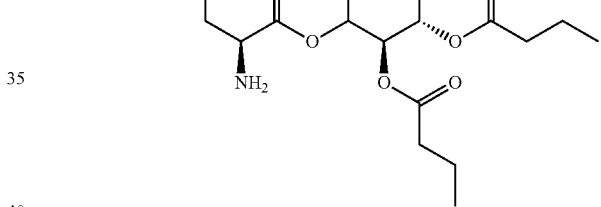
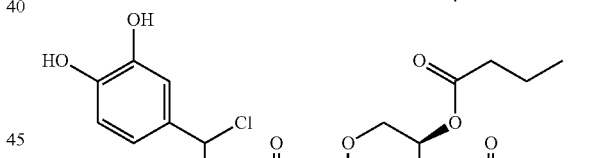
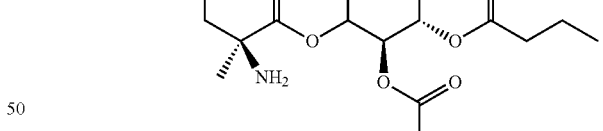
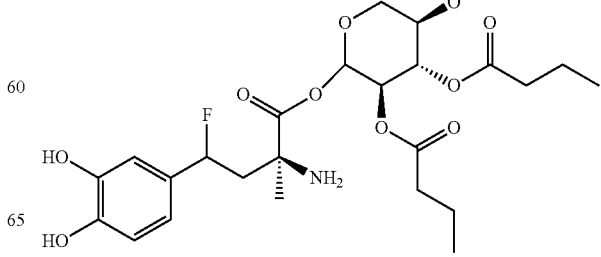

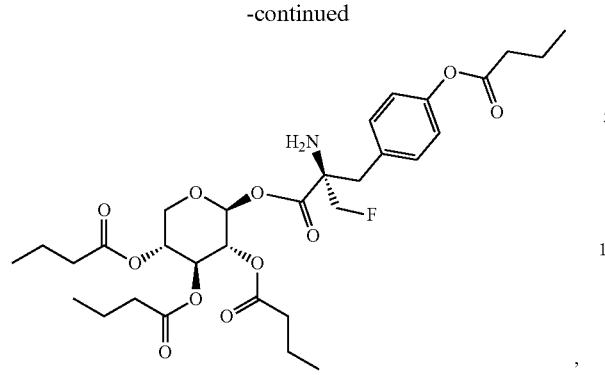
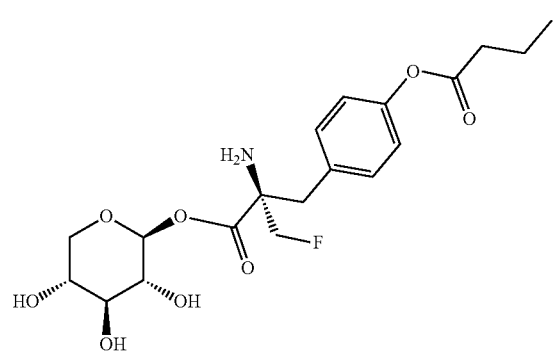
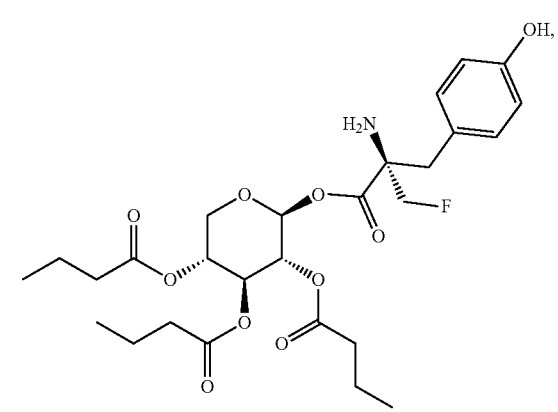
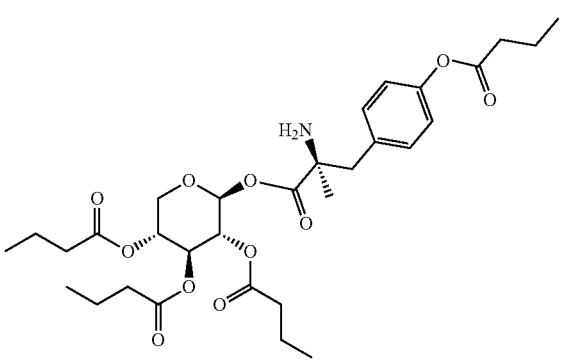
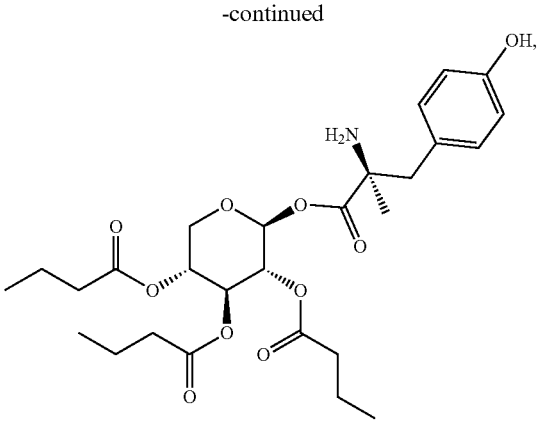
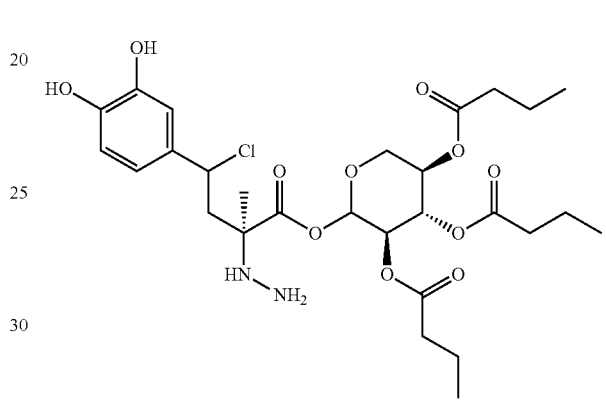
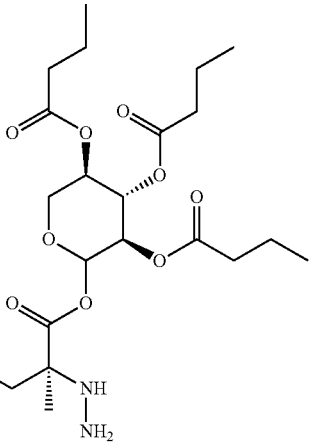
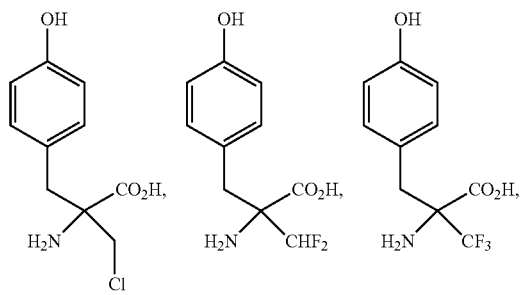

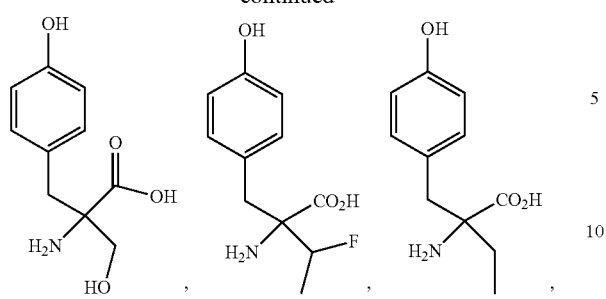
and pharmaceutically acceptable salts thereof. In some embodiments, the disclosure provides the following compounds:
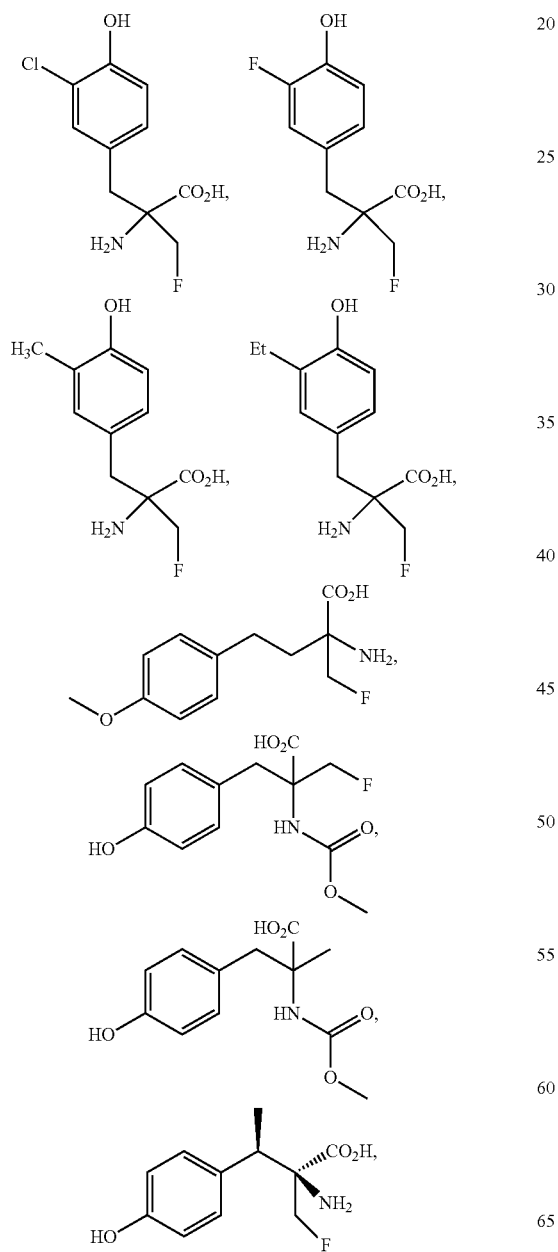
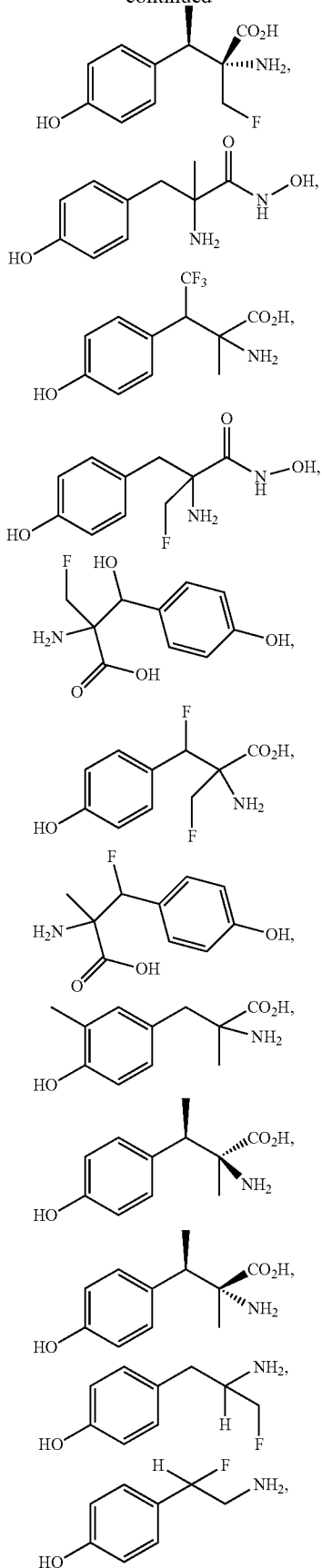

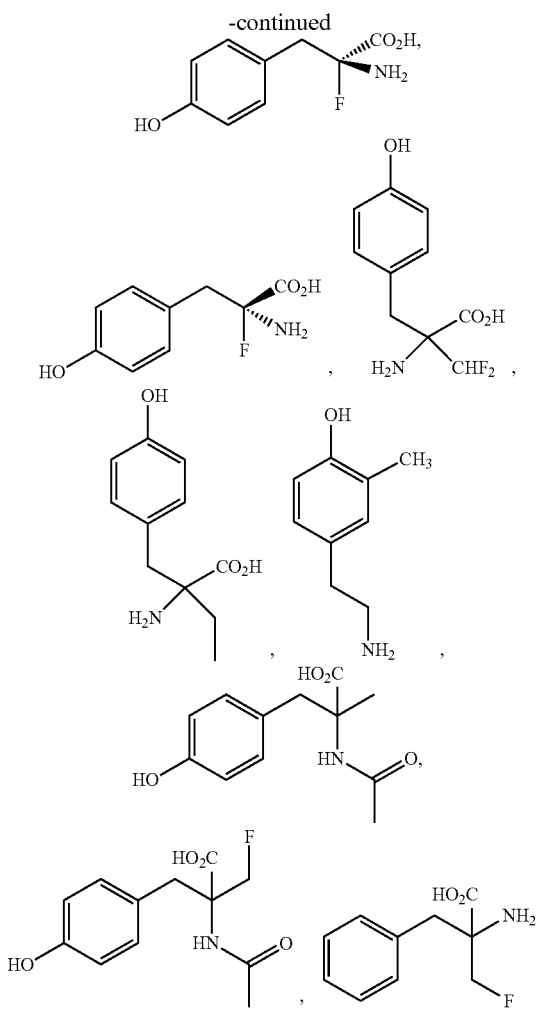

and pharmaceutically acceptable salts thereof.

In some aspects, the present disclosure provides a pharmaceutical composition comprising a pharmaceutically acceptable excipient and at least one compound chosen from compounds of formulas (I) (I-1), (II), compounds of the previously described groups above, and pharmaceutically acceptable salts thereof.

In another aspect, the present disclosure provides a method of treating Parkinson's comprising administering to the subject in need thereof a therapeutically effective amount of at least one entity chosen from compounds of formulas (I), (I-a), (II), compounds of the previously described groups, and pharmaceutically acceptable salts thereof, or a pharmaceutical composition comprising at least one such entity.

In another aspect, the present disclosure provides a method of inhibiting a decarboxylase-mediated conversion of L-DOPA to L-dopamine, the method comprising contacting the decarboxylase with at least one entity chosen from compounds of formulas (I), (I-a), (II), compounds of the previously described groups, and pharmaceutically acceptable salts thereof. In some embodiments, the decarboxylase is tyrosine decarboxylase. In some embodiments, the decarboxylase is bacterial tyrosine decarboxylase.

The term "acyl," as used herein, represents a chemical substituent of formula —C(O)—R, where R is alkyl, alkenyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R. Non-limiting examples of acyl include fatty acid acyls (e.g., short chain fatty acid acyls (e.g., acetyl, propionyl, or butyryl)).

The term "acylated sugar," as used herein, refers to a carbohydrate, sugar acid, or sugar alcohol having one or more hydroxyls substituted with an acyl (e.g., a fatty acid acyl). In some embodiments, the carbohydrate is a monosaccharide. In some embodiments, the fatty acid acyl is a short chain fatty acid acyl (e.g., propionyl or butyryl). An acylated sugar can be a compound or a monovalent group. When an acylated sugar is a monovalent group, the group includes one and only one valency for attaching to another molecular fragment. When an acylated sugar is covalently bonded to a carbon atom of another molecular fragment, the valency is on an oxygen atom of the acylated sugar. When an acylated sugar is covalently bonded to an oxygen atom of another molecular fragment, the valency is on the anomeric carbon atom of the acylated sugar. Non-limiting examples of a monosaccharide include arabinose, xylose, fructose, galactose, glucose, glucosinolate, ribose, tagatose, fucose, and rhamnose. Non-limiting examples of a sugar acid include xylonic acid, gluconic acid, glucuronic acid, galacturonic acid, tartaric acid, saccharic acid, or mucic acid. Non-limiting examples of sugar alcohols are glycerol, erythritol, theritol, arabitol, xylitol, tibitol, mannitol, sorbitol, galactitol, fucitol, iditol, or inositol.

The term "acyloxy," as used herein, represents a chemical substituent of formula —OR, where R is acyl. An optionally substituted acyloxy is an acyloxy that is optionally substituted as described herein for acyl.

The term "alcohol oxygen atom," as used herein, refers to a divalent oxygen atom, where at least one valency of the oxygen atom is bonded to an $sp^3$-hybridized carbon atom.

The term "alkanoyl," as used herein, represents a chemical substituent of formula —C(O)—R, where R is alkyl. An optionally substituted alkanoyl is an alkanoyl that is optionally substituted as described herein for alkyl.

The term "alkoxy," as used herein, represents a chemical substituent of formula —OR, where R is a $C_{1-6}$ alkyl group, unless otherwise specified. An optionally substituted alkoxy is an alkoxy group that is optionally substituted as defined herein for alkyl.

The term "alkenyl," as used herein, represents acyclic monovalent straight or branched chain hydrocarbon groups containing one, two, or three carbon-carbon double bonds. Alkenyl, when unsubstituted, has from 2 to 12 carbon atoms (e.g., 1 to 8 carbons), unless specified otherwise. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkenylene," as used herein, refers to a divalent, straight or branched, unsaturated hydrocarbon including one, two, or three carbon-carbon double bonds, in which two valencies replace two hydrogen atoms. Alkenylene, when unsubstituted, has from 2 to 12 carbon atoms (e.g., 2 to 6 carbons), unless specified otherwise. Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en- 1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. An optionally substituted alkenylene is an alkenylene that is optionally substituted as described herein for alkyl.

The term "alkyl," as used herein, refers to an acyclic, straight or branched, saturated hydrocarbon group, which, when unsubstituted, has from 1 to 12 carbons (e.g., 1 to 6 carbons), unless otherwise specified. Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: alkoxy; acyloxy; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; cyano; oxo (=O); thio (=S); and imino (=NR'), where R' is H, alkyl, aryl, or heterocyclyl. Each of the substituents may itself be unsubstituted or, valency permitting, substituted with unsubstituted substituent(s) defined herein for each respective group.

The term "alkylene," as used herein, refers to a divalent, straight or branched, saturated hydrocarbon, in which two valencies replace two hydrogen atoms. Alkyl, when unsubstituted, has from 2 to 12 carbon atoms (e.g., 2 to 6 carbons), unless specified otherwise. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. An optionally substituted alkylene is an alkylene that is optionally substituted as described herein for alkyl.

The term "alkylsulfinyl," as used herein, represents a group of formula —S(O)-(alkyl). An optionally substituted alkylsulfinyl is an alkylsulfinyl that is optionally substituted as described herein for alkyl.

The term "alkylsulfonyl," as used herein, represents a group of formula —S(O)$_2$-(alkyl). An optionally substituted alkylsulfonyl is an alkylsulfonyl that is optionally substituted as described herein for alkyl.

The term "alkynyl," as used herein, represents an acyclic, monovalent, straight or branched chain hydrocarbon groups containing one, two, or three carbon-carbon triple bonds. Alkynyl, when unsubstituted, has from 2 to 12 carbon atoms (e.g., 2 to 6 carbons), unless specified otherwise. Non-limiting examples of the alkynyl groups include ethynyl, prop-1-ynyl, prop-2-ynyl, but-1-ynyl, but-2-ynyl, but-3-ynyl, and 1-methylprop-2-ynyl. An optionally substituted alkynyl is an alkynyl that is optionally substituted as defined herein for alkyl.

The term "alkynylene," as used herein, refers to a divalent, straight or branched, unsaturated hydrocarbon including one, two, or three carbon-carbon triple bonds, in which two valencies replace two hydrogen atoms. Alkynylene, when unsubstituted, has from 2 to 12 carbon atoms (e.g., 2 to 6 carbons), unless specified otherwise. Non-limiting examples of the alkynylene groups include ethyn-1,2-diyl; prop-1-yn-1,3-diyl; prop-2-yn-1,1-diyl; but-1-yn-1,3-diyl; but-1-yn-1,4-diyl; but-2-yn-1,1-diyl; but-2-yn-1,4-diyl; but-3-yn-1,1-diyl; but-3-yn-1,2-diyl; but-3-yn-2,2-diyl; and buta-1,3-diyn-1,4-diyl. An optionally substituted alkynylene is an alkynylene that is optionally substituted as described herein for alkyl.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; and cyano. Each of the substituents may itself be unsubstituted or substituted with unsubstituted substituent(s) defined herein for each respective group.

The term "aryl alkyl," as used herein, represents an alkyl group substituted with an aryl group. An optionally substituted aryl alkyl is an aryl alkyl, in which aryl and alkyl portions may be optionally substituted as the individual groups as described herein.

The term "arylene," as used herein, is a divalent group that is an aryl group, in which one hydrogen atom is replaced with a valency. Arylene may be optionally substituted as described herein for aryl. Non-limiting examples of arylenes include phenylene (e.g., 1,2-phenylene, 1,3-phenylene, and 1.4-phenylene).

The term "aryloxy," as used herein, represents a group —OR, where R is aryl. Aryloxy may be an optionally substituted aryloxy. An optionally substituted aryloxy is aryloxy that is optionally substituted as described herein for aryl.

The term "carbamate linker," as used herein, refers to a group R$^1$—(CO)—R$^2$, where R$^1$ is a bond to an alcohol or phenolic oxygen atom, and R$^2$ is a bond to a nitrogen atom.

The term "carbohydrate," as used herein, refers to a monosaccharide, disaccharide, or an oligosaccharide or an analog of the following structure:

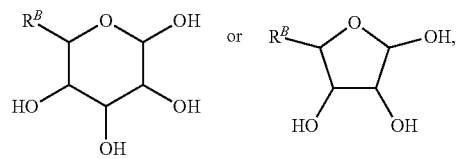

where R$^B$ is H, optionally substituted C$_{1-6}$ alkyl, or —CH$_2$—OH.

The term "carbohydrate" may refer to a compound or to a monovalent or multivalent chemical substituent. When the term "carbohydrate" refers to a chemical substituent, the valence(s) reside on the anomeric carbon atom and/or alcohol oxygen atoms. An optionally substituted carbohydrate is a carbohydrate, in which at least one hydroxyl is substituted with an acyl (e.g., a fatty acid acyl).

The term "carbonate linker," as used herein, refers to a group R$^1$—C(O)—R$^2$, where R$^1$ is a bond to a first alcohol or phenolic oxygen atom, and R$^2$ is a bond to a second alcohol or phenolic oxygen atom.

The term "carbonyl," as used herein, refers to a divalent group —C(O)—.

The term "carboxylate," as used herein, represents group —COOH or a salt thereof.

The term "cycloalkylene," as used herein, represents a divalent group that is a cycloalkyl group, in which one hydrogen atom is replaced with a valency. An optionally substituted cycloalkylene is a cycloalkylene that is optionally substituted as described herein for cycloalkyl.

The term "cycloalkoxy," as used herein, represents a group —OR, where R is cycloalkyl. An optionally substituted cycloalkoxy is cycloalkoxy that is optionally substituted as described herein for cycloalkyl.

The term "dialkylamino," as used herein, refers to a group —NR$_2$, where each R is independently alkyl.

The term "ester bond," as used herein, refers to a covalent bond between an alcohol or phenolic oxygen atom and a carbonyl group that is further bonded to a carbon atom.

The term "fatty acid," as used herein, refers to a short-chain fatty acid, a medium chain fatty acid, a long chain fatty acid, a very long chain fatty acid, or an unsaturated analogue thereof, or a phenyl-substituted analogue thereof. Short chain fatty acids contain from 1 to 6 carbon atoms, medium chain fatty acids contain from 7 to 13 carbon atoms, and a long-chain fatty acids contain from 14 to 22 carbon atoms. A fatty acid may be saturated or unsaturated. An unsaturated fatty acid includes 1, 2, 3, 4, 5, or 6 carbon-carbon double bonds. In some embodiments, the carbon-carbon double bonds in unsaturated fatty acids have Z stereochemistry.

The term "fatty acid acyl," as used herein, refers to a fatty acid, in which the hydroxyl group is replaced with a valency. In some embodiments, a fatty acid acyl is a short chain fatty acid acyl.

The term "fatty acid acyloxy," as used herein, refers to group —OR, where R is a fatty acid acyl.

The term "fluoroalkyl," as used herein, refers to a C$_{1-6}$ alkyl group that is substituted with one or more fluorine atoms; the number of fluorine atoms is up to the total number of hydrogen atoms available for replacement with fluorine atoms. A fluoroalkyl in which all hydrogen atoms were replaced with fluorine atoms is a perfluoroalkyl. Non-limiting examples of perfluoroalkyls include trifluoromethyl and pentafluoroethyl.

The term "glycoside," as used herein, refers to a monovalent group that is a monosaccharide or sugar acid having a valency on an anomeric carbon. Non-limiting examples of monosaccharides include arabinose, xylose, fructose, galactose, glucose, ribose, tagatose, fucose, and rhamnose. Non-limiting examples of sugar acids include xylonic acid, gluconic acid, glucuronic acid, galacturonic acid, tartaric acid, saccharic acid, or mucic acid.

The term "glycosidic bond," as used herein, refers to a covalent bond between an oxygen atom and an anomeric carbon atom in a monosaccharide or sugar acid having an anomeric carbon atom.

The term "halogen," as used herein, represents a halogen selected from bromine, chlorine, iodine, and fluorine.

The term "heteroaryl," as used herein, represents a monocyclic 5-, 6-, 7-, or 8-membered ring system, or a fused or bridging bicyclic, tricyclic, or tetracyclic ring system; the ring system contains one, two, three, or four heteroatoms independently selected from the group consisting of nitrogen, oxygen, and sulfur; and at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkenyl; alkoxy; acyloxy; aryloxy; alkylsulfinyl; alkylsulfonyl; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl. Each of the substituents may itself be unsubstituted or substituted with unsubstituted substituent(s) defined herein for each respective group.

The term "heteroarylene," as used herein, is a divalent group that is a heteroaryl group, in which one hydrogen atom is replaced with a valency. Heteroarylene may be optionally substituted as described herein for heteroaryl.

The term "heteroaryloxy," as used herein, refers to a structure —OR, in which R is heteroaryl. Heteroaryloxy can be optionally substituted as defined for heteroaryl.

The term "heterocyclyl," as used herein, represents a monocyclic, bicyclic, tricyclic, or tetracyclic non-aromatic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentene ring, or another heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkenyl; alkoxy; acyloxy; alkylsulfinyl; alkylsulfonyl; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; =S; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

The term "heterocyclyl alkyl," as used herein, represents an alkyl group substituted with a heterocyclyl group. The heterocyclyl and alkyl portions of an optionally substituted heterocyclyl alkyl are optionally substituted as the described for heterocyclyl and alkyl, respectively.

The term "heterocyclylene," as used herein, represents a heterocyclyl, in which one hydrogen atom is replaced with a valency. An optionally substituted heterocyclylene is a heterocyclylene that is optionally substituted as described herein for heterocyclyl.

The term "heterocyclyloxy," as used herein, refers to a structure —OR, in which R is heterocyclyl. Heterocyclyloxy can be optionally substituted as described for heterocyclyl.

The terms "hydroxyl" and "hydroxy," as used interchangeably herein, represent —OH. A hydroxyl substituted with an acyl is an acyloxy. A protected hydroxyl is a hydroxyl, in which the hydrogen atom is replaced with an O-protecting group.

The term "hydroxyalkyl," as used herein, refers to a C1-6 alkyl group that is substituted with one or more hydroxyls, provided that each carbon atom in the hydroxyalkyl is attached either to no more than one hydroxyl. Non-limiting examples of hydroxyalkyls include hydroxymethyl, 2-hydroxyethyl, and 1-hydroxyethyl.

The term "hydroxycinnamic acid," as used herein, refers to a cinnamic acid having one, two, or three hydroxyls attached to the phenyl ring of the hydroxycinnamic acid. A non-limiting example of the hydroxycinnamic acid is caffeic acid.

The term "modulating," as used herein, refers to an observable change in the level of a marker in a subject, as measured using techniques and methods known in the art for the measurement of the marker. Modulating the marker level in a subject may result in a change of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 9 or at least 98% or more relative to prior to administration; e.g., up to 100% relative to prior to administration). In some embodiments, modulating is increasing the level of a marker in a subject. Increasing the marker level in a subject may result in an increase of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In other embodiments, modulating is decreasing the level of a marker in a subject. Decreasing the marker level in a subject may result in a decrease of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In embodiments in which a parameter is increased or decreased (or reduced) in a subject following a step of administering a composition described herein, the increase or decrease may take place and/or be detectable within a range of time following the administration (e.g., within six hours, 24 hours, 3 days, a week or longer), and may take place and/or be detectable after one or more administrations (e.g., after 2, 3, 4, 5, 6, 7, 8, 9, 10 or more administrations, e.g., as part of a dosing regimen for the subject).

The term "oxo," as used herein, represents a divalent oxygen atom (e.g., the structure of oxo may be shown as =O).

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Principles for preparing pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable electrophile. Representative counterions useful for pharmaceutically acceptable salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, bromide, chloride, iodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

The term "phenolic oxygen atom," as used herein, refers to a divalent oxygen atom within the structure of a compound, where at least one valency of the phenolic oxygen atom is bonded to an sp2-hybridized carbon atom within an aromatic ring.

The term "physiological conditions," as used herein, refers to the conditions prevalent in vivo. For example, incubation in simulated gastric fluid (SGF) or simulated intestinal fluid (SIF) at physiologically relevant temperatures (e.g., about 36-37° C.) may be used to simulate physiological conditions representative of a stomach or upper intestine, respectively. Colon conditions may be simulated using a slurry of a healthy human fecal matter under anaerobic conditions.

The term "prevent," as used herein in reference to the medical effect of a compound of the disclosure on a subject, refers to minimizing or partially or completely inhibiting the development of the associated disease, disorder, or condition. Non-limiting examples of the disease, disorder, or condition are those described herein.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3rd Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "subject," as used herein, represents a human or non-human animal (e.g., a mammal) that is suffering from, or is at risk of, disease, disorder, or condition, as determined by a qualified professional (e.g., a doctor or a nurse practitioner) with or without known in the art laboratory test(s) of sample(s) from the subject. Non-limiting examples of diseases, disorders, and conditions include those described herein.

The term "sugar acid," as used herein, refers to a monosaccharide, in the linear form of which, one or both terminal positions are oxidized to a carboxylic acid. There are four classes of sugar acids: aldonic acid, ulosonic acid, uronic acid, and aldaric acid. Any of the four sugar acid classes may be used in conjugates disclosed herein. Non-limiting examples of sugar acids include xylonic acid, gluconic acid, glucuronic acid, galacturonic acid, tartaric acid, saccharic acid, or mucic acid.

The term "sugar acid acyl," as used herein, refers to a monovalent group that is a sugar acid having a carboxylate, in which —OH is replaced with a valency.

The term "thioalkenyl," as used herein, represents a group —SR, where R is alkenyl. An optionally substituted thioalkenyl is thioalkenyl that is optionally substituted as described herein for alkenyl.

The term "thioalkyl," as used herein, represents a group —SR, where R is alkyl. An optionally substituted thioalkyl is thioalkyl that is optionally substituted as described herein for alkyl.

The term "thioaryl," as used herein, represents a group —SR, where R is aryl. An optionally substituted thioaryl is thioaryl that is optionally substituted as described herein for aryl.

"Treatment" and "treating," as used herein, refer to the medical management of a subject with the intent to improve, ameliorate, stabilize, or cure a disease, disorder, or condition. This term includes active treatment (treatment directed to improve the disease, disorder, or condition); causal treatment (treatment directed to the cause of the associated disease, disorder, or condition); palliative treatment (treatment designed for the relief of symptoms of the disease, disorder, or condition); and supportive treatment (treatment employed to supplement another therapy).

The compounds described herein, unless otherwise noted, encompass isotopically enriched compounds (e.g., deuterated compounds), tautomers, and all stereoisomers and conformers (e.g. enantiomers, diastereomers, E/Z isomers, atropisomers, etc.), as well as racemates thereof and mixtures of different proportions of enantiomers or diastereomers, or mixtures of any of the foregoing forms as well as salts (e.g., pharmaceutically acceptable salts).

Other features and advantages of the disclosure will be apparent from the disclosure.

The present disclosure provides compounds, pharmaceutical compositions, and methods of their use. The compounds of the disclosure may target the production of pathogenic metabolites by certain bacteria in a subject, thereby reducing the pathogenic metabolite levels in the subject.

The compounds of the disclosure may be a conjugate of the disclosure, e.g., those compounds including a glycoside or an acylated sugar. Upon administration of the conjugate of the disclosure, the conjugate may be cleaved in vivo to remove the glycoside or an acylated sugar from the compound and to release the corresponding unconjugated compound of the disclosure. Conjugates of the disclosure may be advantageous in therapeutic applications benefitting from a particular tissue-targeted delivery of an unconjugated compound of the disclosure.

Compounds of the disclosure that include at least one glycoside or at least one acylated sugar are conjugates.

Compounds having a fatty acid acyl (e.g., a short chain fatty acid acyl) attached through an ester bond are also conjugates.

Acylated sugars that may be used in the conjugates disclosed herein include an acyl (e.g., a fatty acid acyl) and a core selected from the group consisting of a carbohydrate (e.g., a monosaccharide), sugar acid, and sugar alcohol. For example, an acylated sugar may be a monovalent group of formula (III):

(III)

wherein
L is a bond to a pharmaceutically active agent, a carbonate linker, or a carbamate linker;
group A is a core selected from the group consisting of carbohydrate (e.g., a monosaccharide), sugar acid, and sugar alcohol;
each R is independently an acyl bonded to an oxygen atom in group A; and
m is an integer from 0 to the total number of available hydroxyl groups in group A (e.g., 1, 2, 3, 4, or 5).

In some embodiments, L may be attached to a carbon atom in group A (e.g., an anomeric carbon atom or a carbonyl carbon atom). In some embodiments, L may be attached to an oxygen atom in group A (e.g., an alcoholic oxygen atom, a phenolic oxygen atom, or a carboxylate oxygen atom).

In some embodiments, at least one R is a fatty acid acyl.

In some embodiments, the fatty acid(s) are short chain fatty acid acyls. In some embodiments, the short chain fatty acid acyl is a $C_{3-6}$ short chain fatty acid acyl (e.g., propionyl or butyryl).

In some embodiments, the acylated sugar is peracylated, i.e., all of the available hydroxyls in the acylated sugar are substituted with an acyl.

A monosaccharide may be, e.g., arabinose, xylose, fructose, galactose, glucose, ribose, tagatose, fucose, or rhamnose. In some embodiments, the monosaccharide is L-arabinose, D-xylose, fructose, galactose, D-glucose, D-ribose, D-tagatose, L-fucose, or L-rhamnose (e.g., the monosaccharide is D-xylose). A sugar acid may be, e.g., aldonic acid, ulosonic acid, uronic acid, or aldaric acid. A sugar acid may be, e.g., xylonic acid, gluconic acid, glucuronic acid, galacturonic acid, tartaric acid, saccharic acid, or mucic acid. A sugar alcohol may be, e.g., glycerol, erythritol, threitol, arabitol, xylitol, tibitol, mannitol, sorbitol, galactitol, fucitol, iditol, or inositol.

An acylated sugar may be covalently linked to a pharmaceutically active agent through a carbon-oxygen bond that is cleavable in vivo, a carbonate linker, or a carbamate linker. The carbon-oxygen bond may be, e.g., a glycosidic bond or ester bond. Acylated sugars having a monosaccharide or a sugar acid as a core may be covalently linked to a pharmaceutically active agent through a carbon-oxygen bond that is cleavable in vivo (e.g., a glycosidic bond or ester bond), a carbonate linker, or a carbamate linker. In the sugar acid core, one or both carboxylates may be present as O-protected versions (e.g., as alkyl esters (e.g., methyl or ethyl esters)). Acylated sugars having a sugar alcohol as a core may be covalently linked to a pharmaceutically active agent through a carbon-oxygen bond that is cleavable in vivo (e.g., an ester bond), a carbonate linker, or a carbamate linker.

Non-limiting examples of acylated sugars are:

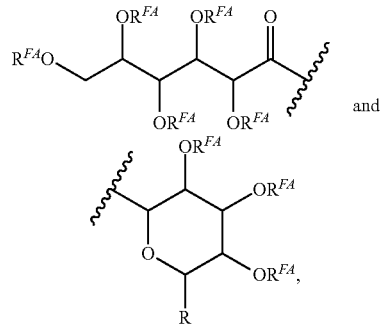

wherein
R is H, —$CH_3$, or —$CH_2OR^{FA}$; and
each $R^{FA}$ is independently H or a fatty acid acyl (e.g., a short chain fatty acid acyl);
provided that at least one $R^{FA}$ is a fatty acid acyl (e.g., a short chain fatty acid acyl).

In some embodiments, the disclosure provides a compound of formula (I):

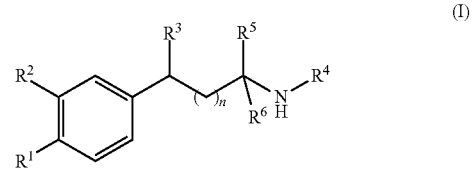

(I)

or a pharmaceutically acceptable salt thereof,
wherein
n is 0 or 1;
$R^1$ is H or —$OR^A$, wherein $R^A$ is H, —$C(O)C_{1-6}$ alkyl, or an acylated sugar;
$R^2$ is H, halogen, amino, $C_{1-6}$ alkyl, or —$OR^A$, wherein $R^A$ is H or an acylated sugar;
$R^3$ is H, a halogen, —OH, or $C_{1-6}$ alkyl optionally substituted with one or more halogens;
$R^4$ is H, —$NH_2$, —$C(O)OCH_3$, or an acylated sugar;
$R^5$ is H, —C(O)OH, —$C(O)OC_{1-6}$ alkyl, —C(O)Oglycoside, —C(O)NHOH, or —C(O)O(acylated sugar); and
$R^6$ is H, halogen, or optionally substituted $C_{1-6}$ alkyl;
provided that at least one $R^A$ is present; or provided that $R^3$ and/or $R^6$ comprise a halogen.

In some embodiments, the compound of formula (I) is a compound of formula (I-a):

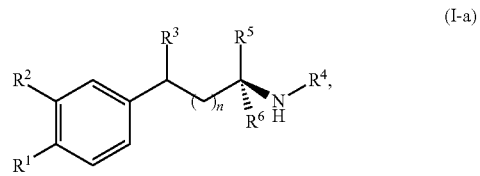

(I-a)

or a pharmaceutically acceptable salt thereof.

In some embodiments, the compound of formula (I) is a compound of formula (II):

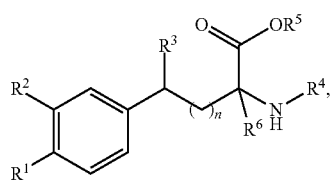

(II)

or a pharmaceutically acceptable salt thereof,
where
n is 0 or 1;
each of $R^1$ and $R^2$ is independently H or —$OR^4$, wherein each $R^4$ is independently H or an acylated sugar, or $R^1$ is —$C(O)C_{1-6}$ alkyl;
$R^3$ is H or a halogen;
$R^4$ is H, —$NH_2$, —$C(O)OCH_3$, or an acylated sugar;
$R^5$ is H, alkyl, glycoside, or an acylated sugar; and
$R^6$ is H or optionally substituted alkyl;
provided that at least one $R^4$ is present; or provided that $R^3$ and/or $R^6$ comprise a halogen.

In some embodiments, the compound is a compound of formula (II-a):

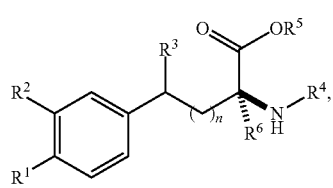

(II-a)

or a pharmaceutically acceptable salt thereof.

In some embodiments, R is H. In some embodiments, R is methyl.

In some embodiments, $R^1$ is H or —OH. In some embodiments, $R^1$ is H. In some embodiments, $R^1$ is —OH. In some embodiments, $R^1$ is —$OC(O)C_{1-6}$ alkyl. In some embodiments, $R^1$ is —$OC(O)CH_3$. In some embodiments, $R^1$ is —$OC(O)CH_2CH_3$. In some embodiments, $R^1$ is —$OC(O)CH_2CH_2CH_3$. In some embodiments, $R^1$ is —O(acylated sugar).

In some embodiments, $R^1$ is —OH and $R^2$ is H. In some embodiments, $R^1$ is —OH and $R^2$ is H.

In some embodiments, $R^1$ is —OH and $R^2$ is H. In some embodiments, $R^1$ is —OH $R^2$ is a halogen.

In some embodiments, $R^2$ is an amino. In some embodiments, $R^2$ is $C_{1-6}$ alkyl. In some embodiments, $R^2$ is methyl.

In some embodiments, $R^3$ is H. In some embodiments, $R^3$ is a halogen. In some embodiments, $R^3$ is fluoro or chloro. In some embodiments, $R^3$ is OH. In some embodiments, $R^3$ is a $C_{1-6}$ alkyl optionally substituted with one or more halogens. In some embodiments, $R^3$ is methylene optionally substituted with one or more halogens. In some embodiments, $R^3$ is methyl.

In some embodiments, $R^4$ is H. In some embodiments, $R^4$ is —$NH_2$.

In some embodiments, $R^5$ is —$C(O)OH$. In some embodiments, $R^5$ is —$C(O)O$acylated sugar. In some embodiments, $R^5$ is H. In some embodiments, $R^5$ is —$C(O)OC_{1-6}$ alkyl. In some embodiments, $R^5$ is —$C(O)OCH_3$. In some embodiments, $R^5$ is $C(O)O$glycoside. In some embodiments, $R^5$ is $C(O)NHOH$.

In some embodiments, $R^6$ is H. In some embodiments, $R^6$ is a $C_{1-6}$ alkyl. In some embodiments, $R^6$ is a $C_{1-6}$ alkyl substituted with one, two, or three halogens. In some embodiments, $R^6$ is a $C_{1-6}$ alkyl substituted with one, two, or three fluorine atoms. In some embodiments, $R^6$ is a halogen. In some embodiments, $R^6$ is methyl. In some embodiments, $R^6$ is ethyl.

In some embodiments, n is 0. In some embodiments, n is 1.

In some embodiments, the disclosure provides compounds of formula (I) and pharmaceutically acceptable salts thereof, wherein
n is 0;
$R^1$ is —OH;
$R^2$ is halogen;
$R^3$ is H, a halogen, or —OH, $C_{1-6}$ alkyl optionally substituted with one or more halogens;
$R^4$ is H, —$NH_2$, or an acylated sugar;
$R^5$ is H, —$C(O)OH$, —$C(O)OC_{1-6}$ alkyl, —$C(O)O$glycoside, —$C(O)NHOH$, or —$C(O)O$(acylated sugar); and
$R^6$ is H or optionally substituted $C_{1-6}$ alkyl.

In some embodiments,
n is 0;
$R^1$ is —OH;
$R^2$ is halogen;
$R^3$ is H;
$R^4$ is H;
$R^5$ is —$C(O)OH$; and
$R^6$ is optionally substituted alkyl. In some embodiments, $R^6$ is methylene substituted with one or more halogens or hydroxy. In some embodiments, the compounds of the present disclosure include

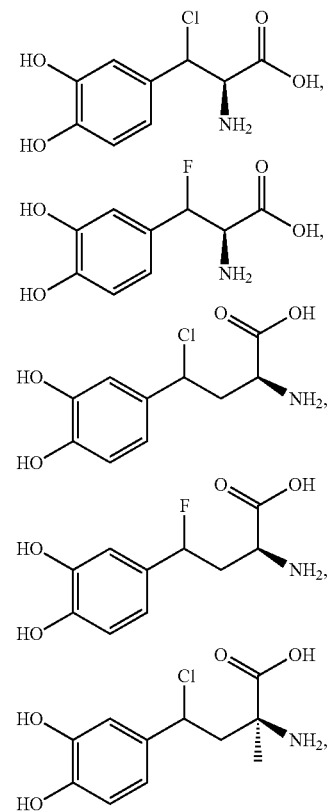

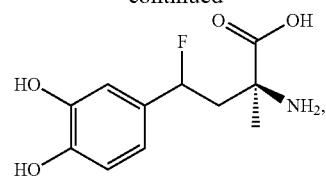
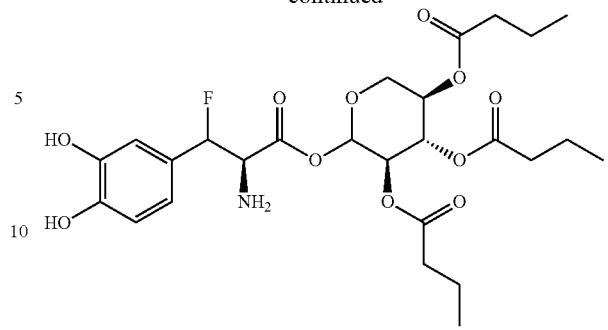
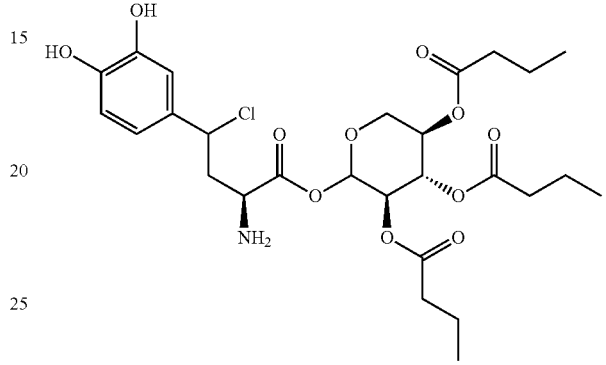
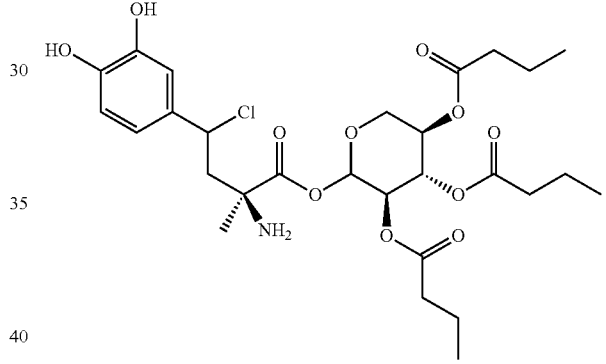
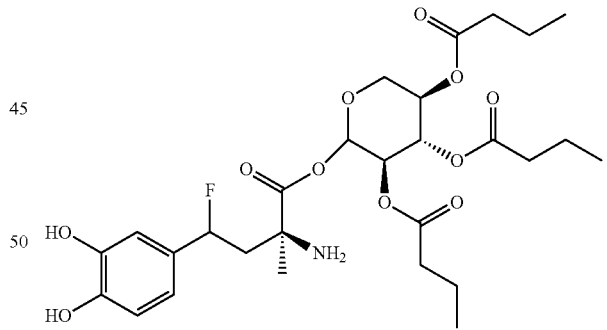
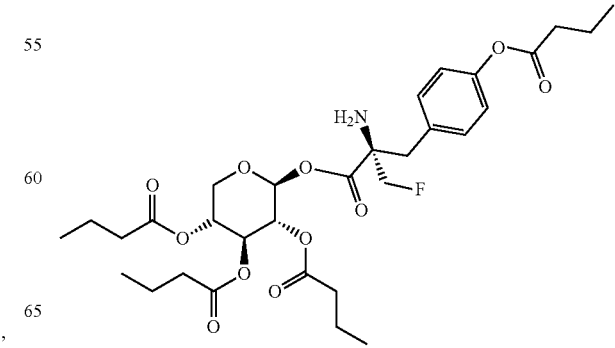

25
-continued
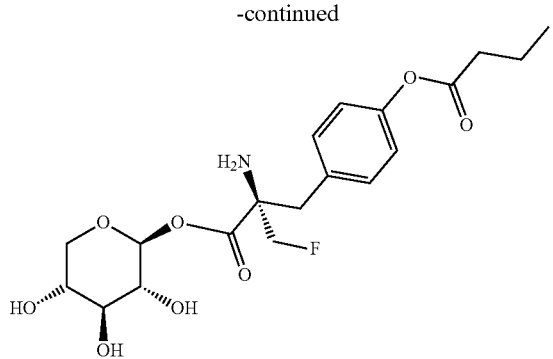
,
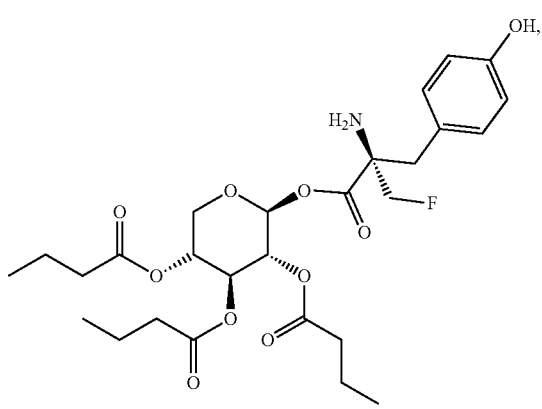
,
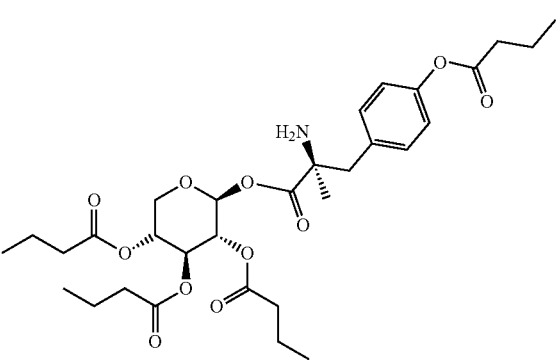
,
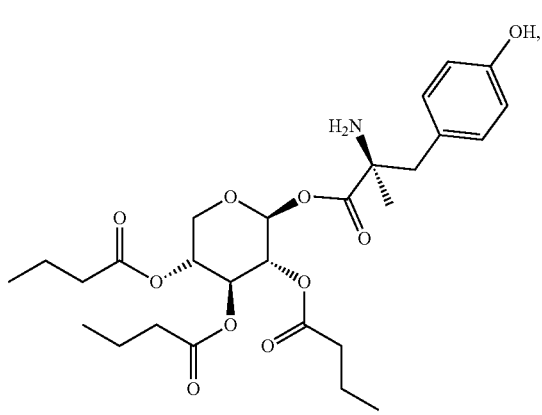
,
26
-continued
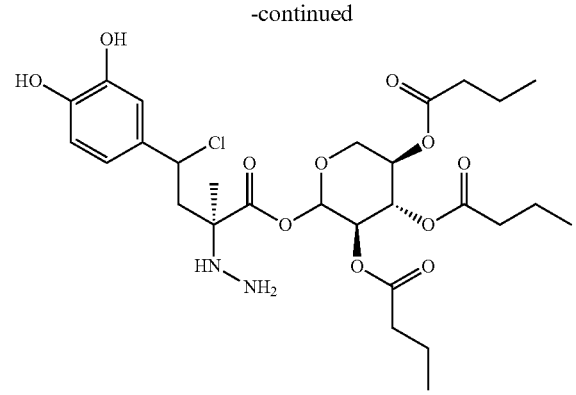
,
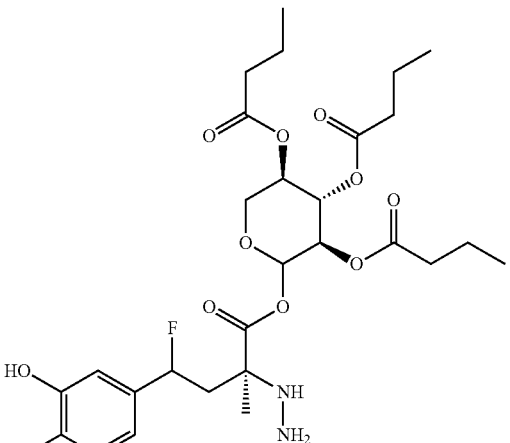
and pharmaceutically acceptable salts thereof.
In some embodiments, the compounds of the present disclosure include:

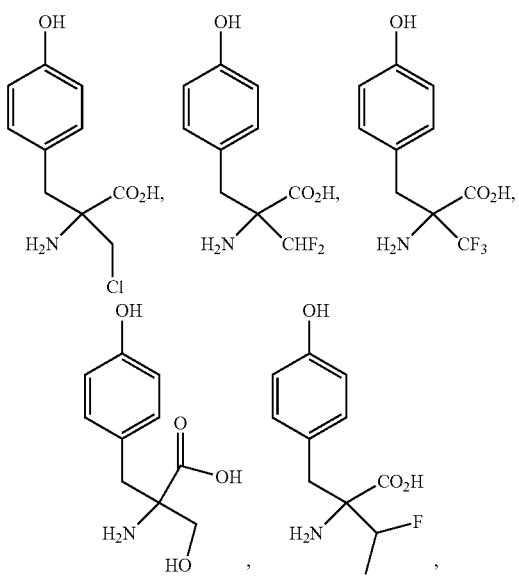
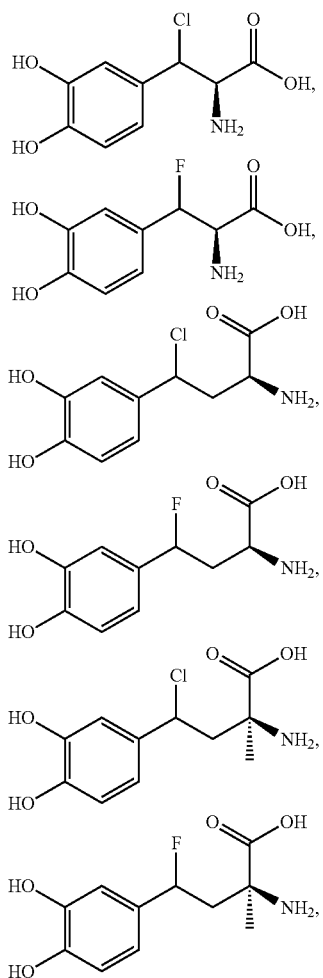
and pharmaceutically acceptable salts thereof. In some embodiments, the compounds of the present disclosure include:
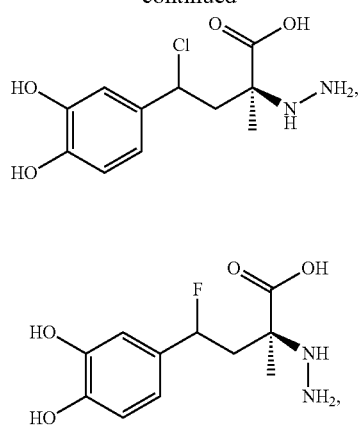
and pharmaceutically acceptable salts thereof. In some embodiments, the compounds of the present disclosure include:
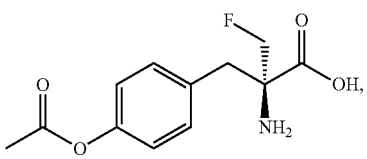
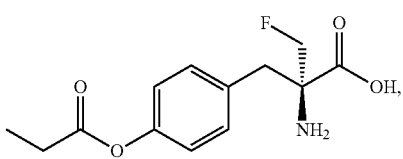
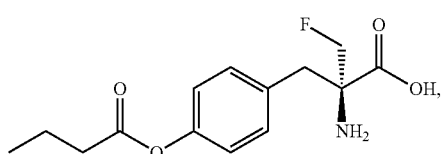
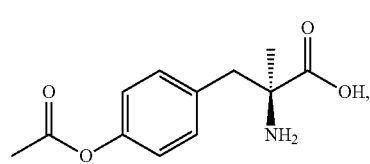
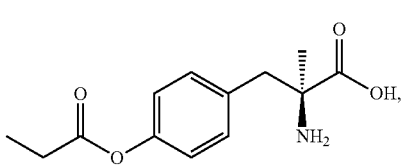
and pharmaceutically acceptable salts thereof. In some embodiments, the compounds of the present disclosure include:

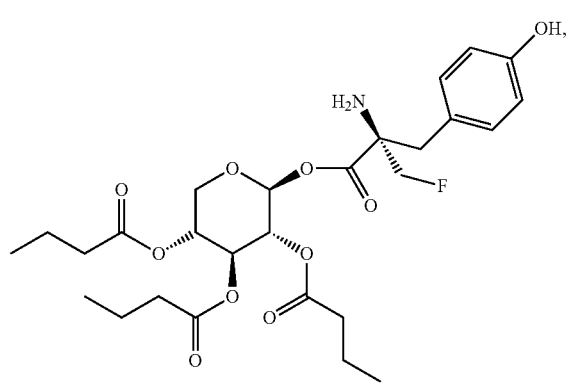
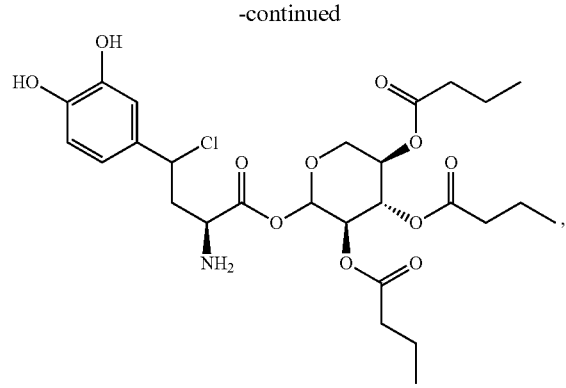
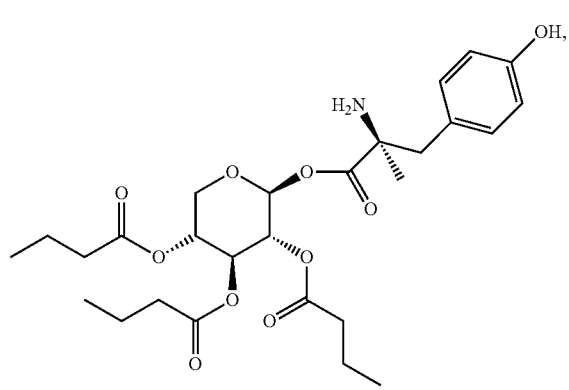
and pharmaceutically acceptable salts thereof. In some embodiments, the compounds of the present disclosure include:
and pharmaceutically acceptable salts thereof. In some embodiments, the compounds of the present disclosure include:
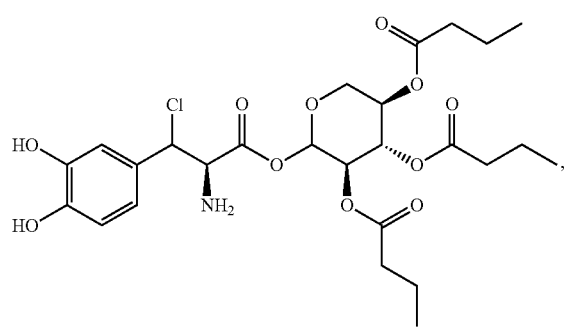
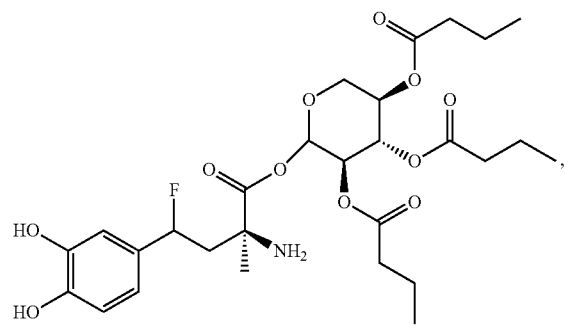
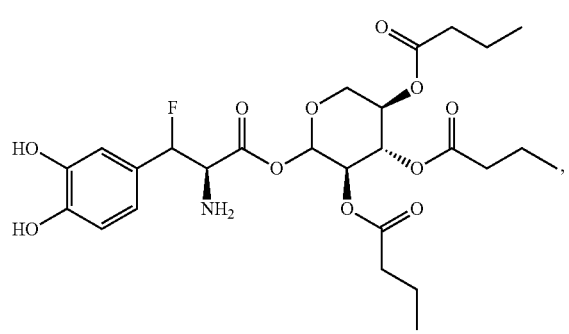
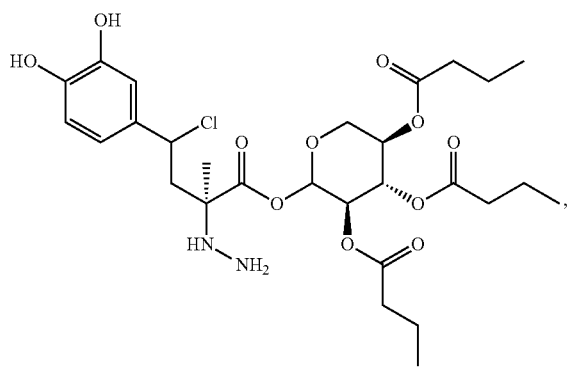

-continued
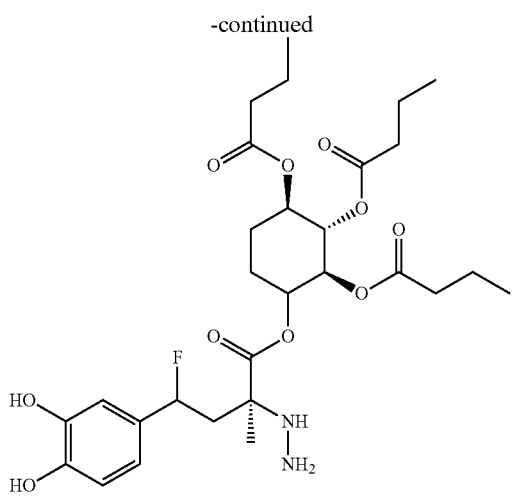
and pharmaceutically acceptable salts thereof. In some embodiments, the compounds of the present disclosure include:
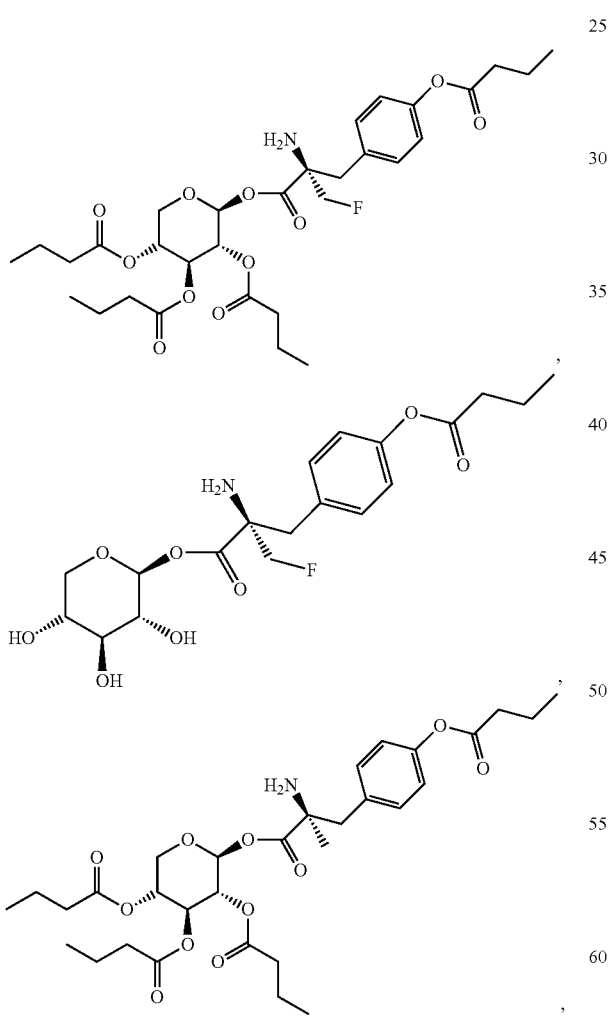
and pharmaceutically acceptable salts thereof.
In some embodiments, the compounds of the present disclosure include
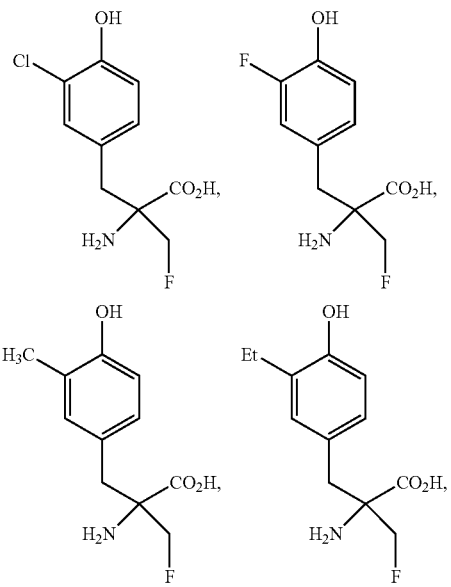 [SMILES: NC(CF)(Cc1ccc(O)c(Cl)c1)C(=O)O ; NC(CF)(Cc1ccc(O)c(F)c1)C(=O)O ; Cc1cc(CC(N)(CF)C(=O)O)ccc1O ; CCc1cc(CC(N)(CF)C(=O)O)ccc1O]
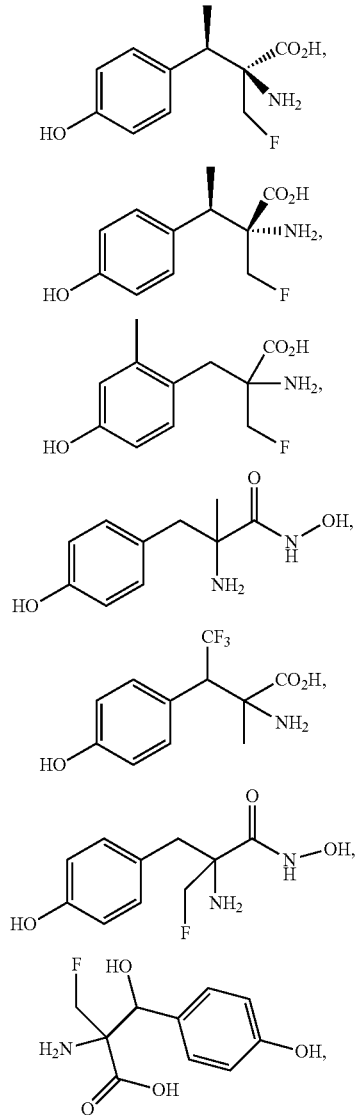

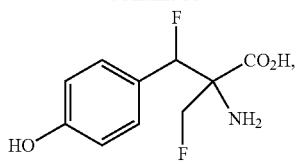
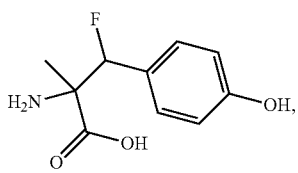
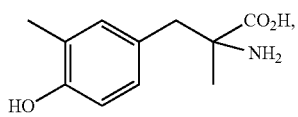
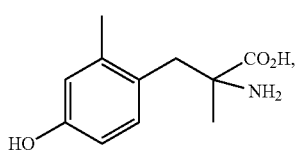
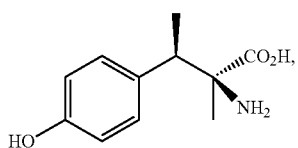
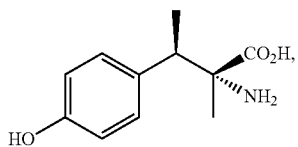
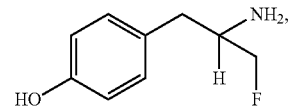
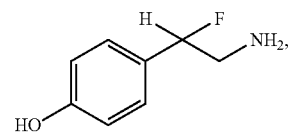
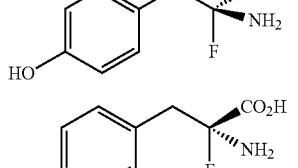
and pharmaceutically acceptable salts thereof.
In some embodiments, the compounds of the present disclosure include
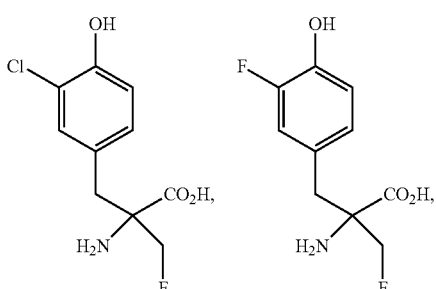
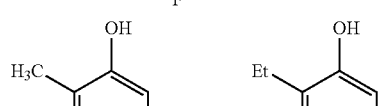
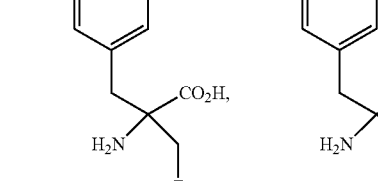
and pharmaceutically acceptable salts thereof. In some embodiments, the compounds of the present disclosure include
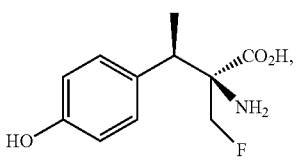
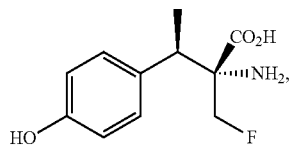
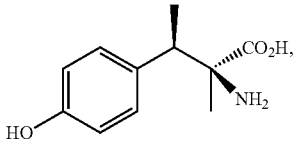
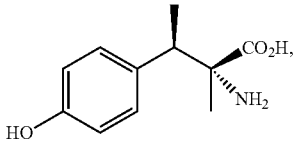
and pharmaceutically acceptable salts thereof. In some embodiments, the compounds of the present disclosure include
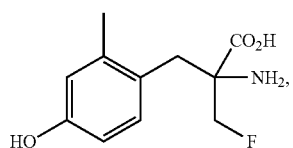

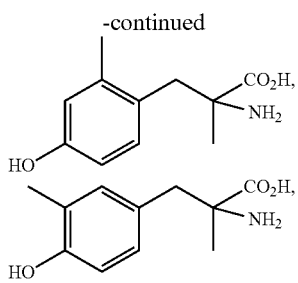

and pharmaceutically acceptable salts thereof. In some embodiments, the compounds of the present disclosure include

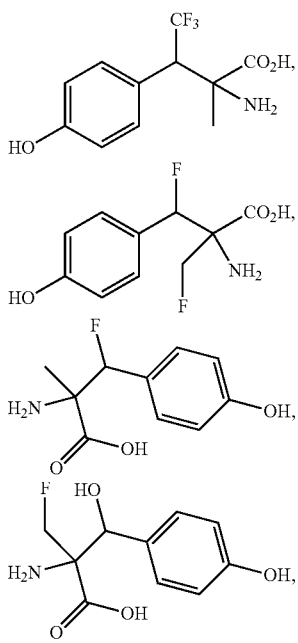

and pharmaceutically acceptable salts thereof. In some embodiments, the compounds of the present disclosure include

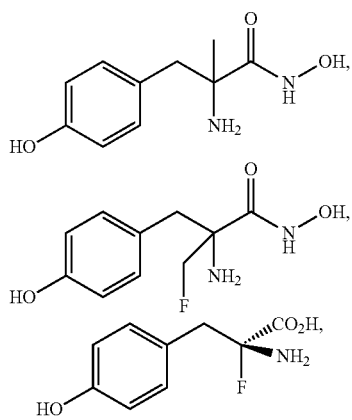

and pharmaceutically acceptable salts thereof. In some embodiments, the compounds of the present disclosure include

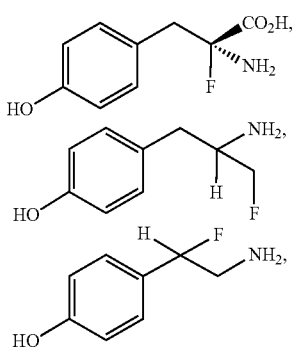

and pharmaceutically acceptable salts thereof.

When the compounds of the present disclosure comprise at least one glycoside or acylated sugar, the compound is a conjugate. These conjugates can be advantageous for targeted delivery to a tissue having the highest abundance of tyrosine decarboxylase from *Enterococcus faecalis*. Tyrosine decarboxylase from *Enterococcus faecalis* can convert L-DOPA to L-dopamine. Consumption of L-DOPA may reduce its effectiveness as a treatment for Parkinson's disease and introduce a host of side effects to the subject, including dyskinesias, nausea, vomiting, depression, and heart arrhythmias.

Consumption of L-DOPA by tyrosine decarboxylase may be inhibited using the compounds described above. Accordingly, a method of inhibiting a tyrosine decarboxylase-mediated conversion of a L-DOPA to L-dopamine includes contacting the tyrosine decarboxylase with the compound described above.

Inhibition of tyrosine decarboxylase may lead to the modulation of tyrosine decarboxylase markers. Accordingly, a method of modulating a tyrosine decarboxylase marker in a subject in need thereof includes administering to the subject in need thereof a therapeutically effective amount of the compound described above (e.g., as a pharmaceutical composition). The tyrosine decarboxylase marker can be, e.g., L-DOPA levels. The amount of L-DOPA can be increased in accordance with the methods of the disclosure.

Parkinson's disease can be treated using the compounds disclosed herein. Accordingly, a method of treating Parkinson's disease comprises administering to a subject in need thereof a therapeutically effective amount of at least one compound of the present disclosure or a pharmaceutically acceptable salt thereof. For example, a method of treating or preventing a disease associated with the tyrosine decarboxylase activity in a subject in need thereof includes administering a therapeutically effective amount of at least one compound of the present disclosure or a pharmaceutically acceptable salt thereof (e.g., as a pharmaceutical composition). The disease associated with the tyrosine decarboxylase activity may be, e.g., Parkinson's disease. In some embodiments, a therapeutically effective amount of a second compound is concurrently administered. In some embodiments the second compound is L-DOPA or levodopa. In some embodiments, a therapeutically effective amount of a third compound is concurrently administered. In some embodiments, the third compound is carbidopa.

The compounds disclosed herein may be formulated into pharmaceutical compositions for administration to human subjects in a biologically compatible form suitable for administration in vivo. Pharmaceutical compositions typically include a compound as described herein and a physiologically acceptable excipient (e.g., a pharmaceutically acceptable excipient).

The compound described herein can also be used in the form of the free acid/base, in the form of salts, zwitterions, or as solvates. All forms are within the scope of the disclosure. The compounds, salts, zwitterions, solvates, or pharmaceutical compositions thereof, may be administered to a subject in a variety of forms depending on the selected route of administration, as will be understood by those skilled in the art. The compounds described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, a compound disclosed herein can be administered alone or in admixture with a pharmaceutical carrier selected regarding the intended route of administration and standard pharmaceutical practice. Pharmaceutical compositions for use in accordance with the present disclosure thus can be formulated in a conventional manner using one or more physiologically acceptable carriers having excipients and auxiliaries that facilitate processing of compounds disclosed herein into preparations which can be used pharmaceutically.

This disclosure also includes pharmaceutical compositions which can contain one or more physiologically acceptable carriers. In making the pharmaceutical compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in Remington: The Science and Practice of Pharmacy, 21st Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in Handbook of Pharmaceutical Excipients, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 21st Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the compounds can be milled to provide the appropriate particle size prior to combining with the other ingredients. If the compound is substantially insoluble, it can be milled to a particle size of less than 200 mesh. If the compound is substantially water soluble, the particle size can be adjusted by milling to provide a substantially uniform distribution in the formulation, e.g., about 40 mesh.

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the subject to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound disclosed herein will be that amount of the compound that is the lowest dose effective to produce a therapeutic effect. Such an effective dose will generally depend upon the factors described above.

A compound disclosed herein may be administered to the subject in a single dose or in multiple doses. When multiple doses are administered, the doses may be separated from one another by, for example, 1-24 hours, 1-7 days, or 1-4 weeks. The compound may be administered according to a schedule, or the compound may be administered without a predetermined schedule. It is to be understood that, for any particular subject, specific dosage regimes should be adjusted over time according to the individual need and the professional judgment of the person administering or supervising the administration of the compositions.

The compounds may be provided in a dosage form. In some embodiments, the unit dosage form may be an oral unit dosage form (e.g., a tablet, capsule, suspension, liquid solution, powder, crystals, lozenge, sachet, cachet, elixir, syrup, and the like) or a food product serving (e.g., the active agents may be included as food additives or dietary ingredients). In some embodiments, the dosage form is designed for administration of at least one compound disclosed herein, where the total amount of an administered compound is from 0.1 g to 10 g (e.g., 0.5 g to 9 g, 0.5 g to 8 g, 0.5 g to 7 g, 0.5 g to 6 g, 0.5 g to 5 g, 0.5 g to 1 g, 0.5 g to 1.5 g, 0.5 g to 2 g, 0.5 g to 2.5 g, 1 g to 1.5 g, 1 g to 2 g, 1 g to 2.5 g, 1.5 g to 2 g, 1.5 g to 2.5 g, or 2 g to 2.5 g). In other embodiments, the compound is consumed at a rate of 0.1 g to 10 g per day (e.g., 0.5 g to 9 g, 0.5 g to 8 g, 0.5 g to 7 g, 0.5 g to 6 g, 0.5 g to 5 g, 0.5 g to 1 g per day, 0.5 g to 1.5 g per day, 0.5 g to 2 g per day, 0.5 g to 2.5 g per day, 1 g to 1.5 g per day, 1 g to 2 g per day, 1 g to 2.5 g per day, 1.5 g to 2 g per day, 1.5 g to 2.5 g per day, or 2 g to 2.5 g per day) or more. The attending physician ultimately will decide the appropriate amount and dosage regimen, an effective amount of the compound disclosed herein may be, for example, a total daily dosage of, e.g., between 0.5 g and 5 g (e.g., 0.5 to 2.5 g) of any of the compound described herein. Alternatively, the dosage amount can be calculated using the body weight of the subject. When daily dosages exceed 5 g/day, the dosage of the compound may be divided across two or three daily administration events.

In the methods of the disclosure, the time period during which multiple doses of a compound disclosed herein are administered to a subject can vary. For example, in some embodiments doses of the compounds are administered to a subject over a time period that is 1-7 days; 1-12 weeks; or 1-3 months. In other embodiments, the compounds are administered to the subject over a time period that is, for example, 4-11 months or 1-30 years. In yet other embodiments, the compounds disclosed herein are administered to a subject at the onset of symptoms. In any of these embodiments, the amount of the compound that is administered may vary during the time period of administration. When a compound is administered daily, administration may occur, for example, 1, 2, 3, or 4 times per day.

A compound described herein may be administered to a subject with a pharmaceutically acceptable diluent, carrier, or excipient, in unit dosage form. Conventional pharmaceutical practice may be employed to provide suitable formulations or compositions to administer the compound to subjects suffering from a disorder. Administration may begin before the subject is symptomatic.

Exemplary routes of administration of the compounds disclosed herein or pharmaceutical compositions thereof, used in the present disclosure include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The compounds desirably are administered with a physiologically acceptable carrier (e.g., a pharmaceutically acceptable carrier). Pharmaceutical formulations of the compounds described herein formulated for treatment of the disorders described herein are also part of the present disclosure. In some embodiments, the compounds disclosed herein are administered to a subject orally. In some embodiments, the compounds disclosed herein are administered to a subject topically.

The pharmaceutical compositions contemplated by the disclosure include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with physiologically acceptable excipients (e.g., pharmaceutically acceptable excipients). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other physiologically acceptable excipients (e.g., pharmaceutically acceptable excipients) can be colorants, flavoring agents, plasticizers, humectants, buffering agents, and the like.

Formulations for oral administration may also be presented as chewable tablets, as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present disclosure can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Dosages for buccal or sublingual administration typically are 0.1 to 500 mg per single dose as required. In practice, the physician determines the actual dosing regimen which is most suitable for an individual subject, and the dosage varies with the age, weight, and response of the particular subject. The above dosages are exemplary of the average case, but individual instances exist where higher or lower dosages are merited, and such are within the scope of this disclosure.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound disclosed herein with a pharmaceutically acceptable carrier. In some embodiments, the pharmaceutically acceptable carrier is a liquid, e.g., alcohol, water, polyethylene glycol, or a perfluorocarbon. Optionally, another material may be added to alter the aerosol properties of the solution or suspension of compounds disclosed herein. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., U.S. Pat. Nos. 5,112,598 and 5,556,611, each of which is herein incorporated by reference).

The compounds may also be formulated for nasal administration. Compositions for nasal administration also may conveniently be formulated as aerosols, drops, gels, and powders. The formulations may be provided in a single or multidose form. In the case of a dropper or pipette, dosing may be achieved by the subject administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compounds for nasal or inhalation administration will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the compound in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

The compounds described herein for use in the methods of the disclosure can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. For example, to prepare such a composition, the compounds disclosed herein may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., a compound disclosed herein or a solution thereof);

(2) "Drug for Injection:" the drug substance (e.g., a compound disclosed herein) as a dry solid that will be combined with the appropriate sterile vehicle for parenteral administration as a drug injection;

(3) "Drug Injectable Emulsion:" a liquid preparation of the drug substance (e.g., a compound disclosed herein) that is dissolved or dispersed in a suitable emulsion medium;

(4) "Drug Injectable Suspension:" a liquid preparation of the drug substance (e.g., a compound disclosed herein) suspended in a suitable liquid medium; and (5) "Drug for Injectable Suspension:" the drug substance (e.g., a compound disclosed herein) as a dry solid that will be combined with the appropriate sterile vehicle for parenteral administration as a drug injectable suspension.

Exemplary formulations for parenteral administration include solutions of the compounds prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 21st Ed., Gennaro, Ed., Lippencott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds or biologically active agents within the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

Non-limiting embodiments of the present disclosure include the following:

1. A compound chosen from the following compounds

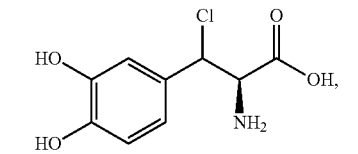

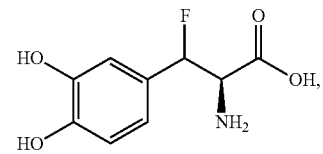

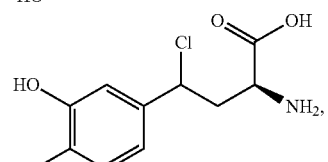

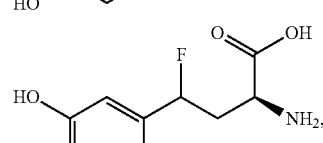

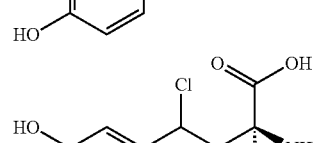

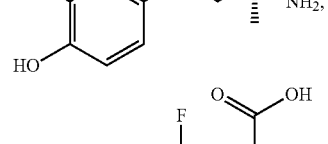

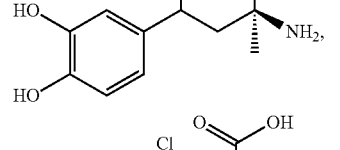

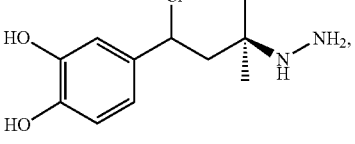

-continued

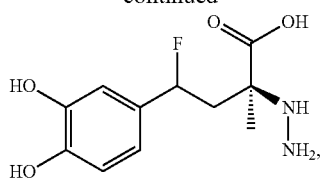

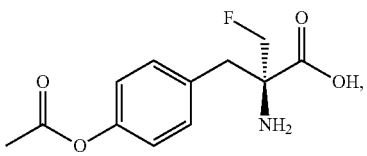

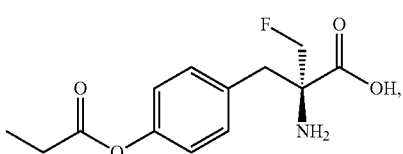

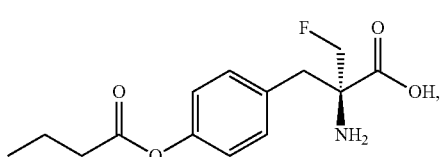

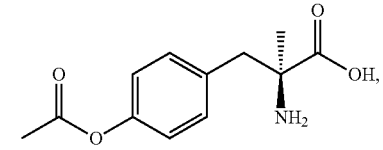

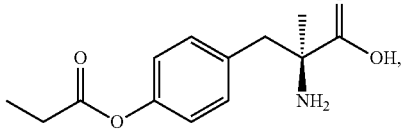

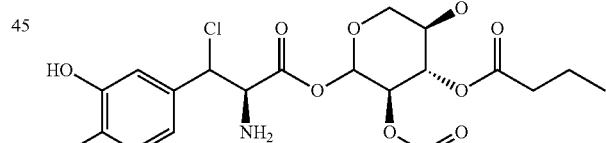

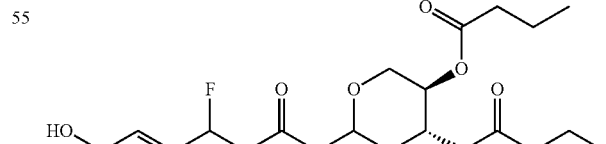

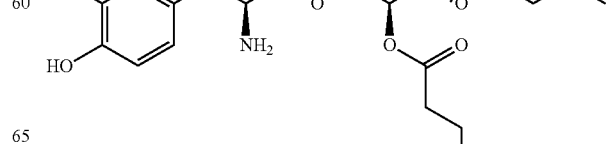

45
-continued
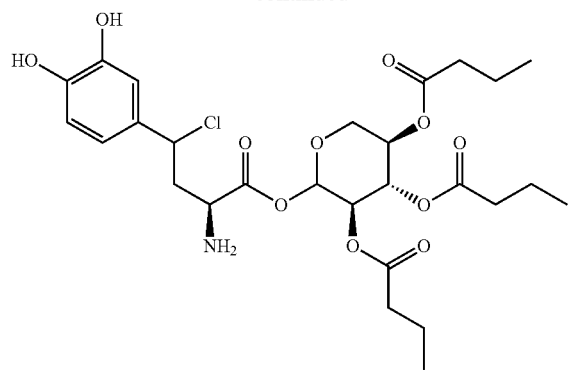
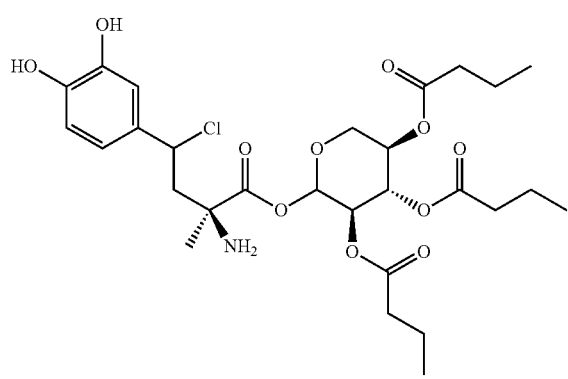
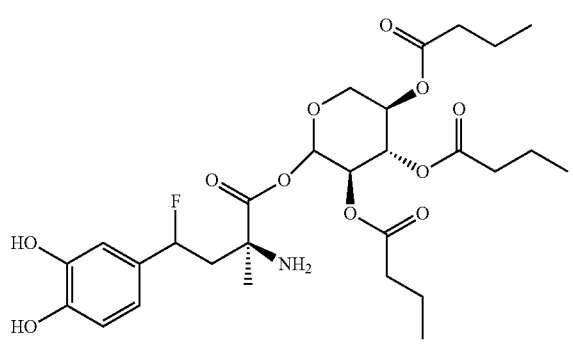
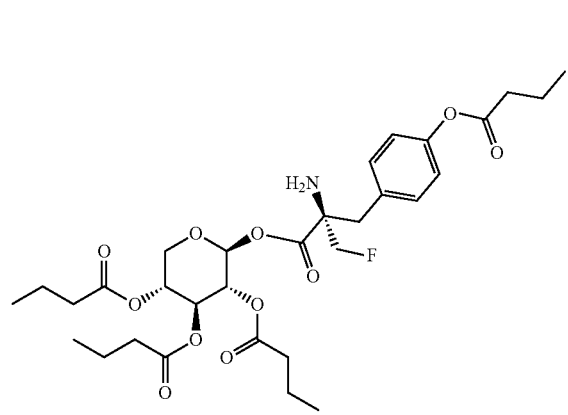
46
-continued
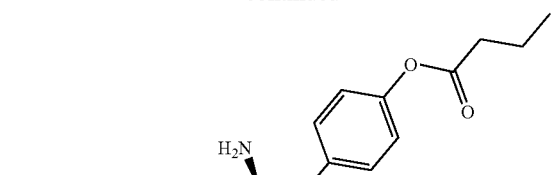
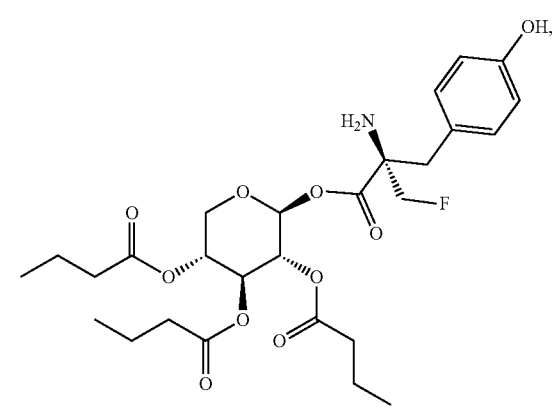
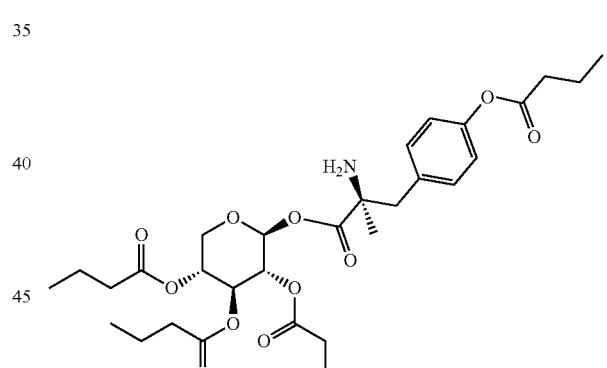
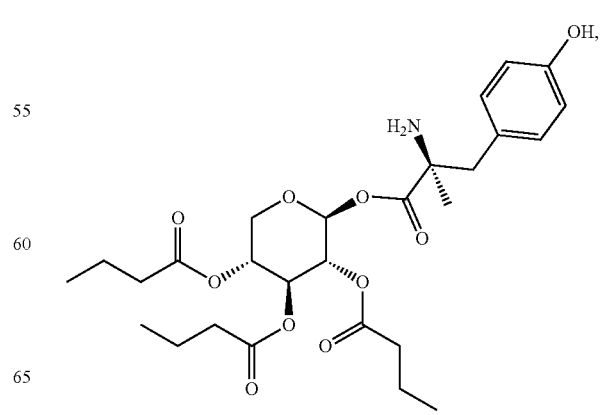

-continued
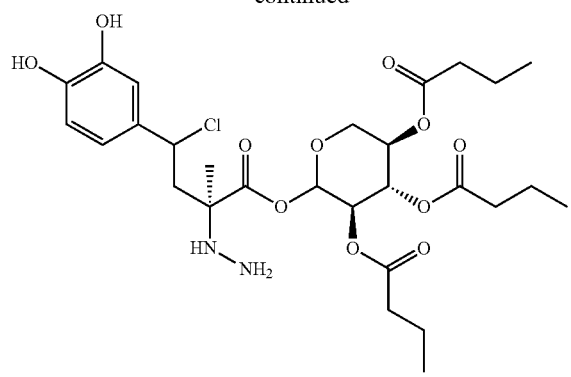
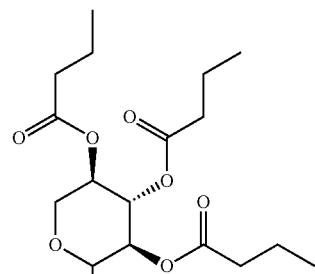
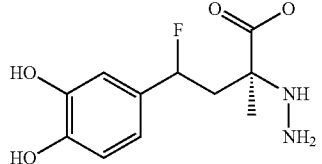
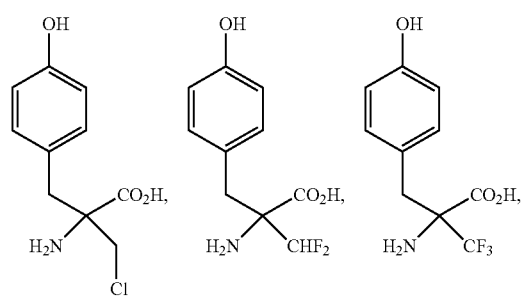
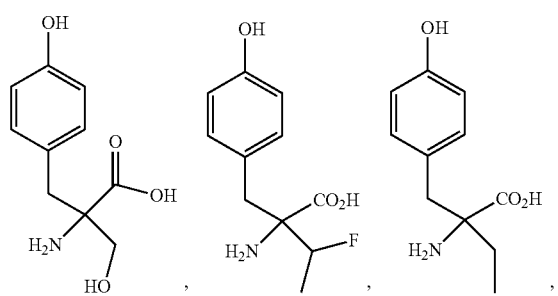
and pharmaceutically acceptable salts thereof.
2. A compound chosen from the following compounds
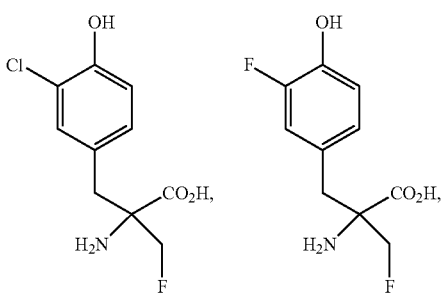
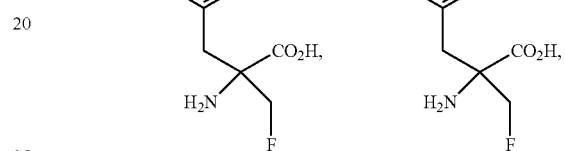
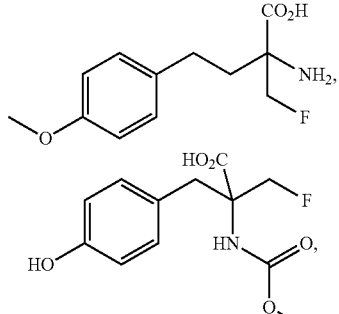
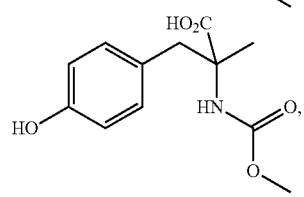
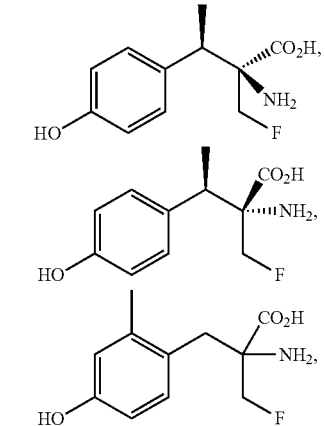

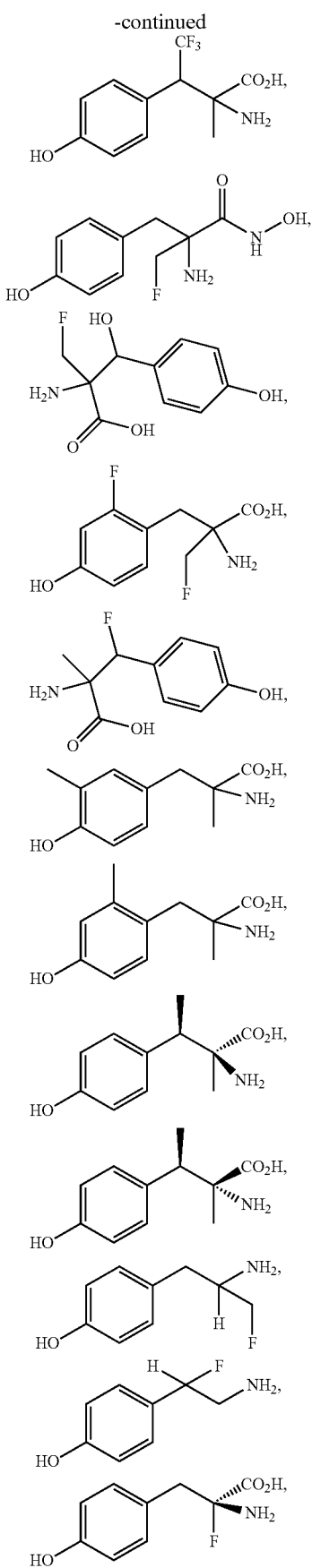

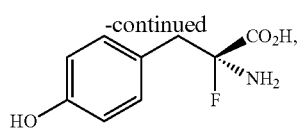

and pharmaceutically acceptable salts thereof.

3. A compound of formula (I):

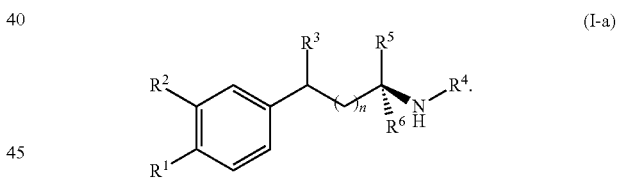

or a pharmaceutically acceptable salt thereof,
wherein
n is 0 or 1;
R$^1$ is H or —OR$^A$, wherein R$^A$ is H, —C(O)C$_{1-6}$ alkyl, or an acylated sugar;
R$^2$ is H, halogen, amino, C$_{1-6}$ alkyl, or —OR$^A$, wherein R$^A$ is H or an acylated sugar;
R$^3$ is H, a halogen, —OH, or C$_{1-6}$ alkyl optionally substituted with one or more halogens;
R$^4$ is H, —NH$_2$, —C(O)OCH$_3$, or an acylated sugar;
R$^5$ is H, —C(O)OH, —C(O)OC$_{1-6}$ alkyl, —C(O)Oglycoside, —C(O)NHOH, or —C(O)O(acylated sugar); and
R$^6$ is H, halogen, or optionally substituted C$_{1-6}$ alkyl;
provided that at least one R$^A$ is present; or provided that R$^3$ and/or R$^6$ comprise a halogen.

4. The compound of formula (I) according to embodiment 3, or a pharmaceutically acceptable salt thereof, wherein the compound is a compound of formula (I-a):

(I-a)

5. The compound of formula (I) according to any one of embodiments 3 and 4, or a pharmaceutically acceptable salt thereof, wherein
n is 0 or 1;
R$^1$ is H, —C(O)C$_{1-6}$ alkyl, or —OR$^A$, wherein R$^A$ is H or an acylated sugar;
R$^2$ is H, or —OR$^A$, wherein R$^A$ is H or an acylated sugar;
R$^3$ is H, or a halogen;
R$^4$ is H, —NH$_2$, or an acylated sugar;
R$^5$ is —C(O)OH, —C(O)OC$_{1-6}$ alkyl, —C(O)Oglycoside, or —C(O)O(acylated sugar); and
R$^6$ is H or optionally substituted C$_{1-6}$ alkyl;
provided that at least one R$^A$ is present; or provided that R$^3$ and/or R$^6$ comprise a halogen.

6. The compound of formula (I) according to any one of embodiments 3 to 5, or a pharmaceutically acceptable salt thereof, wherein R$^1$ is —OR$^A$.

7. The compound of formula (I) according to any one of embodiments 3 to 6, or a pharmaceutically acceptable salt thereof, wherein R$^2$ is H or —OR$^A$.

8. The compound of formula (I) according to any one of embodiments 3 to 7, wherein each $R^4$ is H.
9. The compound of formula (I) according to any one of embodiments 3 and 4, or a pharmaceutically acceptable salt thereof, wherein $R^2$ is a halogen.
10. The compound of formula (I) according to any one of embodiments 3 to 9, or a pharmaceutically acceptable salt thereof, wherein $R^3$ is fluoro or chloro.
11. The compound of formula (I) according to any one of embodiments 3 to 9, or a pharmaceutically acceptable salt thereof, wherein $R^3$ is H.
12. The compound of formula (I) according to any one of embodiments 3 to 11, or a pharmaceutically acceptable salt thereof, wherein $R^4$ is H.
13. The compound of formula (I) according to any one of embodiments 3 to 11, or a pharmaceutically acceptable salt thereof, wherein $R^4$ is —$NH_2$.
14. The compound of formula (I) according to any one of embodiments 3 to 13, or a pharmaceutically acceptable salt thereof, wherein $R^5$ is —C(O)OH.
15. The compound of formula (I) according to any one of embodiments 3 to 13, or a pharmaceutically acceptable salt thereof, wherein $R^5$ is —C(O)Oacylated sugar.
16. The compound of formula (I) according to any one of embodiments 3, 4, and 6 to 13, or a pharmaceutically acceptable salt thereof, wherein $R^5$ is H.
17. The compound of formula (I) according to any one of embodiments 3 to 16, or a pharmaceutically acceptable salt thereof, wherein $R^6$ is H.
18. The compound of formula (I) according to any one of embodiments 3 to 16, or a pharmaceutically acceptable salt thereof, wherein $R^6$ is a $C_{1-6}$ alkyl.
19. The compound of formula (I) according to any one of embodiments 3 to 16, or a pharmaceutically acceptable salt thereof, wherein $R^6$ is a $C_{1-6}$ alkyl substituted with one, two, or three halogens.
20. The compound of formula (I) according to any one of embodiments 3 to 16, or a pharmaceutically acceptable salt thereof, wherein $R^6$ is a $C_{1-6}$ alkyl substituted with one, two, or three fluorine atoms.
21. The compound of formula (I) according to any one of embodiments 3 to 20, or a pharmaceutically acceptable salt thereof, wherein n is 0.
22. The compound of formula (I) according to any one of embodiments 3 to 20, or a pharmaceutically acceptable salt thereof, wherein n is 1.
23. The compound of formula (I) according to any one of embodiments 3 and 4, or a pharmaceutically acceptable salt thereof, wherein
    n is 0;
    $R^1$ is —OH;
    $R^2$ is halogen;
    $R^3$ is H, a halogen, or —OH, $C_{1-6}$ alkyl optionally substituted with one or more halogens;
    $R^4$ is H, —$NH_2$, or an acylated sugar;
    $R^5$ is H, —C(O)OH, —C(O)O$C_{1-6}$ alkyl, —C(O)Oglycoside, —C(O)NHOH, or —C(O)O(acylated sugar); and
    $R^6$ is H or optionally substituted $C_{1-6}$ alkyl.
24. The compound of formula (I) according to anyone of embodiments 3, 4, and 23, or a pharmaceutically acceptable salt thereof, wherein
    n is 0;
    $R^1$ is —OH;
    $R^2$ is halogen;
    $R^3$ is H;
    $R^4$ is H;
    $R^5$ is —C(O)OH; and
    $R^6$ is optionally substituted alkyl.

25. A pharmaceutical composition comprising at least one pharmaceutically acceptable excipient and at least one entity chosen from the compounds according to any one of embodiments 1 to 24 and pharmaceutically acceptable salts thereof.
26. A method of treating Parkinson's disease comprising administering to a subject in need thereof a therapeutically effective amount of at least one entity chosen from the compounds according to any one of embodiments 1 to 24 and pharmaceutically acceptable salts thereof or a pharmaceutical composition according to embodiment 25.
27. A method of inhibiting a decarboxylase-mediated conversion of L-DOPA to L-dopamine comprising contacting the decarboxylase with at least one entity chosen from the compounds according to any one of embodiments 1 to 24 and pharmaceutically acceptable salts thereof or a pharmaceutical composition according to embodiment 25.
28. The method of embodiment 27, wherein the decarboxylase is tyrosine decarboxylase.

The following examples are meant to illustrate the disclosure. They are not meant to limit the disclosure in any way.

EXAMPLES

Example 1: Preparation of Exemplary Compounds

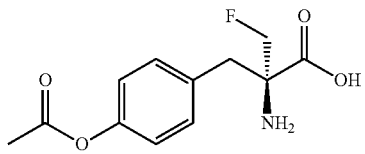

Compound A: (S)-2-(4-acetoxybenzyl)-2-amino-3-fluoropropanoic Acid (2S)-2-amino-3-fluoro-2-[(4-hydroxyphenyl)methyl]propanoic acid (1 equiv), is treated with $Na_2CO_3$, acetic anhydride to afford the title compound (S)-2-(4-acetoxybenzyl)-2-amino-3-fluoropropanoic acid.

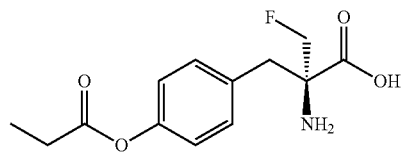

Compound B: (S)-2-amino-3-fluoro-2-(4-(propionyloxy)benzyl)propanoic Acid (2S)-2-amino-3-fluoro-2-[(4-hydroxyphenyl)methyl]propanoic acid (1 equiv), is treated with $Na_2CO_3$, propionic anhydride to afford the title compound (S)-2-amino-3-fluoro-2-(4-(propionyloxy)benzyl)propanoic acid.

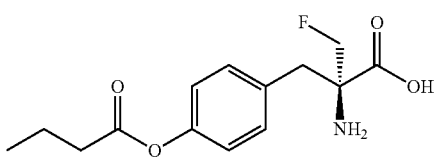

Compound C: (S)-2-amino-2-(4-(butyryloxy)benzyl)-3-fluoropropanoic Acid (2S)-2-amino-3-fluoro-2-[(4-hydroxyphenyl)methyl]propanoic acid (1 equiv), is treated with Na$_2$CO$_3$, butyric anhydride to afford the title compound (S)-2-amino-2-(4-(butyryloxy)benzyl)-3-fluoropropanoic acid.

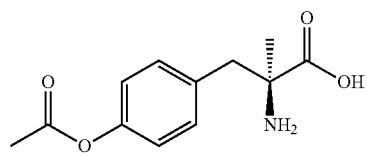

Compound D: (S)-3-(4-acetoxyphenyl)-2-amino-2-methylpropanoic Acid ((2R)-2-amino-3-(4-hydroxyphenyl)-2-methylpropanoic acid (1 equiv), is treated with Na$_2$CO$_3$, acetic anhydride to afford the title compound (S)-3-(4-acetoxyphenyl)-2-amino-2-methylpropanoic acid.

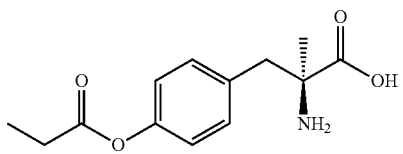

Compound E: (S)-2-amino-2-methyl-3-(4-(propionyloxy)phenyl)propanoic Acid (((2R)-2-amino-3-(4-hydroxyphenyl)-2-methylpropanoic acid (1 equiv), is treated with Na$_2$CO$_3$, propionic anhydride to afford the title compound (S)-2-amino-2-methyl-3-(4-(propionyloxy)phenyl)propanoic acid

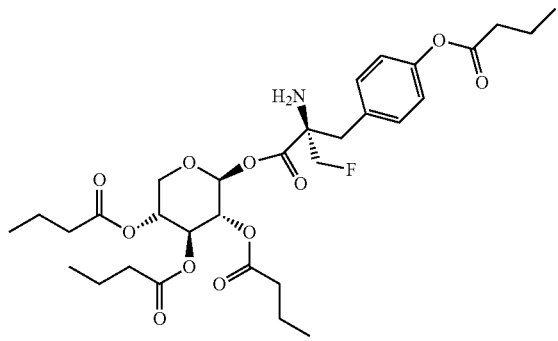

Compound F: (2S,3R,4S,5R)-2-(((S)-2-amino-2-(4-(butyryloxy)benzyl)-3-fluoropropanoyl)oxy)tetrahydro-2H-pyran-3,4,5-triyl tributyrate (2S)-2-amino-3-fluoro-2-[(4-hydroxyphenyl)methyl]propanoic acid (1 equiv), is treated with 1 eq of Na$_2$CO$_3$ and butyric anhydride and the corresponding butyric acid will be DCC coupled to (2S,3S,4R,5S)-2-hydroxytetrahydro-2H-pyran-3,4,5-triyl tributyrate (which can be synthesized from (2S,3S,4R,5S)-tetrahydro-2H-pyran-2,3,4,5-tetraol) to afford the title compound (2S,3R,4S,5R)-2-(((S)-2-amino-2-(4-(butyryloxy)benzyl)-3-fluoropropanoyl)oxy)tetrahydro-2H-pyran-3,4,5-triyl tributyrate.

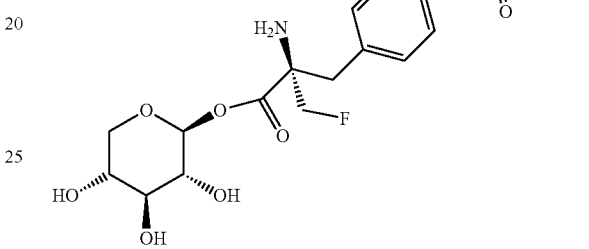

Compound G: 4-((S)-2-amino-2-(fluoromethyl)-3-oxo-3-(((2S,3R,4S,5R)-3,4,5-trihydroxytetrahydro-2H-pyran-2-yl)oxy)propyl)phenyl Butyrate (2S)-2-amino-3-fluoro-2-[(4-hydroxyphenyl)methyl]propanoic acid (1 equiv) is treated with 1 equivalent of Na$_2$CO$_3$ and butyric anhydride, and the corresponding butyric acid will be DCC coupled to (2S,3S,4R,5S)-2-hydroxytetrahydro-2H-pyran-3,4,5-triyl acetate (which can be synthesized from (2S,3S,4R,5S)-tetrahydro-2H-pyran-2,3,4,5-tetraol). This material is then treated with dilute lithium hydroxide in water to afford the title compound.

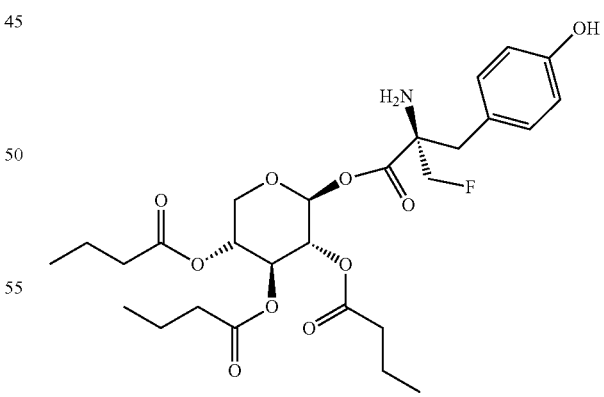

Compound H: (2S,3R,4S,5R)-2-(((S)-2-amino-3-fluoro-2-(4-hydroxybenzyl)propanoyl)oxy)tetrahydro-2H-pyran-3,4,5-triyl Tributyrate (2S)-2-amino-3-fluoro-2-[(4-hydroxyphenyl)methyl]propanoic acid (1 equiv), is treated with 1 eq of BnBr, K$_2$CO$_3$ in THF and the corresponding benzyl acid will be DCC coupled to (2S,3S,4R,5S)-2-hydroxytetrahydro-2H-pyran-3,4,5-triyl tributyrate (which can be synthesized from (2S,3S,4R,5S)-tetrahydro-2H-pyran-2,3,4,5-tetraol) and hydrogenated with Pd(OH)$_2$/H$_2$, to afford the title compound hydrogenated with Pd(OH)$_2$/H$_2$ to afford the title compound (2S,3R,4S,5R)-2-(((S)-2-amino-3-fluoro-2-(4-hydroxybenzyl)propanoyl)oxy)tetrahydro-2H-pyran-3,4,5-triyl tributyrate.

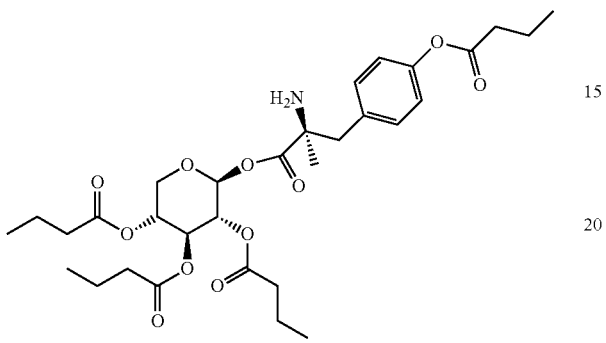

Compound I: (2S,3R,4S,5R)-2-(((S)-2-amino-3-(4-(butyryloxy)phenyl)-2-methylpropanoyl)oxy)tetrahydro-2H-pyran-3,4,5-triyl Tributyrate ((2R)-2-amino-3-(4-hydroxyphenyl)-2-methylpropanoic acid (1 equiv), is treated with 1 eq of is treated with 1 eq of Na$_2$CO$_3$ and butyric anhydride and the corresponding carboxylic acid will be DCC coupled to (2S,3S,4R,5S)-2-hydroxytetrahydro-2H-pyran-3,4,5-triyl tributyrate (which can be synthesized from (2S,3S,4R,5S)-tetrahydro-2H-pyran-2,3,4,5-tetraol) to afford the title compound (2S,3R,4S,5R)-2-(((S)-2-amino-3-(4-(butyryloxy)phenyl)-2-methylpropanoyl)oxy)tetrahydro-2H-pyran-3,4,5-triyl tributyrate.

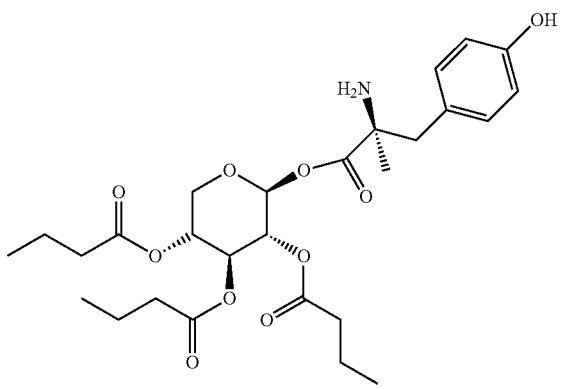

Compound J: (2S,3R,4S,5R)-2-(((S)-2-amino-3-(4-hydroxyphenyl)-2-methylpropanoyl)oxy)tetrahydro-2H-pyran-3,4,5-triyl Tributyrate ((2R)-2-amino-3-(4-hydroxyphenyl)-2-methylpropanoic acid (1 equiv), is treated with 1 eq of BnBr, K$_2$CO$_3$ in THF and the corresponding benzyl acid will be DCC coupled to (2S,3S,4R,5S)-2-hydroxytetrahydro-2H-pyran-3,4,5-triyl tributyrate (which can be synthesized from (2S,3S,4R,5S)-tetrahydro-2H-pyran-2,3,4,5-tetraol) and hydrogenated with Pd(OH)$_2$/H$_2$, to afford the title compound (2S,3R,4S,5R)-2-(((S)-2-amino-3-(4-hydroxyphenyl)-2-methylpropanoyl)oxy)tetrahydro-2H-pyran-3,4,5-triyl tributyrate.

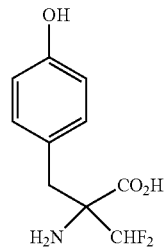

Compound K: 2-amino-3,3-difluoro-2-(4-hydroxybenzyl)propanoic Acid

Step 1:
To a solution of LDA (2 M, 60.18 mL, 2 eq, THF) in THF (50 mL) was added 2-(4-methoxyphenyl)acetic acid (10 g, 60.18 mmol, 1 eq) in THF (50 mL) at −70° C. and the mixture was stirred at 0° C. for 3 h. Then the mixture was cooled to −70° C. and ethyl 2,2-difluoroacetate (8.21 g, 66.20 mmol, 1.1 eq) in THF (50 mL) was added to the mixture at −70° C. and stirred at −70° C. for 2 h. The reaction mixture was quenched by addition 1N HCl 150 mL at 0° C., and then extracted with EtOAc 300 mL (100 mL*3). The combined organic layers were washed with sat. NaHCO$_3$ 150 mL (50 mL*3) and brine 100 mL (50 mL*2), dried over Na$_2$SO$_4$, filtered and the filtrate was concentrated under reduced pressure to give a residue. The residue was purified by column chromatography (SiO$_2$, Petroleum ether/Ethyl acetate=1/0 to 0/1) to give 1,1-difluoro-3-(4-methoxyphenyl)propan-2-one (2.3 g, 11.49 mmol, 19.09% yield) as yellow liquid.

Step 2:
A mixture of 1,1-difluoro-3-(4-methoxyphenyl)propan-2-one (2.3 g, 11.49 mmol, 1 eq) and (NH$_4$)$_2$CO$_3$ (5.19 g, 54.00 mmol, 5.77 mL, 4.7 eq) in EtOH (12 mL) and H$_2$O (8 mL) was stirred at 55° C., degassed and purged with N$_2$ 3 times, and then NaCN (608.12 mg, 12.41 mmol, 1.08 eq) was added to the mixture and stirred at 55° C. for 21 hr under N$_2$ atmosphere. Then the mixture was stirred at 90° C. for 0.5 hr. The reaction mixture was diluted with H$_2$O 20 mL and extracted with EtOAc 120 mL (20 mL*6). The combined organic layers were dried over Na$_2$SO$_4$, filtered and the filtrate was concentrated under reduced pressure to give a residue. The residue was purified by column chromatography (SiO$_2$, Petroleum ether/Ethyl acetate=1/0 to 0/1) to give 5-(difluoromethyl)-5-[(4-methoxyphenyl)methyl]imidazolidine-2,4-dione (1.9 g, 5.98 mmol, 52.02% yield, 85% purity) as a yellow solid.

Step 3:
A mixture of 5-(difluoromethyl)-5-[(4-methoxyphenyl)methyl]imidazolidine-2,4-dione (1.8 g, 6.66 mmol, 1 eq) in aq. HBr (18 mL, 48%) was degassed and purged with N2 for 3 times, and then the mixture was stirred at 110° C. for 5 hr under N$_2$ atmosphere. The reaction mixture was washed with EtOAc 30 mL (10 mL*3). The aqueous phase was concentrated under reduced pressure to give a residue. The residue was used sat. NaHCO$_3$ to adjust pH to 7~8, then 6 M HCl was added to the mixture and the pH was adjusted to 3~4. The residue was purified by prep-HPLC (column: Welch Xtimate C18 150*25 mm*5 um; mobile phase: [water (0.04% HCl)-ACN]; B %: 1%-5%, 10 min) to give 2-amino-3,3-difluoro-2-[(4-hydroxyphenyl)methyl]propanoic acid (56 mg, 202.95 umol, 3.05% yield, 97% purity, HCl) as a white solid. LCMS m/z=232.1. $^1$H NMR (400 MHz, DMSO-d6) δ 9.26 (s, 1H), 7.37 (br s, 1H), 7.06 (d, J=9.6 Hz, H), 6.63 (d, J=9.0 Hz, 2H), 6.12 (t, J=32.8 Hz, 1H), 3.03 (d, J=13.6 Hz, 1H), 2.67 (d, J=13.6 Hz, 1H).

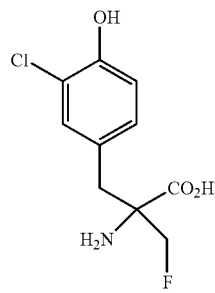 [SMILES: NC(CF)(Cc1ccc(O)c(Cl)c1)C(=O)O]

Compound L: 2-amino-2-(3-chloro-4-hydroxybenzyl)-3-fluoropropanoic Acid

Step 1:
To a solution of 4-(bromomethyl)-2-chloro-1-methoxybenzene (3 g, 12.74 mmol, 1 eq) and 2-(benzhydrylideneamino)acetonitrile (1.84 g, 8.34 mmol, 6.55e-1 eq) in DCM (30 mL) was added benzyl(trimethyl)ammonium chloride (189.24 mg, 1.02 mmol, 176.86 uL, 0.08 eq), then aq. NaOH (10 M, 1.91 mL, 1.5 eq) was added dropwise at 0° C. The mixture was warmed to 25° C. and stirred for 12 hr. TLC indicated Reactant was consumed completely and two new spots formed. The reaction mixture was concentrated under reduced pressure to remove DCM (30 mL). The residue was purified by column chromatography (SiO$_2$, Petroleum ether/Ethyl acetate=20/1 to 10/1). Compound 2-(benzhydrylideneamino)-3-(3-chloro-4-methoxy-phenyl)propanenitrile (2.4 g, 6.40 mmol, 50.26% yield) was obtained as a yellow oil.

Step 2:
To a solution of 2-(benzhydrylideneamino)-3-(3-chloro-4-methoxy-phenyl)propanenitrile (2.4 g, 6.40 mmol, 1 eq) in THF (25 mL) was added fluoro(iodo)methane (5.12 g, 32.01 mmol, 5 eq) and KOtBu (3.59 g, 32.01 mmol, 5 eq). The mixture was stirred at 25° C. for 1 hr. LC-MS showed 2-(benzhydrylideneamino)-3-(3-chloro-4-methoxy-phenyl)propanenitrile was consumed completely and the desired MS was detected. The reaction mixture was filtered and filtrate concentrated under reduced pressure to give a residue. The residue was purified by prep-TLC (SiO$_2$, Petroleum Ether: Ethyl Acetate=3:1). Compound 2-(benzhydrylideneamino)-2-[(3-chloro-4-methoxy-phenyl)methyl]-3-fluoro-propanenitrile (800 mg, 1.97 mmol, 30.71% yield) was obtained as yellow oil.

Step 3:
The mixture of 2-(benzhydrylideneamino)-2-[(3-chloro-4-methoxy-phenyl)methyl]-3-fluoro-propanenitrile (800 mg, 1.97 mmol, 1 eq) in aq. HBr (331.43 mg, 1.97 mmol, 222.44 uL, 48% purity, 1 eq) was stirred at 110° C. for 12 hr. LC-MS showed 2-(benzhydrylideneamino)-2-[(3-chloro-4-methoxy-phenyl)methyl]-3-fluoro-propanenitrile was consumed completely. The residue was diluted with H$_2$O (10 mL) and extracted with EtOAc 15 mL (5 mL*3). The H$_2$O phase was freeze-dried. The residue was purified by prep-HPLC (column: Phenomenex luna C$_{18}$ 250*50 mm*10 um; mobile phase: [water (0.1% TFA)-ACN]; B %: 1%-20%, 10 min) to give the crude product. The crude product in H$_2$O (3 mL) was adjusted pH to 7~8 with sat. NaHCO$_3$ aq. then adjusted the pH to 3~4 with 6M HCl. The aqueous phase was purified by purified by prep-HPLC (column: Phenomenex luna C$_{18}$ 250*50 mm*10 um; mobile phase: [water (0.05% HCl)-ACN]; B %: 1%-20%, 10 min). Compound 2-amino-2-[(3-chloro-4-hydroxy-phenyl)methyl]-3-fluoro-propanoic acid (150 mg, 527.96 mol, 54.48% yield, HCl) was obtained as a white solid. LCMS m/z=248.0. $^1$H NMR (400 MHz, DMSO-d6) δ 10.29 (br s, 1H), 7.21 (d, J=2.0 Hz, 1H), 7.00 (dd, J=8.4, 2.0 Hz, 1H), 6.92 (d, J=8.4 Hz, 1H), 4.80 (dd, J=46.8 9.8 Hz, 1H), 4.70 (dd, J=46.8, 9.8 Hz, 1H), 2.99 (d, J=14.4 Hz, 1H), 2.94 (d, J=14.4 Hz, 1H).

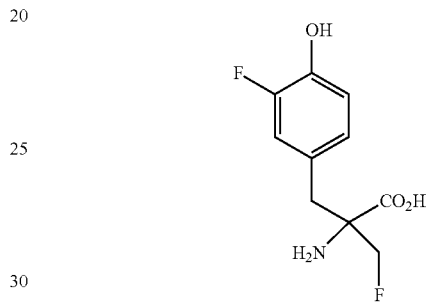

Compound M: 2-amino-3-fluoro-2-(3-fluoro-4-hydroxybenzyl)propanoic Acid

Step 1:
To a solution of 4-(bromomethyl)-2-fluoro-1-methoxybenzene (3 g, 13.70 mmol, 1.51 eq) and 2-(benzhydrylideneamino)acetonitrile (2 g, 9.08 mmol, 1 eq) in DCM (30 mL) was added benzyl(trimethyl)ammonium chloride (134.89 mg, 726.39 umol, 126.06 uL, 0.08 eq), then aq. NaOH (10 M, 1.36 mL, 1.5 eq) was added dropwise at 0° C. The mixture was warmed to 50° C. and stirred for 12 hr. TLC indicated 4-(bromomethyl)-2-fluoro-1-methoxy-benzene was not consumed completely and two new spots formed. The reaction mixture was concentrated under reduced pressure to remove DCM (30 mL). The residue was purified by column chromatography (SiO$_2$, Petroleum ether/Ethyl acetate=10/1 to 5/1). Compound 2-(benzhydrylideneamino)-3-(3-fluoro-4-methoxy-phenyl)propanenitrile (2.6 g, 7.25 mmol, 79.89% yield) was obtained as yellow oil.

Step 2:
To a solution of 2-(benzhydrylideneamino)-3-(3-fluoro-4-methoxy-phenyl)propanenitrile (2.6 g, 7.25 mmol, 1 eq) and fluoro(iodo)methane (5.80 g, 36.27 mmol, 5 eq) in THF (30 mL) was added KOtBu (4.07 g, 36.27 mmol, 5 eq, solid). The mixture was stirred at 25° C. for 1.5 hr. LC-MS showed 2-(benzhydrylideneamino)-3-(3-fluoro-4-methoxy-phenyl)propanenitrile was consumed completely and desired MS was detected. The reaction mixture was filtered and filtrate concentrated under reduced pressure to give a residue. The residue was purified by column chromatography (SiO$_2$, Petroleum ether/Ethyl acetate=15/1 to 5/1). Compound 2-(benzhydrylideneamino)-3-fluoro-2-[(3-fluoro-4-methoxy-phenyl)methyl]propanenitrile (1 g, 2.56 mmol, 35.31% yield) was obtained as a yellow oil.

Step 3:

The mixture of 2-(benzhydrylideneamino)-3-fluoro-2-[(3-fluoro-4-methoxy-phenyl)methyl]propanenitrile (600 mg, 1.54 mmol, 1 eq) in aq. HBr (4.47 g, 26.52 mmol, 3 mL, 48% purity, 17.26 eq) was stirred at 110° C. for 12 hr. LC-MS showed 2-(benzhydrylideneamino)-3-fluoro-2-[(3-fluoro-4-methoxy-phenyl)methyl]propanenitrile was consumed completely and one main peak with desired MS was detected. The reaction mixture was concentrated under reduced pressure to remove HBr (3 mL). Then adjust pH to 7-8 by saturated NaHCO$_3$ aqueous and then adjust pH to 7-8 with 6N HCl. The aqueous phase was purified by prep-HPLC (column: Phenomenex luna C18 250*50 mm*10 um; mobile phase: [water (0.05% HCl)-ACN]; B %: 1%-10%, 10 min). Compound 2-amino-3-fluoro-2-[(3-fluoro-4-hydroxy-phenyl)methyl]propanoic acid (77 mg, 277.61 umol, 18.06% yield, 96.5% purity, HCl) was obtained as a white solid. LCMS m/z=232.0. $^1$H NMR (400 MHz, DMSO-d6) δ 10.01 (br s, 1H), 8.85 (br s, 3H), 7.04 (d, 12.4 Hz, 1H), 6.95 (t, J=8.4 Hz, 1H), 6.86 (d, J=8.4 Hz), 4.89 (dd, J=46.6, 10 Hz, 1H), 4.71 (dd, J=46.6, 10 Hz, 1H, 3.12-3.04 (m, 2H).

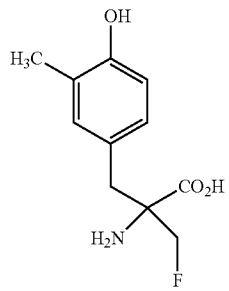 [SMILES: Cc1cc(CC(N)(CF)C(=O)O)ccc1O]

Compound N: 2-amino-3-fluoro-2-(4-hydroxy-3-methylbenzyl)propanoic Acid

Step 1:

To a solution of 4-(chloromethyl)-1-methoxy-2-methyl-benzene (3 g, 17.58 mmol, 1 eq) in acetone (30 mL) was added NaI (5.27 g, 35.16 mmol, 2 eq) at 25° C. Then the mixture was stirred at 25° C. for 10 hr. The reaction mixture was filtered and the filtrate was concentrated under reduced pressure to give a residue. The residue was diluted with H$_2$O 10 mL and extracted with EtOAc 30 mL (10 mL*3). The combined organic layers were washed with brine 20 mL (10 mL*2) and aq. sodium thiosulfate 20 mL (10 mL*2), dried over Na$_2$SO$_4$, filtered and the filtrate was concentrated under reduced pressure to give a residue. The residue was purified by column chromatography (SiO$_2$, Petroleum ether/Ethyl acetate=1/0 to 1/1) to give 4-(iodomethyl)-1-methoxy-2-methyl-benzene (4 g, 15.26 mmol, 86.81% yield) as a yellow liquid.

Step 2:

To a solution of 4-(iodomethyl)-1-methoxy-2-methyl-benzene (4 g, 15.26 mmol, 1.2 eq), 2-(benzhydrylideneamino)acetonitrile (2.80 g, 12.72 mmol, 1 eq) and N,N,N-trimethyl-1-phenylmethanaminium chloride (236.17 mg, 1.27 mmol, 220.72 uL, 0.1 eq) in DCM (40 mL) was added aq. NaOH (10 M, 2.29 mL, 1.8 eq) at 0° C. The mixture was stirred at 25° C. for 10 hr and stirred at 50° C. for 24 hr. The reaction mixture was filtered and the filtrate was concentrated under reduced pressure to give a residue. The residue was diluted with H$_2$O 15 mL and extracted with EtOAc 60 mL (20 mL*3). The combined organic layers were dried over Na$_2$SO$_4$, filtered and the filtrate was concentrated under reduced pressure to give a residue. The residue was purified by prep-HPLC (column: Agela DuraShell C18 250*80 mm*10 um; mobile phase: [water (0.04% NH$_3$H$_2$O+10 mM NH$_4$HCO$_3$)-ACN]; B %: 55%-85%, 20 min) to give 2-(benzhydrylideneamino)-3-(4-methoxy-3-methyl-phenyl)propanenitrile (1.9 g, 5.36 mmol, 42.15% yield) as yellow oil.

Step 3:

To a solution of 2-(benzhydrylideneamino)-3-(4-methoxy-3-methyl-phenyl)propanenitrile (0.5 g, 1.41 mmol, 1 eq) in THF (10 mL) was added t-BuOK (791.45 mg, 7.05 mmol, 5 eq) and fluoro(iodo)methane (2.26 g, 14.11 mmol, 10 eq). Then the mixture was stirred at 25° C. for 1 hr. The reaction mixture was filtered and the filtrate was concentrated under reduced pressure to give a residue. The residue was purified by column chromatography (SiO$_2$, Petroleum ether/Ethyl acetate=1/0 to 5/1) to give 2-(benzhydrylideneamino)-2-(fluoromethyl)-3-(4-methoxy-3-methyl-phenyl)propanenitrile (0.45 g, 1.16 mmol, 82.54% yield) as yellow oil.

Step 4:

A mixture of 2-(benzhydrylideneamino)-2-(fluoromethyl)-3-(4-methoxy-3-methyl-phenyl) propanenitrile (0.44 g, 1.14 mmol, 1 eq) in aq. HBr (8 mL, 48%) was degassed and purged with N2 for 3 times, and then the mixture was stirred at 110° C. for 10 hr under N$_2$ atmosphere. The reaction mixture was washed with EtOAc 30 mL (10 mL*3). The aqueous phase was concentrated under reduced pressure to give a residue. The residue was purified by prep-HPLC (column: Luna Omega 5u Polar C18 100 Å; mobile phase: [water (0.04% HCl)-ACN]; B %: 1%-10%, 7 min) to give the product. The product in H$_2$O (2 mL) was adjusted pH to 7~8 with sat. NaHCO$_3$ aq. then adjusted the pH to 3~4 with 6M HCl. The aqueous phase was purified by prep-HPLC (column: Luna Omega 5u Polar C$_{18}$ 100 Å; mobile phase: [water (0.04% HCl)-ACN]; B %: 1%-15%, 7 min) to give 2-amino-2-(fluoromethyl)-3-(4-hydroxy-3-methyl-phenyl)propanoic acid (54 mg, 204.78 umol, 20.87% yield, 100% purity, HCl) as a white solid. LCMS m/z=228.1. $^1$H NMR (400 MHz, CD$_3$OD) δ 6.96 (s, 1H), 6.89 (d, J=8.0 Hz, 1H), 6.71 (d, J=8.0 Hz, 1H), 4.89 (dd, J=47.0, 10.0 Hz, 1H), 4.65 (dd, J=47.0, 10.0 Hz, 1H), 3.17 (d, J=7.2 Hz, 1H), (2.96, J=14.2 Hz, 1H), 2.17 (s, 3H).

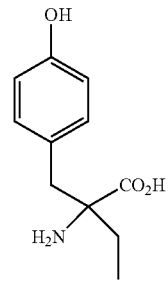

Compound M:
2-amino-2-(4-hydroxybenzyl)butanoic Acid

Step 1:

To a mixture of tert-butyl 2-amino-3-(4-hydroxyphenyl)propanoate (30 g, 126.43 mmol, 1 eq) and diphenylmethanone (23.04 g, 126.43 mmol, 1 eq) in Toluene (300 mL) was added TsOH (2.18 g, 12.64 mmol, 0.1 eq). The mixture was stirred at 120° C. for 48 h and remove water by Dean-Stark trap. TLC (PE:EtOAc=5:1) indicated a little starting materials remained, and one major new spot was detected. The reaction mixture was concentrated to give a residue. The residue was purified by column chromatography (SiO$_2$, Petroleum ether/Ethyl acetate=10/1 to 5/1). Compound tert-butyl 2-(benzhydrylideneamino)-3-(4-hydroxyphenyl) propanoate (8.5 g, 21.17 mmol, 16.75% yield) was obtained as a yellow oil.

Step 2:

To the solution of tert-butyl (2S)-2-(benzhydrylideneamino)-3-(4-hydroxyphenyl)propanoate (12.5 g, 31.13 mmol, 1 eq) in THF (125 mL) was added NaH (1.62 g, 40.47 mmol, 60% purity, 1.3 eq) at 0° C. The mixture was stirred at 0° C. for 0.5 h. Then MOMCl (3.26 g, 40.47 mmol, 3.07 mL, 1.3 eq) was added drop-wise to the mixture at 0° C. The mixture was allowed to warm to 25° C. and stirred at 25° C. for 2.5 h. TLC (PE:EtOAc=5:1) indicated the starting material was consumed completely and one new spot formed. The mixture was poured into sat. NaHCO$_3$ (100 mL) at 0-5° C. The aqueous phase was extracted with EtOAc (100 mL*3). The combined organic layers were dried over Na$_2$SO$_4$, filtered and concentrated in vacuum. Compound tert-butyl (2S)-2-(benzhydrylideneamino)-3-[4-(methoxymethoxy)phenyl]propanoate (10 g, 22.44 mmol, 72.09% yield) was obtained as a yellow oil.

Step 3:

To a solution of tert-butyl (2S)-2-(benzhydrylideneamino)-3-[4-(methoxymethoxy)phenyl]propanoate (2.00 g, 4.49 mmol, 1 eq) in THF (40 mL) and HMPA (7.45 g, 41.57 mmol, 7.30 mL, 9.26 eq) was added dropwise LDA (2 M, 15.71 mL, 7 eq) at −70° C. under N$_2$. The mixture was stirred at −70° C. for 0.5 h. Then CH$_3$CH$_2$I (7.00 g, 44.89 mmol, 3.59 mL, 10 eq) was drop-wise to the above mixture at −70° C. The reaction mixture was allowed to warm to 25° C. and stirred at 25° C. for 1.5 h. TLC (PE:EtOAc=5:1) indicated the starting material was consumed completely and one new spot formed. The reaction was clean according to TLC. The reaction mixture was quenched by sat. NaHCO$_3$ 100 mL at 0° C. The organic phase was separated, washed with EtOAc (50 mL*3), dried over NaSO$_4$, filtered and concentrated under reduced pressure to give a residue. The residue was purified by column chromatography (SiO$_2$, Petroleum ether/Ethyl acetate=20/1 to 8/1). Compound tert-butyl 2-(benzhydrylideneamino)-2-[[4-(methoxymethoxy)phenyl]methyl]butanoate (1 g, 2.11 mmol, 47.04% yield) was obtained as a yellow oil.

Step 4:

To a solution of tert-butyl 2-(benzhydrylideneamino)-2-[[4-(methoxymethoxy)phenyl]methyl]butanoate (1.03 g, 2.17 mmol, 1 eq) in THF (30 mL) was added aq. citric acid (21.81 g, 5.68 mmol, 21.83 mL, 5% purity, 2.61 eq) and the reaction was stirred at 25° C. for 6 h. LC-MS (ET28600-23-P1A, RT=2.371 min) showed the starting material was consumed completely. The mixture was diluted with EtOAc (30 mL) and the mixture was extracted with EtOAc (60 mL*3). The combined organic phases were dried with anhydrous Na$_2$SO$_4$, filtered and concentrated in vacuum. The residue was purified by prep-HPLC (HPLC: ET28600-23-P1A, RT=2.522 min, 89.8% purity; Kromasil C18 (250*50 mm*10 um); mobile phase: [water (10 mM NH$_4$HCO$_3$)-ACN]; B %: 30%-60%, 10 min) to give desired compound. Compound tert-butyl 2-amino-2-[[4-(methoxymethoxy)phenyl]methyl]butanoate (0.25 g, 808.02 umol, 37.15% yield) was obtained as a yellow oil. The product was detected by $^1$H NMR (ET28600-23-P1A, MeOD).

Step 5:

To the tert-butyl 2-amino-2-[[4-(methoxymethoxy)phenyl]methyl]butanoate (0.25 g, 808.02 umol, 1 eq) in dioxane (3 mL) was added aq. HCl (2.5 M, 6.46 mL, 20 eq). The mixture was stirred at 60° C. for 3 h. LC-MS (ET28600-33-P1B, product: M+1=210, RT=0.877 min) showed the starting material was consumed completely. The reaction mixture on notebook page ET28600-24-P1 was combined to ET28600-33-P1 for work up. The reaction mixture was partitioned between water (20 mL) and EtOAc (30 mL). The organic phase was separated, washed with sat. NaHCO$_3$ (5 mL*3), dried over though Na$_2$SO$_4$, filtered and concentrated under reduced pressure to give a residue. The residue was purified by prep-HPLC (HPLC: ET28600-33-P1A, RT=1.772 min; column: Waters Atlantis T3 150*30 mm*5 um; mobile phase: [water (0.05% HCl)-ACN]; B %: 1%-30%, 12 min) to give desired compound as a white solid. Total 106 mg of 2-amino-2-[(4-hydroxyphenyl)methyl]butanoic acid (HCl salt) was obtained (ET28600-33-P1&ET28600-24-P1, combined together) as a white solid. LCMS m/z=210.1. $^1$H NMR (400 MHz, CD$_3$OD) δ 7.08 (d, J=8.4 Hz, 1H), 6.78 (d, J=8.4 Hz, 1H), 3.22 (d, J=14.4 Hz, 1H) 2.99 (d, J=14.4 Hz, 1H), 2.12-2.07 (m, 1H), 1.90-1.84 (m, 1H), 1.04 (t, J=7.2 Hz, 1H).

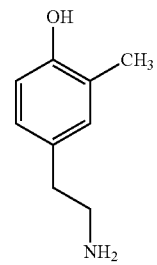

Compound P: 4-(2-aminoethyl)-2-methylphenol

Step 1:

To a solution of 4-hydroxy-3-methyl-benzaldehyde (1 g, 7.34 mmol, 1 eq) in CH$_3$NO$_2$ (10 mL) was added NH$_4$OAc (113.23 mg, 1.47 mmol, 0.2 eq). The mixture was stirred at 110° C. for 2 hr. LC-MS showed 4-hydroxy-3-methyl-benzaldehyde was consumed completely and one main peak with desired m/z was detected. The reaction mixture was concentrated under reduced pressure. The residue was purified by column chromatography (SiO$_2$, Petroleum ether/ Ethyl acetate=80/1 to 0/1). Compound 2-methyl-4-[(E)-2-nitrovinyl]phenol (700 mg, 3.91 mmol, 53.19% yield) was obtained as yellow solid.

Step 2:

To a mixture of LiAlH$_4$ (105.92 mg, 2.79 mmol, 10 eq) in THF (10 mL) was added 2-methyl-4-[(E)-2-nitrovinyl]phenol (50 mg, 279.06 umol, 1 eq) in THF (5 mL) at 0° C. under N$_2$. The mixture was stirred at 0° C. for 2 hr, and then the mixture was stirred at 70° C. for 12 hr. LCMS showed 2-methyl-4-[(E)-2-nitrovinyl]phenol was consumed completely. The suspension was cooled to 0° C. and the excess of LiAlH$_4$ was quenched with 6 M aqueous sodium hydroxide (1 mL). The precipitate was filtered off and the filter cake was washed with EtOAc (5 mL). The combined organic layers were washed with brine and dried Na$_2$SO$_4$. The residue was purified by prep-HPLC (column: Nano-micro Kromasil C18 80*25 mm 3 um; mobile phase: [water (0.04% HCl)-ACN]; B %: 5%-25%, 7 min). Compound 4-(2-aminoethyl)-2-methyl-phenol (3 mg, 15.83 umol, 2.39% yield, 99% purity, HCl) was obtained as a white solid. LCMS m/z=152.0. ¹H NMR (400 MHz, CD₃OD) δ 6.97 (s, 1H), 6.90 (d, J=8.2 Hz, 1H), 6.71 (d, J=8.2 Hz, 1H), 3.10 (t, J=7.6 Hz, 2H), 2.81 (t, J=7.6 Hz, 2H), 2.18 (s, 3H).

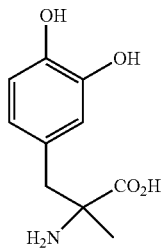

Compound Q:
2-amino-3-(3,4-dihydroxyphenyl)-2-methylpropanoic Acid

Step 1:
To a mixture of tert-butyl 2-(benzhydrylideneamino)acetate (2 g, 6.77 mmol, 1 eq) in DMF (20 mL) was added NaH (324.98 mg, 8.13 mmol, 60% purity, 1.2 eq) in one portion at 0° C. The mixture was stirred at 0° C. for 0.5 hr. Then to the mixture was added 4-(bromomethyl)-1,2-dimethoxy-benzene (1.88 g, 8.13 mmol, 1.2 eq). The mixture was stirred at 25° C. for 2 hr. LC-MS showed Reactant was consumed completely and one main peak with desired m/z (M+1=446.2, RT=2.434 min) was detected. The mixture was poured to sat. NaHCO₃ (40 mL) at 0-5° C. The mixture was extracted with ethyl acetate (20 mL*3). The combined organic phase was washed with brine (15 mL*4), dried with anhydrous Na₂SO₄, filtered and concentrated in vacuum. The residue was purified by column chromatography (SiO₂, Petroleum ether/Ethyl acetate=20/1 to 3/1). Compound tert-butyl 2-(benzhydrylideneamino)-3-(3,4-dimethoxyphenyl) propanoate (1.9 g, 4.26 mmol, 62.98% yield) was obtained as a yellow oil.

Step 2:
To the mixture LDA (2 M, 3.93 mL, 7 eq) in THF (6 mL) was added the solution tert-butyl 2-(benzhydrylideneamino)-3-(3,4-dimethoxyphenyl)propanoate (0.5 g, 1.12 mmol, 1 eq) in HMPA (1.86 g, 10.39 mmol, 1.83 mL, 9.26 eq) and THF (3 mL) at −70° C. under N₂. The mixture was stirred at −70° C. for 0.5 hr. Then to the mixture was added MeI (1.59 g, 11.22 mmol, 698.62 uL, 10 eq) drop-wise at −70° C. The mixture was allowed to warm to 25° C. and stirred at 25° C. for 1 hr. LC-MS indicated Reactant was consumed completely. The mixture was poured into sat. NaHCO₃ (15 mL) and extracted with ethyl acetate (15 mL*3), dried with anhydrous Na₂SO₄, filtered and concentrated in vacuum. The residue was purified by column chromatography (SiO₂, Petroleum ether/Ethyl acetate=20/1 to 8/1). Compound tert-butyl 2-(benzhydrylideneamino)-3-(3,4-dimethoxyphenyl)-2-methyl-propanoate (0.32 g, 696.30 umol, 62.05% yield) was obtained as a yellow oil.

Step 3:
The mixture of tert-butyl 2-(benzhydrylideneamino)-3-(3,4-dimethoxyphenyl)-2-methyl-propanoate (0.27 g, 587.50 umol, 1 eq) in aq. HBr (8.32 g, 41.12 mmol, 5.58 mL, 40% purity, 70 eq) was stirred at 100° C. for 4 hr. TLC (Petroleum ether: Ethyl acetate=10:1) indicated rt-butyl 2-(benzhydrylideneamino)-3-(3,4-dimethoxyphenyl)-2-methyl-propanoate was consumed completely. The reaction mixture was extracted with EtOAc (15 mL*3). The aqueous layer was concentrated under reduced pressure to remove the organic. The crude was purified by prep-HPLC (column: Nano-micro Kromasil C18 80*25 mm 3 um; mobile phase: [water (0.04% HCl)-ACN]; B %: 1%-8%, 7 min). The crude product was further purified by prep-HPLC (column: Welch Xtimate C18 150*25 mm*5 um; mobile phase: [water (0.04% HCl)-ACN]; B %: 1%-10%, 10 min). 2-amino-3-(3,4-dihydroxyphenyl)-2-methyl-propanoic acid (15 mg, 70.31 umol, 12% yield, 99% purity) was obtained as white solid as HCl salt. LCMS m/z=212.1. ¹H NMR (400 MHz, CD₃OD) δ 6.76 (d, J=8.4 Hz, 1H), 6.71 (s, 1H), 6.59 (d, J=8.4 Hz, 1H), 3.19 (d, J=14.2 Hz, 1H), 2.93 (d, J=14.2 Hz, 1H), 1.61 (s, 3H).

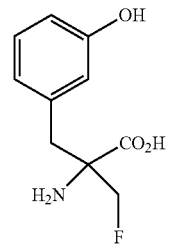

Compound R:
2-amino-3-fluoro-2-(3-hydroxybenzyl)propanoic Acid

Step 1:
To the solution of 2-amino-3-(3-hydroxyphenyl)propanoic acid (10 g, 55.19 mmol, 1 eq) in tert-butyl acetate (86.60 g, 745.54 mmol, 100.00 mL, 13.51 eq) was added perchloric acid (12.67 g, 88.31 mmol, 7.63 mL, 70% purity, 1.6 eq) drop-wise at 0° C. The mixture was stirred at 25° C. for 10 hr. TLC (Dichloromethane:Methanol=10:1, R_f=0.30) showed ~20% of R2-amino-3-(3-hydroxyphenyl)propanoic acid remained. One new spot was shown on TLC. Added EtOAc (50 mL) to the mixture, then washed the mixture with H₂O (50 mL). Then the organic phase was extracted with 1N HCl (10 mL). The combined aqueous phase was adjusted to pH=9 by 10% K₂CO₃ solution. Then the aqueous phase was extracted with DCM (30 mL*3). The combined organic phase was washed with brine (20 mL), dried with anhydrous Na₂SO₄, filtered and concentrated in vacuum. Tert-butyl 2-amino-3-(3-hydroxyphenyl)propanoate (4.35 g, 18.33 mmol, 33.21% yield) was obtained as off-white solid.

Step 2:
To the solution of tert-butyl 2-amino-3-(3-hydroxyphenyl)propanoate (4.35 g, 18.33 mmol, 1 eq) in toluene (90 mL) was added 4 A molecular sieve (4.35 g) and TsOH (157.84 mg, 916.58 umol, 0.05 eq). The mixture was stirred at 25° C. for 30 min under N₂. To the mixture was added diphenylmethanone (3.67 g, 20.16 mmol, 1.1 eq). The mixture was stirred at 110° C. for 9.5 hr. TLC (Petroleum ether: Ethyl acetate=5:1, R_f=0.50) indicated tert-butyl 2-amino-3-(3-hydroxyphenyl)propanoate was consumed completely. The reaction mixture was cooled to 25° C. Then the mixture was filtered. The filter cake was washed with EtOAc (50 mL*2). The combined organic phase was concentrated in vacuum. The residue was purified by flash silica gel chromatography (ISCO®; 100 g SepaFlash® Silica Flash Column, Eluent of 0~15% Ethyl acetate/Petroleum ethergradient @ 80 mL/min). Tert-butyl 2-(benzhydrylideneamino)-3-(3-hydroxyphenyl)propanoate (2.4 g, 5.98 mmol, 32.61% yield) was obtained as yellow solid.

Step 3:

To the mixture of tert-butyl 2-(benzhydrylideneamino)-3-(3-hydroxyphenyl)propanoate (2.4 g, 5.98 mmol, 1 eq) in DMF (25 mL) was added NaH (286.90 mg, 7.17 mmol, 60% purity, 1.2 eq) at 0° C. The mixture was stirred at 15° C. for 30 min. To the mixture was added MOMCl (673.79 mg, 8.37 mmol, 635.65 uL, 1.4 eq) drop-wise at 0° C. The mixture was stirred at 25° C. for 2 hr. TLC (Petroleum ether: Ethyl acetate=5:1, $R_f$=0.65) indicated tert-butyl 2-(benzhydrylideneamino)-3-(3-hydroxyphenyl)propanoate was consumed completely. The mixture was added slowly to saturated aq. $NaHCO_3$ (75 mL). The aqueous phase was extracted with MTBE (30 mL*3). The combined organic phase was washed with brine (15 mL*3), dried with anhydrous $Na_2SO_4$, filtered and concentrated in vacuum. tert-butyl 2-(benzhydrylideneamino)-3-[3-(methoxymethoxy)phenyl]propanoate (2.28 g, 5.12 mmol, 85.61% yield) was obtained as yellow oil.

Step 4:

To the solution of THF (30 mL) was added LDA (2 M, 17.91 mL, 7 eq) under $N_2$. Then Cool to −70° C. To the mixture was added tert-butyl 2-(benzhydrylideneamino)-3-[3-(methoxymethoxy)phenyl]propanoate (2.28 g, 5.12 mmol, 1 eq) in HMPA (8.49 g, 47.39 mmol, 8.33 mL, 9.26 eq) and THF (20 mL) drop-wise at −70° C. The mixture was stirred at −70° C. for 0.5 hr. Then fluoro(iodo)methane (8.18 g, 51.17 mmol, 10 eq) was added drop-wise at −70° C. The mixture was stirred at 25° C. for 1 hr. TLC (Petroleum ether: Ethyl acetate=10:1, $R_f$=0.66) showed the starting material was consumed completely. The mixture was poured into aq. $NaHCO_3$ (50 mL) slowly at 0-5° C. The mixture was extracted with ethyl acetate (10 mL*3). The combined organic phase was washed with brine (5 mL*2), dried with anhydrous $Na_2SO_4$, filtered and concentrated in vacuum. The residue was purified by flash silica gel chromatography (ISCO®; 10 g SepaFlash® Silica Flash Column, Eluent of 0~5% Ethyl acetate/Petroleum ethergradient @ 40 m L/min). tert-butyl 2-(benzhydrylideneamino)-2-(fluoromethyl)-3-[3-(methoxymethoxy)phenyl]propanoate (1.38 g, 2.89 mmol, 56.47% yield) was obtained as yellow oil.

Step 5:

To the solution of tert-butyl 2-(benzhydrylideneamino)-2-(fluoromethyl)-3-[3-(methoxymethoxy)phenyl]propanoate (1.38 g, 2.89 mmol, 1 eq) in THF (35 mL) was added citric acid (28.98 g, 7.54 mmol, 29.01 mL, 5% purity, 2.61 eq). The mixture was stirred at 25° C. for 6 hr. TLC (Petroleum ether: Ethyl acetate=10:1, $R_f$=0.13) indicated tert-butyl 2-(benzhydrylideneamino)-2-(fluoromethyl)-3-[3-(methoxymethoxy)phenyl]propanoate was consumed completely. One new spot with large polarity was detected. The mixture was concentrated in reduced pressure to remove THF. The aqueous phase was extracted with ethyl acetate (10 m L*3). The combined organic phase was washed with brine (10 mL), dried with anhydrous $Na_2SO_4$, filtered and concentrated in vacuum. The residue was purified by column chromatography ($SiO_2$, Petroleum ether/Ethyl acetate=10/1 to 0/1). tert-butyl 2-amino-2-(fluoromethyl)-3-[3-(methoxymethoxy)phenyl]propanoate (460 mg, 1.35 mmol, 46.74% yield, 92% purity) was obtained as white solid.

Step 6:

To the mixture of tert-butyl 2-amino-2-(fluoromethyl)-3-[3-(methoxymethoxy)phenyl]propanoate (240 mg, 765.88 umol, 1 eq) in THF (20 mL) was added $NaHCO_3$ (64.34 mg, 765.88 umol, 29.79 uL, 1 eq) in $H_2O$ (10 mL). The mixture was cooled to 0° C. To the mixture was added CbzCl (156.78 mg, 919.06 umol, 130.65 uL, 1.2 eq) slowly at 0° C. The mixture was stirred at 25° C. for 2 hr. TLC (Petroleum ether: Ethyl acetate=5:1, Rf=0.60) indicated Reactant was consumed completely. Combine two same scale batches together for work-up and purification. The mixture was extracted with ethyl acetate (10 mL*4). The combined organic phase was washed with brine (10 mL), dried with anhydrous $Na_2SO_4$, filtered and concentrated in vacuum. The residue was purified by prep-TLC ($SiO_2$, Petroleum ether: Ethyl acetate=5:1). tert-butyl 2-(benzyloxycarbonylamino)-2-(fluoromethyl)-3-[3-(methoxymethoxy)phenyl]propanoate (400 mg, 893.86 umol, 58.36% yield) was obtained as light yellow oil.

Step 7:

To the mixture of tert-butyl 2-(benzyloxycarbonylamino)-2-(fluoromethyl)-3-[3-(methoxymethoxy)phenyl]propanoate (300 mg, 670.40 umol, 1 eq) in THF (10 mL) was added aq. HCl (2.5 M, 5.36 mL, 20 eq). The mixture was stirred at 60° C. for 3 hr. LCMS showed tert-butyl 2-(benzyloxycarbonylamino)-2-(fluoromethyl)-3-[3-(methoxymethoxy)phenyl]propanoate was consumed completely. The mixture was concentrated in reduced pressure to remove THF. The aqueous phase was extracted with ethyl acetate (5 mL*3). The combined organic phase was washed with brine (3 mL), dried with anhydrous $Na_2SO_4$, filtered and concentrated in vacuum. The product was purified by prep-HPLC (column: Welch Xtimate C18 150*30 mm*5 um; mobile phase: [water (10 mM $NH_4HCO_3$)-ACN]; B %: 45%-75%, 3 min). tert-butyl 2-(benzyloxycarbonylamino)-2-(fluoromethyl)-3-(3-hydroxyphenyl)propanoate (157 mg, 389.15 umol, 58.05% yield) was obtained as colorless oil.

Step 8:

To the mixture of tert-butyl 2-(benzyloxycarbonylamino)-2-(fluoromethyl)-3-(3-hydroxyphenyl) propanoate (100 mg, 247.87 umol, 1 eq) in ACN (20 mL) was added TMSI (148.79 mg, 743.60 umol, 101.22 uL, 3 eq). The mixture was stirred at 25° C. for 2 hr. TLC (Petroleum ether: Ethyl acetate=5:1, $R_f$=0.02) indicated the starting material was consumed completely. The mixture was concentrated in reduced pressure. The crude was purified by prep-HPLC (column: Welch Xtimate C18 150*25 mm*5 um; mobile phase: [water (0.04% HCl)-ACN]; B %: 1%-3%, 10 min). 2-amino-2-(fluoromethyl)-3-(3-hydroxyphenyl)propanoic acid (27 mg, 96.36 umol, 38.87% yield, 89.1% purity, HCl) was obtained as yellow solid. LCMS m/z=214.1 $^1$H NMR (400 MHz, $CD_3OD$) δ 7.19 (app t, J=8.2 Hz, 1H), 6.78 (d, J=8.2 Hz, 1H), 6.71 (d, J=8.2 Hz, 1H), 6.69 (s 1H), 4.96 (dd, J=46, 10.4 Hz, 1H), 4.69 (dd, J=46, 10.4 Hz, 1H), 3.29 (d, J=14.4 Hz, 1H), 3.05 (d, J=14.4 Hz, 1H).

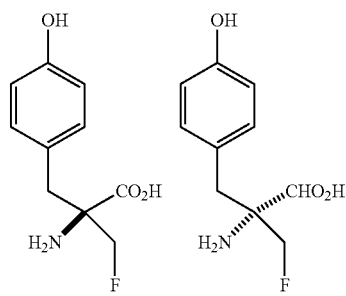

Compounds S and T: (S)-2-amino-3-fluoro-2-(4-hydroxybenzyl)propanoic Acid and (R)-2-amino-3-fluoro-2-(4-hydroxybenzyl)propanoic Acid Step 1:

Two reactions were carried out in parallel and combined together for work-up. To a solution of tert-butyl L-tyrosinate (60 g, 253 mmol, 1.00 eq) in dry DCM (300 mL) were added TsOH (6.53 g, 37.9 mmol, 0.15 eq) and $MgSO_4$ (60.9 g, 505 mmol, 2.00 eq) in one portion. After the addition, the suspension was stirred at 25° C. for 0.5 hr. Benzaldehyde (29.5 g, 278 mmol, 28.1 mL, 1.10 eq) was added to the solution in one portion. After addition, the suspension was stirred at 25° C. for 12 hrs. HNMR (ET27430-13-P1A1) showed the starting material was consumed completely. Two reactions were combined together for work-up. The suspension was filtered, and the filter cake was washed by DCM (200 mL×2). The filtrate was washed by cold aqueous solution of $NaHCO_3$(Sat. 800 mL). The organic phase was dried over $Na_2SO_4$, and concentrated under vacuum to give a solid. The solid was dried in the air for 12 hrs to oxidize PhCHO into PhCOOH. The solid was triturated with MTBE/Petroleum ether (2/1) at 25° C. for 30 mins. The suspension was filtered, and the filter cake was dissolved in DCM (300 mL). The organic layer was washed with cold aqueous solution of $NaHCO_3$(Sat. 200 mL). The organic phase was dried over $Na_2SO_4$, filtered and concentrated under vacuum to give tert-butyl (S,E)-2-(benzylideneamino)-3-(4-hydroxyphenyl)propanoate (110 g, 338 mmol, 66.9% yield) as an off-white solid.

Step 2:

Four reactions were carried out in parallel and combined together for work-up. To a solution of tert-butyl (S,E)-2-(benzylideneamino)-3-(4-hydroxyphenyl)propanoate (20 g, 61.5 mmol, 1.00 eq) in DMF (200 mL) was added NaH (2.70 g, 67.6 mmol, 60% purity, 1.10 eq) at 0° C. in portions. After the addition, the resulting suspension was stirred at 0° C. for 1.5 hrs. MOMCl (4.95 g, 61.5 mmol, 4.67 mL, 1.00 eq) was added to the suspension in one portion, and the suspension was stirred at 0° C. for 1 hr. LCMS (ET27430-22-P1A2) showed the starting material was consumed completely and one main peak with desired mass was detected. Four reactions were combined together for work-up. The suspension was slowly poured into cold saturated aqueous solution of $NaHCO_3$ (1200 mL) and extracted with MTBE (300 mL×4). The combined organic layer was washed with cold brine (600 mL×2), dried over $Na_2SO_4$, filtered and concentrated under reduced pressure to give tert-butyl (S,E)-2-(benzylideneamino)-3-(4-(methoxymethoxy)phenyl)propanoate (90.3 g, crude) as a yellow oil which was used to next step directly.

Step 3:

Four reactions were carried out in parallel and combined together for work-up. LDA (2 M, 29.8 mL, 2.20 eq) was added to THF (50 mL) at −70° C. drop-wise. After the addition, HMPA (12.1 g, 67.7 mmol, 11.9 mL, 2.50 eq) was added to the solution in one portion, and followed by a solution of tert-butyl (S,E)-2-(benzylideneamino)-3-(4-(methoxymethoxy)phenyl)propanoate (10.0 g, 27.1 mmol, 1.00 eq) in THF (20 mL) drop-wise at −70° C. The solution was stirred at −70° C. for 1 hr. Fluoroiodomethane (10.8 g, 67.7 mmol, 2.50 eq) was added to the solution drop-wise at −70° C. After the addition, the solution was stirred at −70° C. for 1 hr. LCMS (ET27430-25-P1A2) showed the starting material was consumed completely and one main peak with desired mass was detected. Four reactions were combined together for work-up. The solution was slowly poured into cold aqueous solution of $NaHCO_3$(Sat. 600 mL) and extracted with MTBE (300 mL×4). The combined organic layer was dried over $Na_2SO_4$, filtered and concentrated under vacuum to give tert-butyl (E)-2-(benzylideneamino)-3-fluoro-2-(4-(methoxymethoxy)benzyl)propanoate (50 g, crude) as a brown oil which was used to next step directly.

Step 4:

To a solution of tert-butyl (E)-2-(benzylideneamino)-3-fluoro-2-(4-(methoxymethoxy)benzyl)propanoate (60 g, 149 mmol, 1.00 eq) in THF (150 mL) was added citric acid monohydrate (1.08 kg, 257 mmol, 1200 mL, 5% purity, 1.72 eq). The solution was stirred at 20° C. for 5 hrs. TLC (Petroleum ether: Ethyl acetate=10:1, $R_f$ of material=0.5) showed the starting material was consumed completely, and one major new spot with higher polarity was detected. LCMS (ET27430-27-P1A) showed the reaction was completed. The solution was extracted with MTBE: Petroleum ether=1:1 (500 mL×2). The organic layer was washed by water (500 mL), and the organic layer was discarded. The combined aqueous layer was poured into aqueous solution of $NaHCO_3$(Sat. 600 mL). The aqueous phase was extracted with MTBE (600 mL×3). The combined organic layers were dried over $Na_2SO_4$, filtered and concentrated under reduced pressure to give a residue. The residue was purified by column chromatography ($SiO_2$, $NH_3 \cdot H_2O$/Petroleum ether/Dichloromethane=0/4/1, 0/2/1, 0.005/2/1, 0.005/1/1, 0.005/0/1) to give tert-butyl 2-amino-3-fluoro-2-(4-(methoxymethoxy)benzyl)propanoate (18 g, 57.44 mmol, 38.43% yield) as a brown oil. The racemic mixture (18 g, 57.44 mmol) was purified by SFC (column: DAICEL CHIRALPAK AD-H (250 mm*30 mm, 5 um); mobile phase: [0.1% $NH_3 \cdot H_2O$ ETON]; B %: 15%-15%, 2.3 min). (S)tert-butyl 2-amino-3-fluoro-2-(4-(methoxymethoxy)benzyl)propanoate (7.4 g, 23.6 mmol, 92.5% yield) was obtained as a brown oil and (R)-tert-butyl 2-amino-3-fluoro-2-(4-(methoxymethoxy)benzyl)propanoate (7.1 g, 22.7 mmol, 88.8% yield) was obtained as a brown oil.

Step 5:

To a solution of (S)tert-butyl 2-amino-3-fluoro-2-(4-(methoxymethoxy)benzyl)propanoate (6.52 g, 20.8 mmol, 1.00 eq) in THF (30 mL) was added aqueous solution of HCl (2.5 M, 83.2 mL, 10.0 eq). The solution was stirred at 60° C. for 3 hrs. LCMS (ET27430-31-P1A2) showed the reaction was completed. The reaction solution was lyophilized to give a crude product. The crude product was purified by pre-HPLC (column: Phenomenex luna C18 250*80 mm*10 um; mobile phase: [water (0.05% HCl)-ACN]; B %: 0%-9%, 20 min) to give (S)-2-amino-3-fluoro-2-(4-hydroxybenzyl)propanoic acid (2.3 g, 10.8 mmol, 51.9% yield) as a white solid. LCMS m/z=214. $^1$H NMR (400 MHz, DMSO-d6) δ 8.68 (br s, 1H), 7.01 (d, J=8.4 Hz, 1H), 6.72 (d, J=8.4 Hz, 1H), 4.84 (dd, J=45.2, 10.0 Hz, 1H), 4.63 (d, J=45.2, 10.0 Hz, 1H), 3.04 (d, J=14.0 Hz, 1H), 2.96 (d, J=14.0 Hz, 1H).

To a solution of (R)-tert-butyl 2-amino-3-fluoro-2-(4-(methoxymethoxy)benzyl)-propanoate (6.77 g, 21.6 mmol, 1.00 eq) in THF (30 mL) was added aqueous solution of HCl (2.5 M, 86.4 mL, 10.0 eq). The solution was stirred at 60° C. for 3 hrs. LCMS showed the reaction was completed. The reaction solution was lyophilized to give a crude product. The crude product was purified by pre-HPLC (column: Phenomenex luna C18 250*80 mm*10 um; mobile phase: [water (0.05% HCl)-ACN]; B %: 0%-9%, 20 min) to give (R)-2-amino-3-fluoro-2-(4-hydroxybenzyl)propanoic acid (2.3 g, 10.8 mmol, 49.9% yield) as a white solid. $^1$H NMR (400 MHz, DMSO-d6) δ 8.68 (br s, 1H), 7.01 (d, J=8.4 Hz, 1H), 6.72 (d, J=8.4 Hz, 1H), 4.84 (dd, J=45.2, 10.0 Hz, 1H), 4.63 (d, J=45.2, 10.0 Hz, 1H), 3.04 (d, J=14.0 Hz, 1H), 2.96 (d, J=14.0 Hz, 1H).

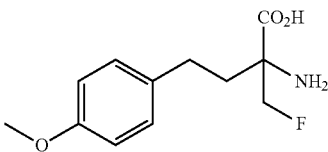 [SMILES: COc1ccc(CCC(N)(CF)C(=O)O)cc1]

Compound U: 2-amino-2-(fluoromethyl)-4-(4-methoxyphenyl)butanoic Acid

To a solution of 3-(4-methoxyphenyl)propanal in 250-mL round-bottomed flask charged with $NH_4Cl$ (1.2 eq), ammonia (3 eq), ethanol (0.2 M), and water (0.2M). Dissolve the mixture into a clear solution. Add NaCN (1.5 eq) to the mixture. Seal the flask quickly with a rubber stopper. Stir the mixture for 3 days. Extract the mixture with $CH_2Cl_2$ (100 mL). Wash the combined organic layer with water to remove the remaining NaCN. Dry the mixture with anhydrous sodium sulfate. Concentrate the mixture under reduced pressure to afford the product. The residue was purified by column chromatography to give 2-amino-4-(4-methoxyphenyl)butanenitrile in 70-80%. Yield. A mixture of the 2-amino-4-(4-methoxyphenyl)butanenitrile, $Et_3N$ and benzophenone (1:1.3:8 molar ratio, respectively) and DMF (7 mL/g ketone) was loaded in a round-bottomed, two-necked flask fitted with a refluxing condenser. A toluene (1 M) solution of $TiCl_4$, (0.9 molar with respect to the substrate) was carefully added dropwise to the solution After the addition was completed, the mixture was refluxed (35-40° C.) for 1 h and then allowed to stand 6 h at room temperature. The suspension was concentrated and extracted by diethyl ether and purified by column chromatography to give 2-((diphenylmethylene)amino)-4-(4-methoxyphenyl)butanenitrile in 23-30%. Yield. 2-amino-4-(4-methoxyphenyl) butanenitrile was treated with 11 eq of HBr (48 wt. % in $H_2O$) was added and the solution was heated to 60° C. for five days. Progress of the reaction was monitored by LCMS. The crude compound was purified by reverse phase column chromatography to give 2-amino-2-(fluoromethyl)-4-(4-hydroxyphenyl)butanoic acid 2-amino-2-(fluoromethyl)-4-(4-hydroxyphenyl)butanoic acid in 20% yield. 1H NMR (500 MHz, Deuterium Oxide) δ 7.34-7.26 (m, 2H), 7.02-6.96 (m, 2H), 5.11-4.76 (m, 2H), 2.89-2.78 (m, 1H), 2.70 (td, J=12.9, 5.0 Hz, 1H), 2.34-2.12 (m, 1H). LCMS: (M+1) 228.3, (M−1) 226.2.

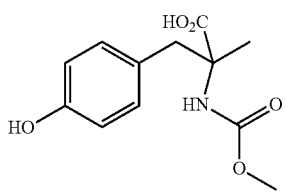 [SMILES: COC(=O)NC(C)(Cc1ccc(O)cc1)C(=O)O]

Compound V: 3-(4-hydroxyphenyl)-2-((methoxycarbonyl)amino)-2-methylpropanoic Acid Added methyl chloroformate (1 eq) to a solution of 2-amino-3-(4-hydroxyphenyl)-2-methylpropanoic acid and $NaHCO_3$ (20 eq) in a mixture of $H_2O$/THF (2 M). Stir the mixture at room temperature overnight. Dilute the mixture with $H_2O$. Wash the mixture with $Et_2O$. Acidify the aqueous layer to pH ~2-3. Evaporate to dryness and purified by reverse phase column chromatography to give 3-(4-hydroxyphenyl)-2-((methoxycarbonyl)amino)-2-methylpropanoic acid with 70% yield. $^1$H NMR (400 MHz, Methanol-$d_4$) δ 7.02-6.89 (m, 2H), 6.77-6.59 (m, 2H), 3.64 (s, 3H), 3.21-2.96 (m, 2H), 1.41 (s, 3H). LCMS: (M+1): 254.2, (M−1): 252.2.

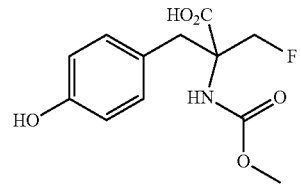 [SMILES: COC(=O)NC(CF)(Cc1ccc(O)cc1)C(=O)O]

Compound W: 3-fluoro-2-(4-hydroxybenzyl)-2-((methoxycarbonyl)amino)-propanoic Acid Added methyl chloroformate (1 eq) to a solution of (S)-2-amino-3-fluoro-2-(4-hydroxybenzyl)propanoic acid and $NaHCO_3$ (20 eq) in a mixture of $H_2O$/THF (2 M). Stir the mixture at room temperature overnight. Dilute the mixture with $H_2O$. Wash the mixture with $Et_2O$. Acidify the aqueous layer to pH~2-3. Evaporate to dryness and purified by reverse phase column chromatography to give 3-fluoro-2-(4-hydroxybenzyl)-2-((methoxycarbonyl)amino)propanoic acid with 73% yield. $^1$H NMR (400 MHz, Methanol-$d_4$) δ 6.95 (d, J=8.5 Hz, 2H), 6.79-6.59 (m, 2H), 4.70 (dt, J=47.2, 8.8 Hz, 2H), 3.66 (s, 3H), 3.15-2.93 (m, 2H). LCMS: (M+1): 272.2, (M−1): 270.1.

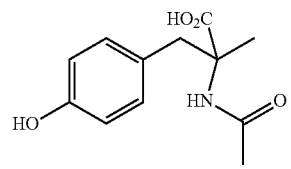 [SMILES: CC(=O)NC(C)(Cc1ccc(O)cc1)C(=O)O]

Compound X: 2-acetamido-3-(4-hydroxyphenyl)-2-methylpropanoic Acid

To a solution of 2-amino-3-(4-hydroxyphenyl)-2-methylpropanoic acid and Hunig's base (5 eq) in THF (0.2 M) was added acetic anhydride (1.5 eq). Stir the mixture at room temperature overnight. Dilute the mixture with $H_2O$. Wash the mixture with $Et_2O$. Acidify the aqueous layer to pH~2-3. Evaporate to dryness and purified by reverse phase column chromatography to give 2-acetamido-3-(4-hydroxyphenyl)-2-methylpropanoic acid with 75% yield. 1H NMR (400 MHz, Methanol-$d_4$) δ 6.93 (d, J=8.4 Hz, 2H), 6.68 (d, J=8.5 Hz, 2H), 3.26 (d, J=13.6 Hz, 2H), 3.03 (d, J=13.6 Hz, 1H), 1.92 (s, 3H), 1.37 (s, 3H). LCMS: (M+1): 238.2, (M−1): 236.2.

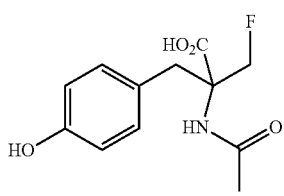 [SMILES: CC(=O)NC(CF)(Cc1ccc(O)cc1)C(=O)O]

Compound Y: 3-fluoro-2-(4-hydroxybenzyl)-2-((methoxycarbonyl)amino)propanoic Acid To a solution of (S)-2-amino-3-fluoro-2-(4-hydroxybenzyl)propanoic acid and Hunig's base (5 eq) in THF (0.2 M) was added acetic anhydride (1.5 eq). Stir the mixture at room temperature overnight. Dilute the mixture with H$_2$O. Wash the mixture with Et$_2$O. Acidify the aqueous layer to pH~2-3. Evaporate to dryness and purified by reverse phase column chromatography to give 2-acetamido-3-fluoro-2-(4-hydroxybenzyl)propanoic acid with 66% yield. $^1$H NMR (400 MHz, Methanol-d$_4$) δ 7.06-6.90 (m, 2H), 6.75-6.62 (m, 2H), 4.79-4.70 (m, 1H), 4.68-4.57 (m, 2H), 3.08 (s, 2H), 1.98 (s, 3H). LCMS: (M+Na): 278.2, (M−1): 254.2.

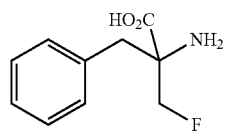 [SMILES: NC(CF)(Cc1ccccc1)C(=O)O]

Compound Z: 2-amino-2-benzyl-3-fluoropropanoic Acid

Dissolve the 2-fluoroacetonitrile (1 eq) in anhydrous Toluene (1 M). Cool the solution to 0° C. Add slowly phenylmagnesium chloride (2 M, 1 eq) to the reaction mixture under an argon atmosphere. Stir the reaction for 2 hours. Quench by adding water (5 mL) and 1M HCl (5 mL). Add 50 mL of ethyl acetate to this solution, wash the organic layer with water (2×20 ml), brine (2×20 ml). Dry over anhydrous sodium sulfate. Isolate the product by filtration and remove the solvent. Purified by column chromatography and carried to the next step directly. Ketone was transferred to a round-bottomed flask and charged with NH$_4$Cl (1.2 eq), ammonia (3 eq), ethanol (0.2 M), and water (0.2 M). Dissolve the mixture into a clear solution. Add NaCN (1.5 eq) to the mixture. Seal the flask quickly with a rubber stopper. Stir the mixture for 3 days. Extract the mixture with CH$_2$Cl$_2$ (100 mL). Wash the combined organic layer with water to remove the remaining NaCN. Dry the mixture with anhydrous sodium sulfate. Concentrate the mixture under reduced pressure to afford the corresponding amino nitrile. The residue was purified by column chromatography and carried to the next step directly. The resulting nitrile is heated under reflux with a conc HCl in dioxane (0.4 M) such as dilute hydrochloric acid. A carboxylic acid is formed was evaporate to dryness and purified by reverse phase column chromatography to give 2-amino-2-benzyl-3-fluoropropanoic acid with 59% yield. 1H NMR (400 MHz, DMSO-d6) δ 6.68-6.41 (m, 5H), 4.21 (d, J=10.3 Hz, 1H), 3.94 (dd, J=47.2, 10.3 Hz, 1H), 2.58-2.44 (m, 2H), 2.36 (d, J=14.2 Hz, 2H). LCMS: (M+): 198.2.

Example 2: Inhibition of Tyrosine Decarboxylase In Vitro

Tyrosine decarboxylase (tdc) was obtained by following a previously published literature procedure (Science, 14 Jun. 2019: Vol. 364, Issue 6445, eaau6323). Tdc (220 nM final concentration) was thawed on ice and then mixed with pyridoxal-5-phosphate (2.2 mM final concentration) in 200 mM sodium acetate buffer, pH 5.5 optionally containing 1 mM TCEP. To this mixture was added inhibitor at a final concentration of 1000, 333, 111, 37, 12, 4.1, 1.4, or 0 μM (final volume: 100 μL; inhibitor was 100-fold concentrated in a solution of DMSO, H$_2$O, or DMSO:H$_2$O (1/1 v/v)). The protein-inhibitor mixture was incubated at room temperature for 60 min. 6 μL of this mixture was then withdrawn from each solution and mixed with 54 μL of 10 mM levodopa in 200 mM sodium acetate buffer pH 5.5. The final concentration of the reaction was 22 nM tdc, 220 μM pyridoxal-5-phosphate, 9 mM levodopa in 200 mM sodium acetate buffer pH 5.5 with 0-100 μM inhibitor. The reaction was proceeded for 5 min at room temperature before quenching by addition of 540 μL acetonitrile containing 0.1 (v/v) formic acid supplemented with 200 nM tolbutamide as an internal standard. The reactions were centrifuged (3,000 g, 10 min), and then 100 μL of each supernatant was transferred to a fresh plate. 100 μL of acetonitrile containing 0.1% (v/v) formic acid supplemented with 200 nM tolbutamide was added. An external standard curve containing 0-150 μM dopamine was prepared in the exact same manner.

Dopamine formed in each reaction was quantified by using an Agilent 6470 triple quadrupole mass spectrometer equipped with an Acquity UPLC. Mobile phase A consisted of H$_2$O containing 10 mM ammonium formate, pH 3.0 and supplemented with 0.1% (v/v) formic acid. Mobile phase B consisted of acetonitrile containing 10 mM ammonium formate, pH 3.0 and supplemented with 0.1% (v/v) formic acid. 5 μL of each sample was injected onto a BEH Amide column (Waters Corporation, 2.1×50 mm, 1.7 μm). The gradient was set to: 100% mobile phase B at 0 min, decreasing linearly to 65% mobile phase B by 1.5 min, held constant at 65% mobile phase B until 2.5 min, ramped back up to 100% mobile phase B by 2.6 min, and held constant at 100% mobile phase B until 4.2 min. The flow rate was 0.6 mL/min. The dopamine was detected by using the mass spectrometer in multiple reaction monitoring (MRM) mode, quantifying the transition 154.1 to 137.0 m/z in positive mode. The fragmentor setting was 74, the collision energy was 9, and the cell accelerator voltage was 4, and the dwell time was 20. Tolbutamide was monitored using MRM and quantifying the transition of 271.1 to 91.0 m/z in positive mode. The fragmentor setting was 88, the collision energy was 37, and the cell accelerator voltage was 4, and the dwell time was 20.

The amount of dopamine was quantified by normalizing the area to the area of tolbutamide internal standard within each sample. This relative response was then compared to that of the standard curve to obtain the dopamine formed within each sample. The concentration of dopamine formed as a function of the inhibitor concentration at the preincubation stage was plotted in GraphPad Prism 8, and the IC$_{50}$ was calculated using the non-linear fit for the standard IC$_{50}$ curve equation "[inhibitor] vs response (three parameters)."

TABLE 1

| Compound | IC$_{50}$ @ 60 min (μM) |
|---|---|
| U | >1000 |
| K | Minor inhibition |
| M | 3.2 |
| L | 2.5 |
| N | 2.6 |
| V | >1000 |
| W | >1000 |
| Y | >1000 |
| Q | >1000 |
| P | >1000 |
| X | >1000 |
| O | >1000 |
| R | Minor inhibition |
| Z | >1000 |
| T | 82.3 |
| S | 4 |

Example 3: Inhibition of *E. faecalis* Decarboxylation Activity In Vitro

A vial of 200 μL of *Enterococcus faecalis* v583 was removed from the −80° C. freezer and thawed in an anaerobic chamber containing an atmosphere of either 95/5 N$_2$/H$_2$ (v/v) or 90/5/5 N$_2$/H$_2$/CO$_2$ (v/v). 200 μL was inoculated into 10 mL of sterile, anaerobic BHI broth, pH 5 (adjusted with NaOH). The culture was grown overnight at 37° C. under anaerobic conditions.

After overnight incubation, 40 μL of the saturated starter culture was mixed with 744 μL of sterile, anaerobic BHI broth, pH 5 that had been supplemented with 1.5 mM levodopa. To this was added 16 μL of a 50-fold concentrated stock solution of inhibitor that had been dissolved in either DMSO, H$_2$O, or DMSO:H$_2$O (1:1 v/v). The final concentration of the inhibitor in each condition was 0, 0.001, 0.01, 0.1, 1, 10 or 100 μM. The contents of each incubation were mixed, and then 100 μL was transferred into a fresh 96-well plate. A standard curve of levodopa (0-1.5 mM) in BHI broth, pH 5.5 was likewise prepared on a 100 μL scale and aliquoted into the plate. The plate was sealed and incubated for 24 h at 37° C. under an atmosphere of either 95/5 N$_2$/H$_2$ (v/v) or 90/5/5 N$_2$/H$_2$/CO$_2$ (v/v) in an anaerobic chamber.

After 24 h incubation, the seal was removed, and the contents of each plate was mixed with 400 μL acetonitrile containing 0.1% (v/v) formic acid and 200 nM tolbutamide as an internal standard. The samples were mixed and then centrifuged (4,000 g, 10 min). 200 μL of each supernatant was transferred to a separate plate.

The samples were analyzed by using an Agilent 6470 triple quadrupole mass spectrometer equipped with an Acquity UPLC. Mobile phase A consisted of H$_2$O containing 10 mM ammonium formate, pH 3.0 and supplemented with 0.1% (v/v) formic acid. Mobile phase B consisted of acetonitrile containing 10 mM ammonium formate, pH 3.0 and supplemented with 0.1% (v/v) formic acid. 5 μL of each sample was injected onto a BEH Amide column (Waters Corporation, 2.1×50 mm, 1.7 μm). The gradient was set to: 100% mobile phase B at 0 min, decreasing linearly to 65% mobile phase B by 1.5 min, held constant at 65% mobile phase B until 2.5 min, ramped back up to 100% mobile phase B by 2.6 min, and held constant at 100% mobile phase B until 4.2 min. The flow rate was 0.6 mL/min. The levodopa was detected by using the mass spectrometer in multiple reaction monitoring (MRM) mode, quantifying the transition 198.1 to 151.9 m/z in positive mode. The fragmentor setting was 78, the collision energy was 13, and the cell accelerator voltage was 4, and the dwell time was 20. Tolbutamide was monitored using MRM and quantifying the transition of 271.1 to 91.0 m/z in positive mode. The fragmentor setting was 88, the collision energy was 37, and the cell accelerator voltage was 4, and the dwell time was 20.

The amount of levodopa was quantified by comparing normalizing the area to the area of tolbutamide internal standard within each sample. This relative response was then compared to that of the standard curve to obtain the residual levodopa within each sample. The concentration of levodopa remaining as a function of inhibitor concentration was then plotted in GraphPad Prism 8, and the IC$_{50}$ was calculated using the non-linear fit for the standard IC$_{50}$ curve equation "[inhibitor] vs response (three parameters)."

TABLE 2

| Compound | IC$_{50}$ @ 60 min (μM) |
|---|---|
| V | >1000 |
| W | >1000 |
| Y | >1000 |
| Q | >1000 |
| P | >1000 |
| X | >1000 |
| O | >1000 |
| R | >1000 |
| Z | >1000 |
| T | 18.5 |
| S | 2 |

Example 4: Inhibition of Dopamine Production in Fecal Matter

This example is representative of the methods described in Example 8. Fecal samples may be assayed for the presence of the tydc gene by attempting to amplify the gene with primers specific for it by qPCR. Samples that give a signal below the detection limit may be used in subsequent steps.

Following steps 1-2 as detailed in Example 6, *E. faecalis* v583 may be grown.

*E. faecalis* v583 may be added to the samples obtained in step 1 at a dilution level calculated to represent 0, 0.1, 1, 2, 5, or 10% of all organisms present. The substrate (d$_4$-L-DOPA, 1 mM final concentration) may be added to the mixture. An inhibitor of TyDC may also be added at this time at a final concentration of 10 μM. Optionally, the IC$_{50}$ of an inhibitor may instead be determined by adding an inhibitor across a range of appropriate concentrations, for example, 0, 0.001, 0.01, 0.1, 1, and 10 μM.

After incubation for a designated period of time and at a certain temperature (for example, 8 h at 37° C.), samples will be rendered compatible with LCMS analysis and the amount of product will be determined using LCMS analysis as in Example 4.

OTHER EMBODIMENTS

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.
Other embodiments are in the claims.
What is claimed is:
1. A compound chosen from the following compounds
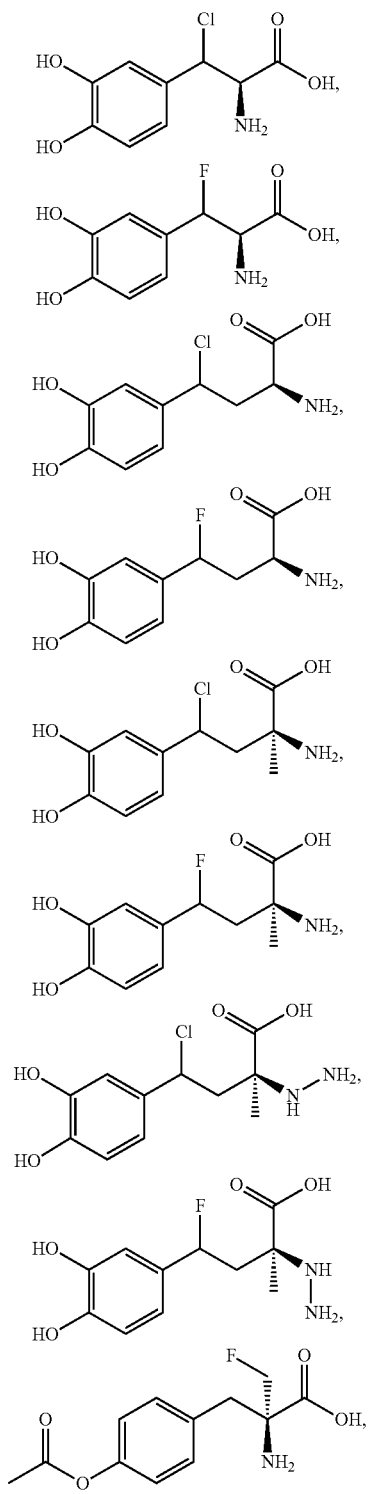
-continued
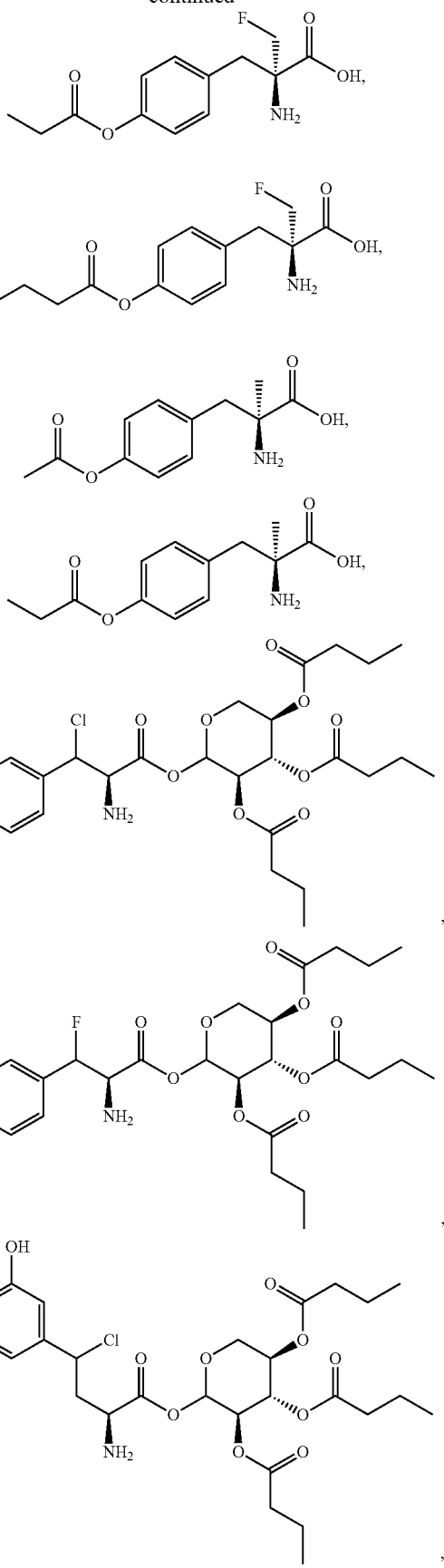

77
-continued
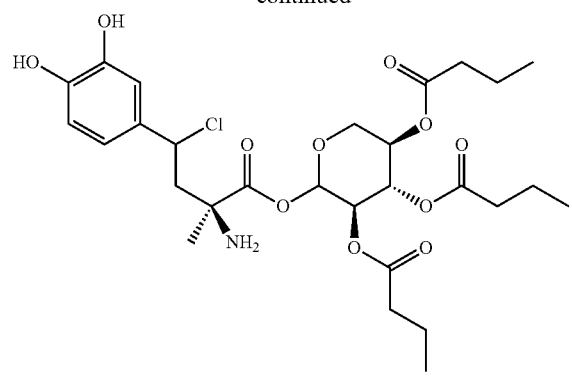
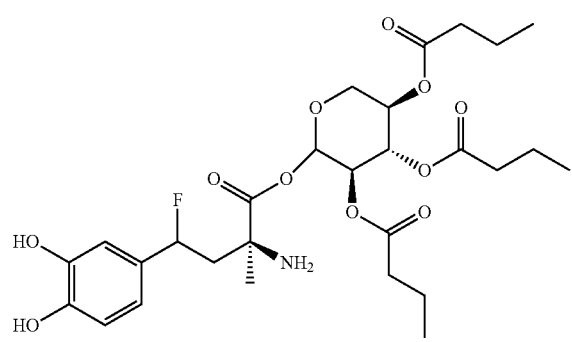
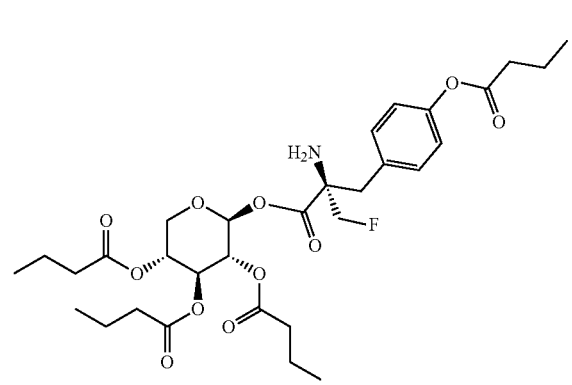
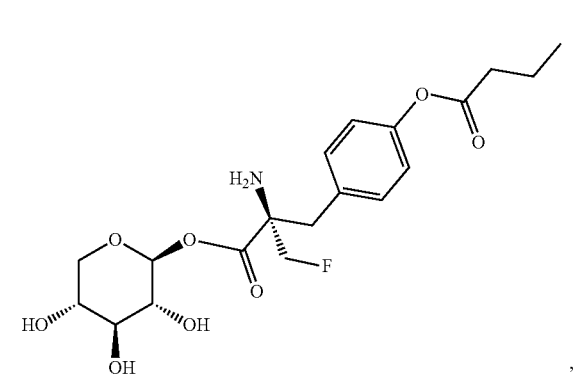
78
-continued
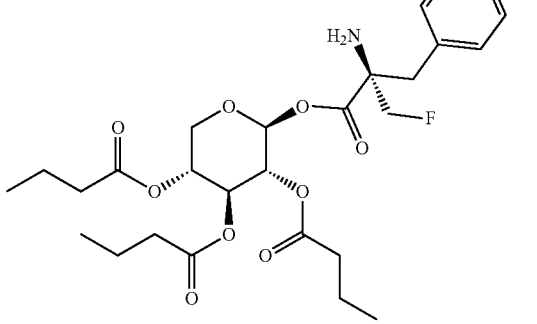
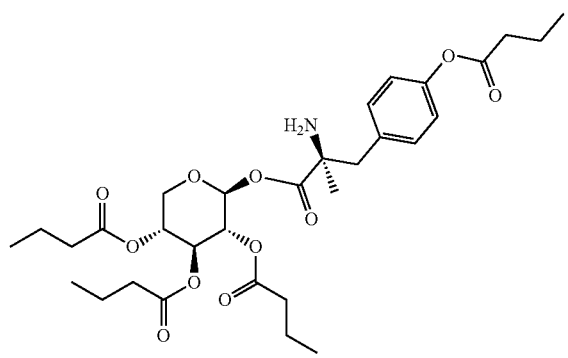
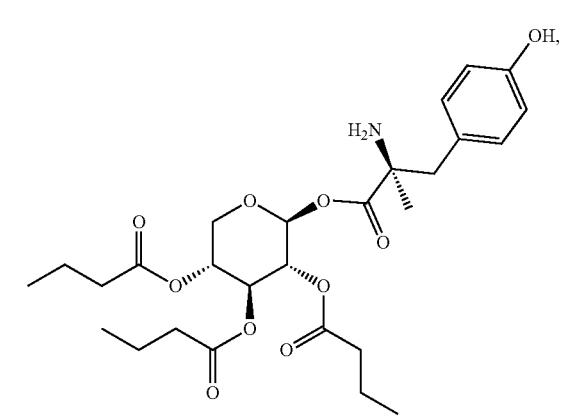
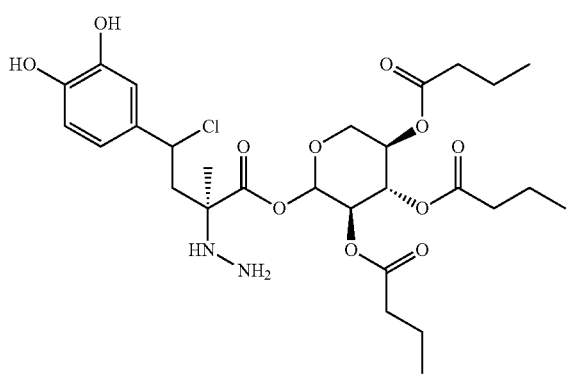

-continued
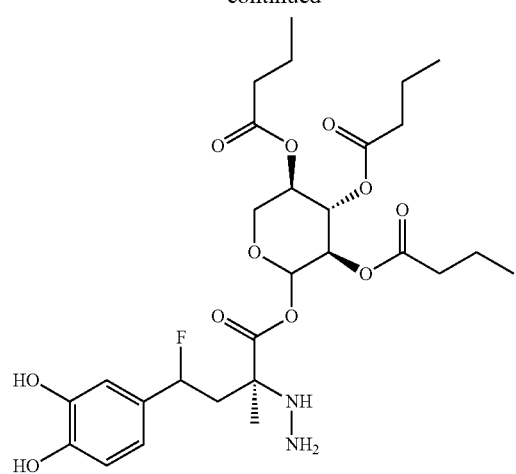
and pharmaceutically acceptable salts thereof.
2. A compound chosen from the following compounds
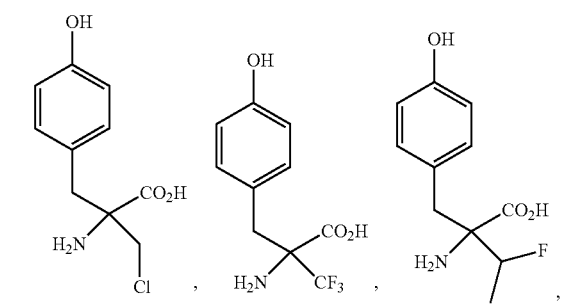
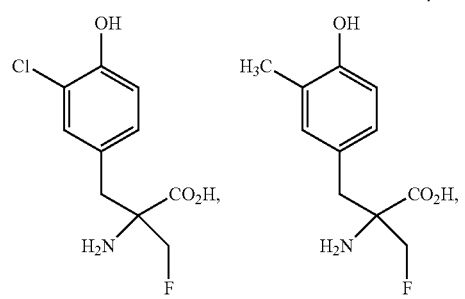
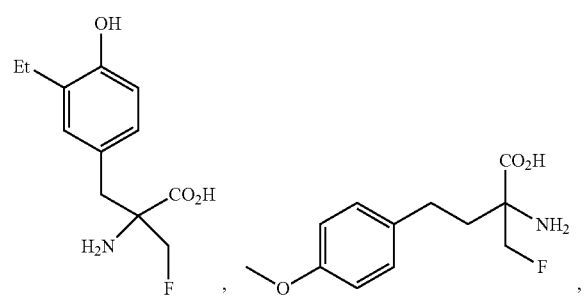
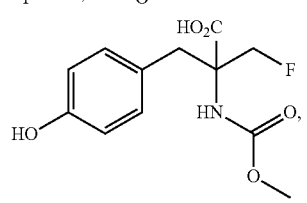
-continued
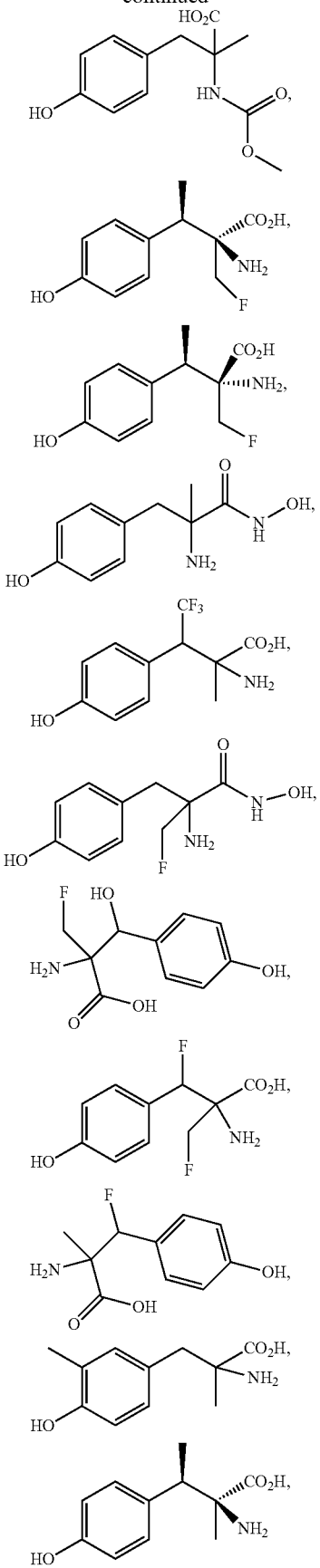

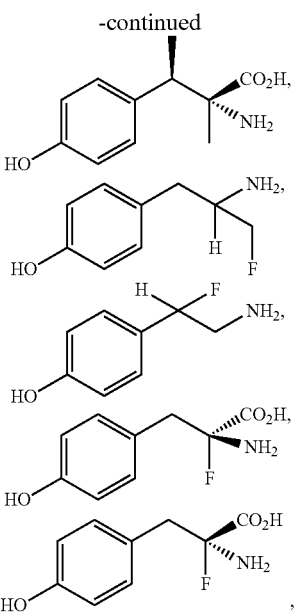

and pharmaceutically acceptable salts thereof.

3. A compound of formula (I):

(I)

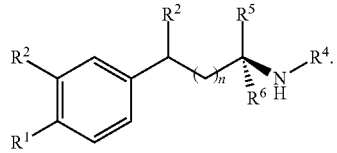

or a pharmaceutically acceptable salt thereof,
wherein
n is 0 or 1;
$R^1$ is H or —$OR^A$, wherein $R^A$ is H, —C(O) $C_{1-6}$ alkyl, or an acylated sugar;
$R^2$ is H, halogen, amino, $C_{1-6}$ alkyl, or —$OR^A$, wherein $R^A$ is H or an acylated sugar;
$R^3$ is H, a halogen, or $C_{1-6}$ alkyl optionally substituted with one or more halogens;
$R^4$ is H, —$NH_2$, —C(O)OCH$_3$, or an acylated sugar;
$R^5$ is —C(O)OH, —C(O)O$C_{1-6}$ alkyl, —C(O)Oglycoside, —C(O)NHOH, or —C(O)O(acylated sugar); and
$R^6$ is H, halogen, or optionally substituted $C_{1-6}$ alkyl;
provided that at least one $R^A$ is present or that $R^3$ and/or $R^6$ comprise a halogen;
provided that at least one of $R^1$ and $R^2$ is —$OR^A$;
provided that, when both $R^1$ and $R^2$ are —$OR^A$ wherein $R^A$ is H, then $R^3$ is not H; and
provided that, when n is 0, $R^1$ is —$OR^A$ wherein $R^A$ is H, $R^2$ is H or halogen, $R^4$ is H or $NH_2$, $R^5$ is —C(O)OH, and $R^6$ is H or optionally substituted $C_1$ alkyl, then $R^3$ is not H.

4. The compound of formula (I) according to claim 3, or a pharmaceutically acceptable salt thereof, wherein the compound is a compound of formula (I-a):

(I-a)

5. The compound of formula (I) according to claim 3, or a pharmaceutically acceptable salt thereof, wherein
n is 0 or 1;
$R^1$ is H or —$OR^A$, wherein $R^A$ is H, —C(O) $C_{1-6}$ alkyl, or an acylated sugar;
$R^2$ is H or —$OR^A$, wherein $R^A$ is H or an acylated sugar;
$R^3$ is H or a halogen;
$R^4$ is H, —$NH_2$, or an acylated sugar;
$R^5$ is —C(O)OH, —C(O)O$C_{1-6}$ alkyl, —C(O)Oglycoside, or —C(O)O (acylated sugar); and
$R^6$ is H or optionally substituted $C_{1-6}$ alkyl;
provided that at least one $R^A$ is present or that $R^3$ and/or $R^6$ comprise a halogen.

6. The compound of formula (I) according to claim 3, or a pharmaceutically acceptable salt thereof, wherein $R^1$ is —$OR^A$.

7. The compound of formula (I) according to claim 3, or a pharmaceutically acceptable salt thereof, wherein $R^2$ is H or —$OR^A$.

8. The compound of formula (I) according to claim 3, wherein each $R^A$ is H.

9. The compound of formula (I) according to claim 3, or a pharmaceutically acceptable salt thereof, wherein $R^2$ is a halogen.

10. The compound of formula (I) according to claim 3, or a pharmaceutically acceptable salt thereof, wherein $R^3$ is fluoro or chloro.

11. The compound of formula (I) according to claim 3, or a pharmaceutically acceptable salt thereof, wherein $R^3$ is H.

12. The compound of formula (I) according to claim 3, or a pharmaceutically acceptable salt thereof, wherein $R^4$ is H.

13. The compound of formula (I) according to claim 3, or a pharmaceutically acceptable salt thereof, wherein $R^4$ is —$NH_2$.

14. The compound of formula (I) according to claim 3, or a pharmaceutically acceptable salt thereof, wherein $R^5$ is —C(O)OH or C(O)O (acylated sugar).

15. The compound of formula (I) according to claim 3, or a pharmaceutically acceptable salt thereof, wherein $R^6$ is H, a $C_{1-6}$ alkyl, or a $C_{1-6}$ alkyl substituted with one, two, or three halogens.

16. The compound of formula (I) according to claim 3, or a pharmaceutically acceptable salt thereof, wherein n is 0.

17. The compound of formula (I) according to claim 3, or a pharmaceutically acceptable salt thereof, wherein
n is 0;
$R^1$ is —OH;
$R^2$ is halogen;
$R^3$ is H, a halogen, or $C_{1-6}$ alkyl optionally substituted with one or more halogens;
$R^4$ is H, —$NH_2$, or an acylated sugar;
$R^5$ is —C(O)OH, —C(O)O$C_{1-6}$ alkyl, —C(O)Oglycoside, —C(O) NHOH, or —C(O)O (acylated sugar); and
$R^6$ is H or optionally substituted $C_{1-6}$ alkyl.

18. A pharmaceutical composition comprising at least one pharmaceutically acceptable excipient and at least one entity chosen from the compounds according to claim 3 and pharmaceutically acceptable salts thereof.

19. A method of treating Parkinson's disease comprising administering to a subject in need thereof a therapeutically effective amount of at least one entity chosen from the compounds according to claim 3 and pharmaceutically acceptable salts thereof.

\* \* \* \* \*

UNITED STATES PATENT AND TRADEMARK OFFICE
CERTIFICATE OF CORRECTION

PATENT NO. : 12,162,902 B2
APPLICATION NO. : 17/299854
DATED : December 10, 2024
INVENTOR(S) : Devin Forest Reed Doud et al.

Page 1 of 1

It is certified that error appears in the above-identified patent and that said Letters Patent is hereby corrected as shown below:

In the Claims

Claim 3, Column 81, Lines 30-36, in the structure for the compound of formula (I),

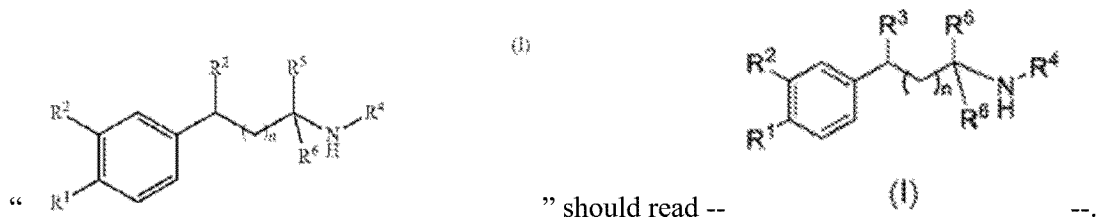

Claim 4, Column 82, Lines 1-8, in the structure for the compound of formula (I-a),

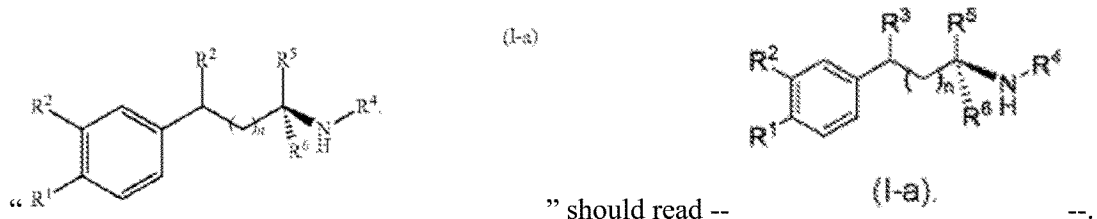

Signed and Sealed this
Twenty-first Day of January, 2025

Coke Morgan Stewart
*Acting Director of the United States Patent and Trademark Office*